United States Patent
Miyazaki

(10) Patent No.: US 10,930,858 B2
(45) Date of Patent: Feb. 23, 2021

(54) NITROGEN-CONTAINING COMPOUND AND ORGANIC ELECTROLUMINESCENCE DEVICE INCLUDING THE SAME

(71) Applicant: Samsung Display Co., Ltd., Yongin-si (KR)

(72) Inventor: Yuuki Miyazaki, Yokohama (JP)

(73) Assignee: Samsung Display Co., Ltd., Yongin-si (KR)

(*) Notice: Subject to any disclaimer, the term of this patent is extended or adjusted under 35 U.S.C. 154(b) by 318 days.

(21) Appl. No.: 15/980,270

(22) Filed: May 15, 2018

(65) Prior Publication Data

US 2019/0131534 A1 May 2, 2019

(30) Foreign Application Priority Data

Oct. 31, 2017 (KR) .................. 10-2017-0144162

(51) Int. Cl.
*H01L 51/00* (2006.01)
*H01L 51/50* (2006.01)

(52) U.S. Cl.
CPC ...... *H01L 51/0072* (2013.01); *H01L 51/0062* (2013.01); *H01L 51/0071* (2013.01);
(Continued)

(58) Field of Classification Search
CPC ...... H01L 51/005–0074; H01L 51/5012–5016
See application file for complete search history.

(56) References Cited

U.S. PATENT DOCUMENTS

| | | | |
|---|---|---|---|
| 6,761,981 B2 * | 7/2004 | Guofang | C07D 257/10 313/504 |
| 9,054,321 B2 | 6/2015 | Park et al. | |

(Continued)

FOREIGN PATENT DOCUMENTS

| | | |
|---|---|---|
| FR | 2300762 | 9/1976 |
| JP | 51-83629 | 7/1976 |

(Continued)

OTHER PUBLICATIONS

EPO Extended Search Report dated Jan. 31, 2019, for corresponding European Patent Application 18193890.3 (6 pages).

(Continued)

*Primary Examiner* — William E McClain
(74) *Attorney, Agent, or Firm* — Lewis Roca Rothgerber Christie LLP

(57) ABSTRACT

A nitrogen-containing compound which improves emission efficiency, and an organic electroluminescence device including the same are provided. The nitrogen-containing compound according to the present disclosure is represented by Formula 1:

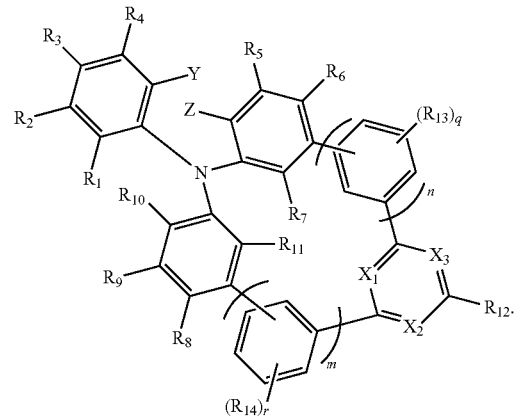

Formula 1

When the nitrogen-containing compound has an appropriate or suitable cyclic molecular structure, a small $\Delta E_{ST}$ value (Continued)

may be obtained, and an organic electroluminescence device including the nitrogen-containing compound in the emission layer may exhibit thermally activated delayed fluorescence emission and have improved external quantum efficiency.

20 Claims, 2 Drawing Sheets

(52) U.S. Cl.
CPC ...... *H01L 51/5012* (2013.01); *H01L 51/5056* (2013.01); *H01L 51/5072* (2013.01); *H01L 51/5088* (2013.01); *H01L 51/5092* (2013.01); *H01L 51/5096* (2013.01)

(56) References Cited

U.S. PATENT DOCUMENTS

| | | | |
|---|---|---|---|
| 2015/0287931 A1 | 10/2015 | Kato et al. | |
| 2016/0285009 A1 | 9/2016 | Dyatkin et al. | |
| 2018/0138419 A1* | 5/2018 | Dyatkin | C09K 11/025 |

FOREIGN PATENT DOCUMENTS

| | | | |
|---|---|---|---|
| JP | 3890276 | | 3/2007 |
| JP | 2007-194506 A | | 8/2007 |
| JP | 5617645 | | 11/2014 |
| JP | 5851929 | | 2/2016 |
| KR | 20120088644 A | * | 8/2012 |
| KR | 10-2013-0042368 | | 4/2013 |
| KR | 10-1434724 | | 8/2014 |
| KR | 10-1452577 | | 10/2014 |
| KR | 10-2015-0000967 | | 1/2015 |
| KR | 10-1554386 | | 9/2015 |
| WO | WO 2013/147431 A1 | | 10/2013 |
| WO | WO 2014/104600 A1 | | 7/2014 |

OTHER PUBLICATIONS

Hatakeyama, et al., "Ultrapure Blue Thermally Activated Delayed Fluorescence Molecules: Efficient HOMO-LUMO Separation by the Multiple Resonance Effect," Advanced Materials, vol. 28, 2016, pp. 2777-2781.
Im, et al., "Molecular Design Strategy of Organic Thermally Activated Delayed Fluorescence Emitters," Chemistry of Materials, vol. 29, 2017, pp. 1946-1963.
Kim, et al., "Hole Transporting Properties of Cyclic Pentamer of 4-Butyltriphenylamine," Chemistry Letters, 2017, 4 Pages.
Shizu, et al., "Theoretical design of a hole-transporting molecule: hexaaza[1$_6$] parabiphenylophane," Journal of Materials Chemistry, vol. 21, 2011, pp. 6375-6382.

* cited by examiner

NITROGEN-CONTAINING COMPOUND AND ORGANIC ELECTROLUMINESCENCE DEVICE INCLUDING THE SAME

CROSS-REFERENCE TO RELATED APPLICATION

This patent application claims priority to and the benefit of Korean Patent Application No. 10-2017-0144162, filed on Oct. 31, 2017, the entire content of which is hereby incorporated by reference.

BACKGROUND

The present disclosure relates to a nitrogen-containing compound and an organic electroluminescence device including the same, and for example, to a nitrogen-containing compound utilized as a delayed fluorescence emission material and an organic electroluminescence device including the same.

Recently, the development of organic electroluminescence display devices as image display devices is being actively conducted. Organic electroluminescence display devices differ from liquid crystal display devices in that they are so-called self-luminescent display devices. In self-luminescent display devices, holes and electrons injected from a first electrode and a second electrode, respectively, recombine in an emission layer, and a light emission material including an organic compound in the emission layer emits light upon the hole-electron recombination to thereby display an image.

In the application of an organic electroluminescence device to a display device, a decrease in driving voltage and an increase in emission efficiency and lifetime of the organic electroluminescence device are desired. The continuous development of materials for an organic electroluminescence device that can stably attain such features is also desired.

Recently, in order to achieve organic electroluminescence devices having high efficiency, strategies relying on phosphorescence emission using triplet state energy or delayed fluorescence emission using the phenomenon of producing singlet excitons by the collision of triplet excitons (triplet-triplet annihilation, TTA) is being developed. Further, a strategy utilizing delayed fluorescence phenomenon via a thermally activated delayed fluorescence (TADF) material is also being developed.

SUMMARY

One or more aspects of embodiments of the present disclosure provide a nitrogen-containing compound that is a luminescence (e.g., luminescent) material for an organic electroluminescence device and that is capable of improving emission efficiency.

The present disclosure also provides an organic electroluminescence device having improved emission efficiency by including the nitrogen-containing compound.

One or more embodiments of the present disclosure provide a nitrogen-containing compound represented by Formula 1:

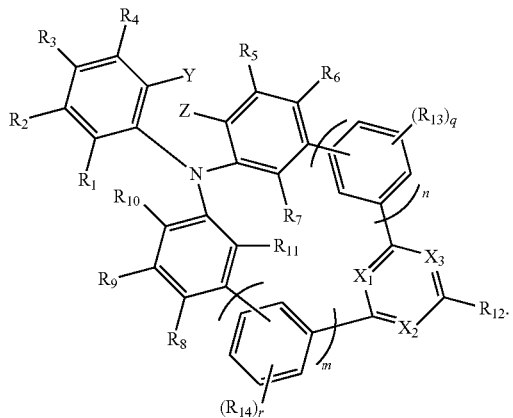

Formula 1

In Formula 1, at least two of $X_1$, $X_2$, and $X_3$ may be N, and the remainder thereof may be $CR_{15}$; Y and Z may each independently be a hydrogen atom, a deuterium atom, $OR_{16}$, $SR_{17}$, $CR_{18}R_{19}R_{20}$, or $SiR_{21}R_{22}R_{23}$, or may be combined with (e.g., linked to) each other to form a ring; $R_1$ to $R_{14}$ may each independently be a hydrogen atom, a deuterium atom, $OR_{24}$, $SR_{25}$, $(C=O)R_{26}$, $NR_{27}R_{28}$, $CR_{29}R_{30}R_{31}$, $SiR_{32}R_{33}R_{34}$, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, or may be combined with (e.g., linked to) an adjacent group to form a ring; $R_{15}$ to $R_{34}$ may each independently be a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, or may be combined with (e.g., linked to) an adjacent group to form a ring; n and m may each independently be 1 or 2; and q and r may each independently be an integer of 0 to 4.

In some embodiments, $X_1$ may be N, and at least one of $X_2$ or $X_3$ may be N.

In some embodiments, n and m may be 1.

In some embodiments, m may be 1, and n may be 1 or 2.

In some embodiments, $R_{12}$ may be a substituted or unsubstituted phenyl group or a substituted or unsubstituted dibenzofuran group.

In some embodiments, Formula 1 may be a nitrogen-containing compound represented by Formula 1-1 or Formula 1-2:

Formula 1-1

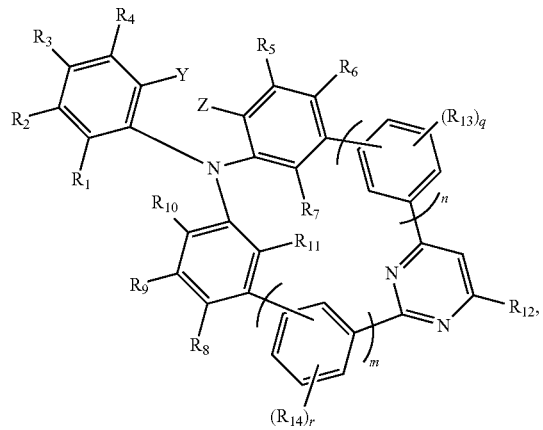

In some embodiments, Formula 1 may be a nitrogen-containing compound represented by Formula 1-3 or Formula 1-4:

Formula 1-3

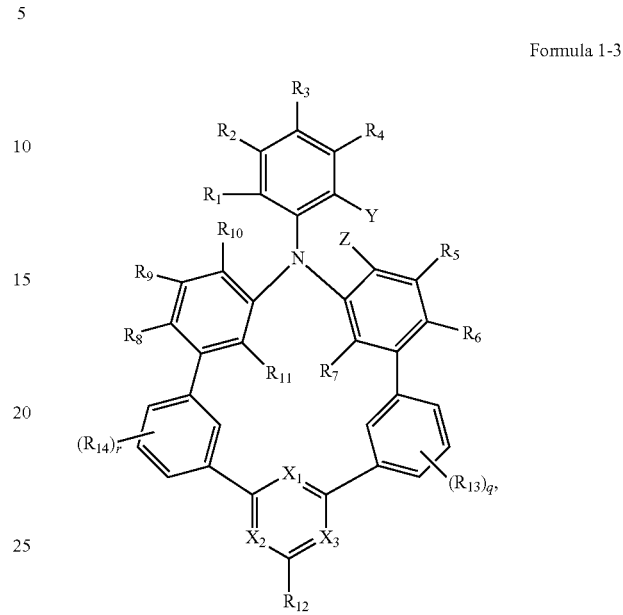

Formula 1-2

Formula 1-4

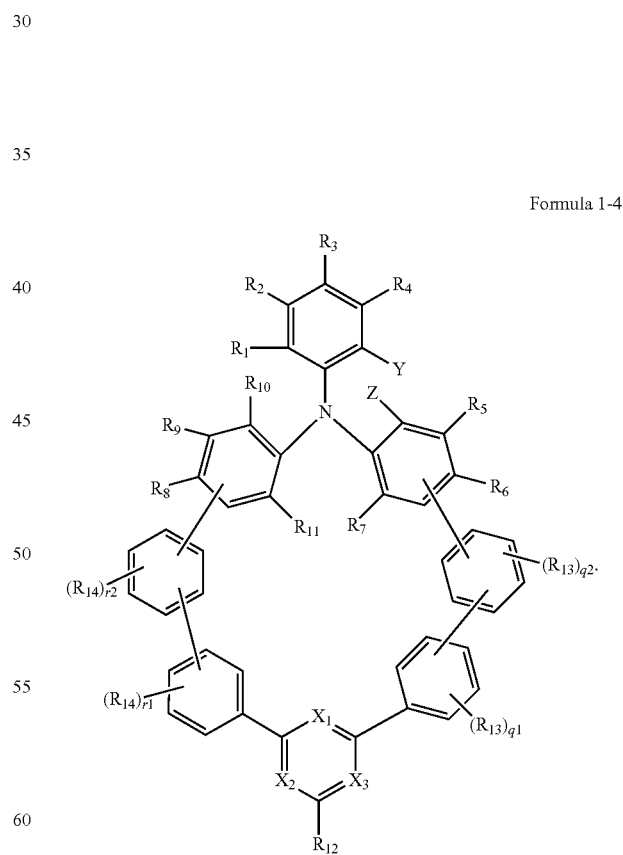

In Formula 1-1 and Formula 1-2, Y, Z, n, m, $R_1$ to $R_{34}$, q, and r may each independently be the same as defined in Formula 1.

In Formula 1-4, q1, q2, r1, and r2 may each independently be an integer of 0 to 4; and in Formula 1-3 and Formula 1-4, $X_1$ to $X_3$, Y, Z, $R_1$ to $R_{34}$, q, and r may each independently be the same as defined in Formula 1.

In some embodiments, Formula 1 may be a nitrogen-containing compound represented by Formula 1-5 or Formula 1-6:

Formula 1-5

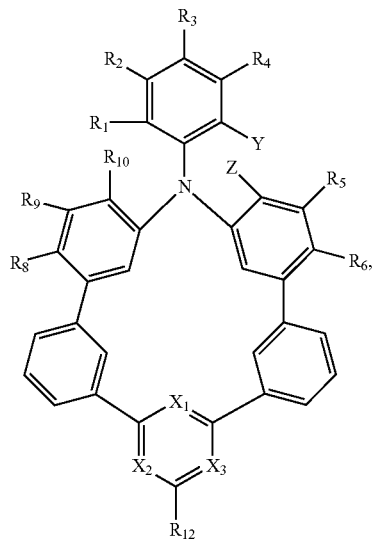

Formula 1-6

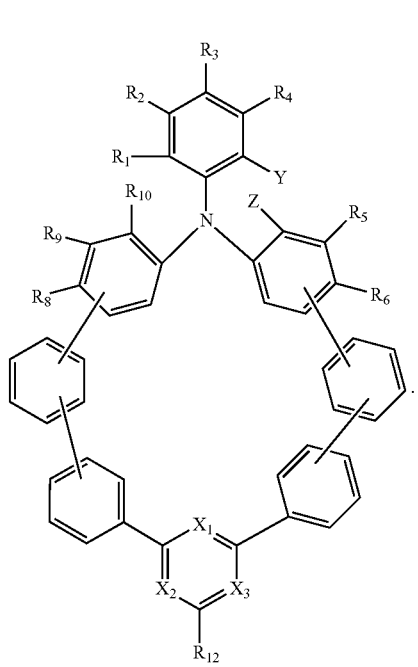

In Formula 1-5 and Formula 1-6, $X_1$ to $X_3$, Y, Z, $R_1$ to $R_6$, $R_8$, $R_9$, $R_{10}$ and $R_{12}$ may each independently be the same as defined in Formula 1.

In some embodiments, the nitrogen-containing compound represented by Formula 1 may have a difference between the lowest excitation singlet energy level (S1) and the lowest excitation triplet energy level (T1) of about 0.2 eV or less.

In some embodiments, the nitrogen-containing compound represented by Formula 1 may be a thermally activated delayed fluorescence emission material.

In some embodiments, the nitrogen-containing compound represented by Formula 1 may be a compound represented in Compound Group 1:

Compound Group 1

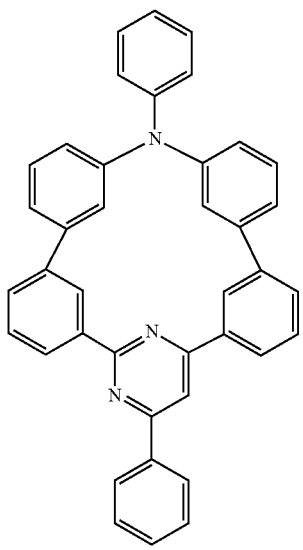

1

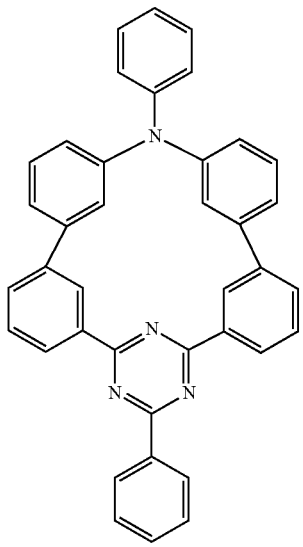

2

3
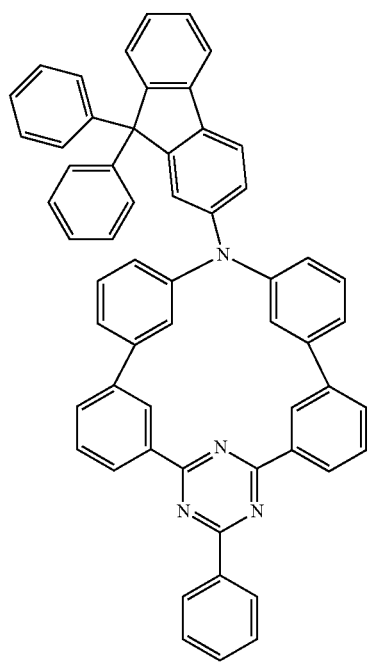
5
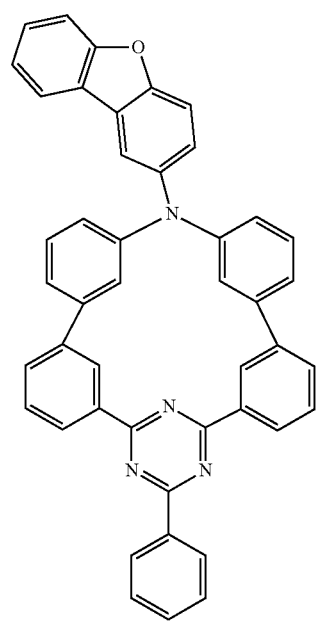
4
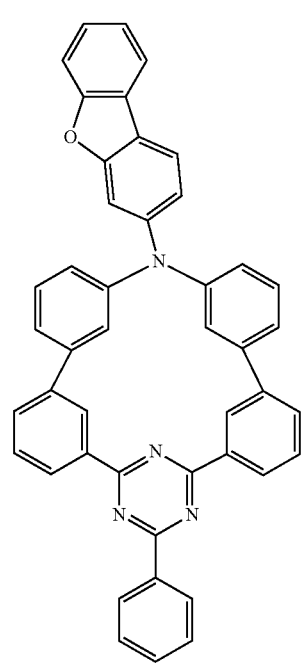
6
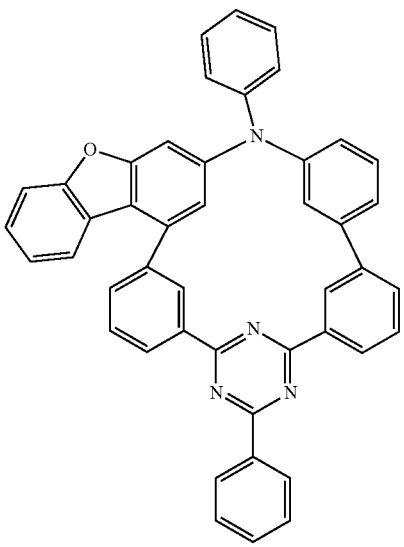

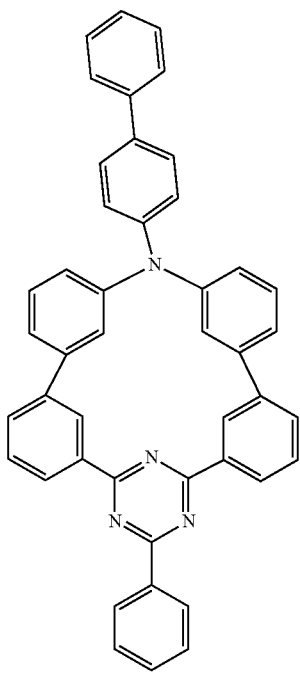
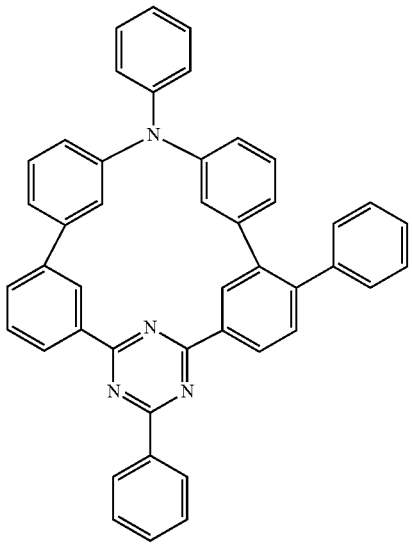
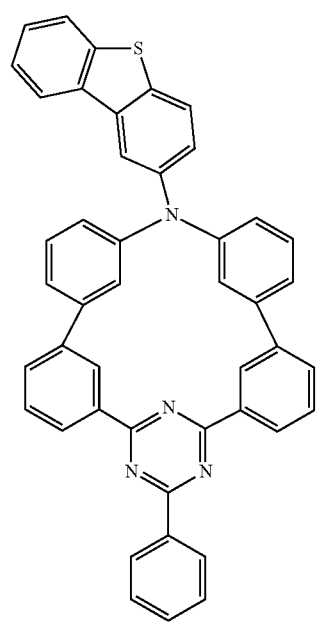
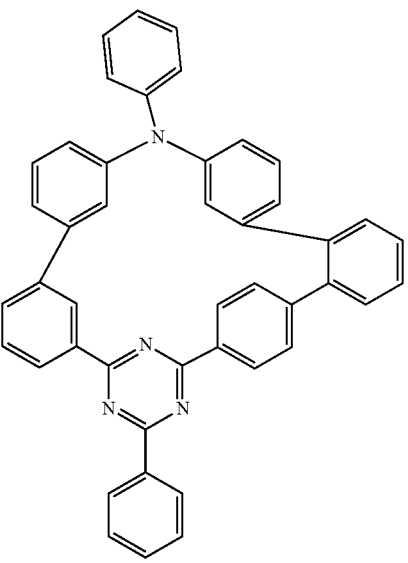

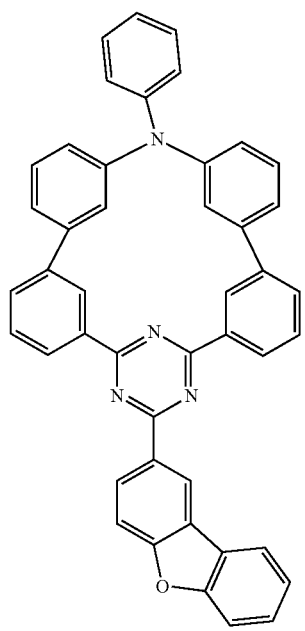
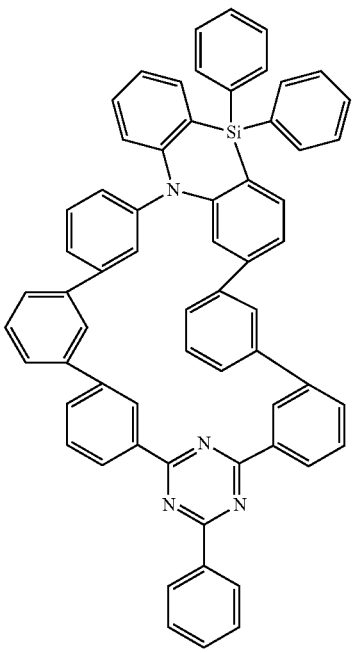
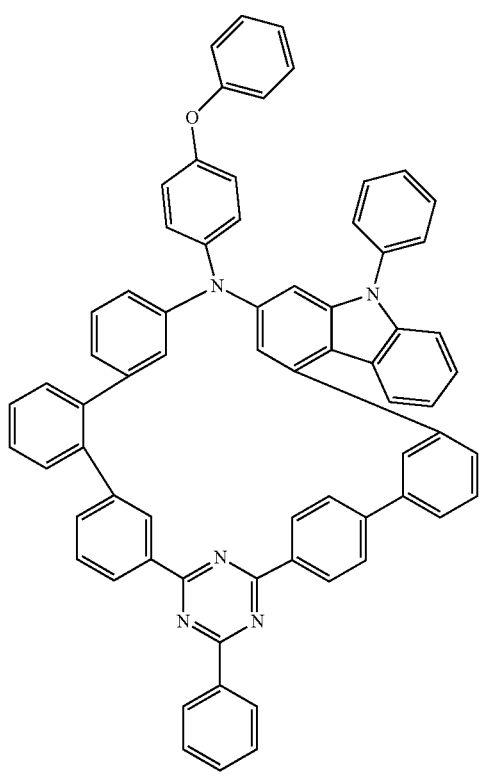
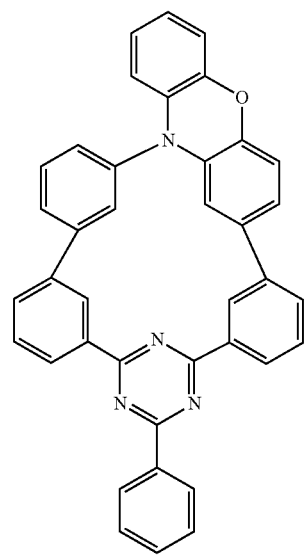

15
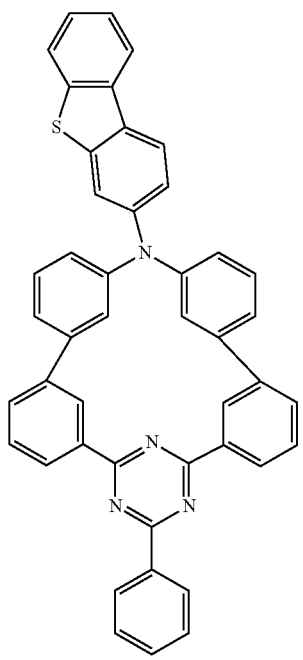
16
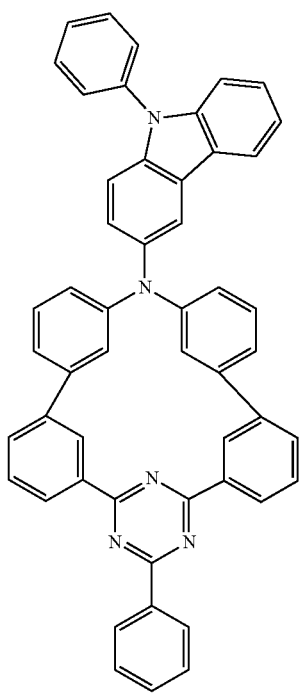
17
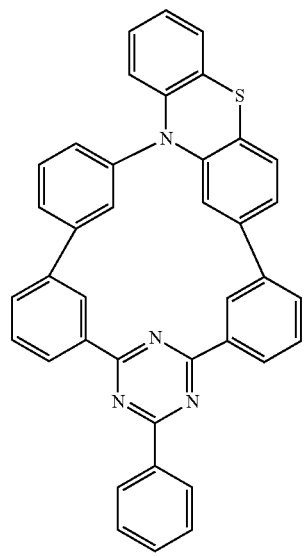
18
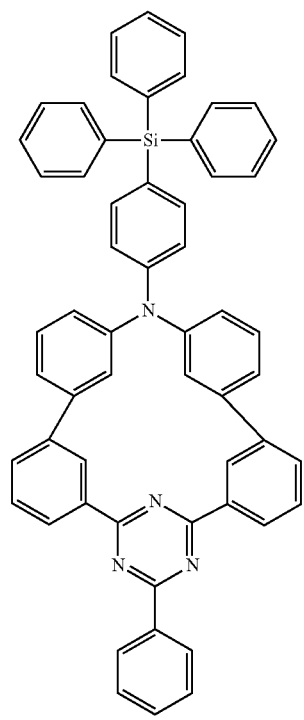

19
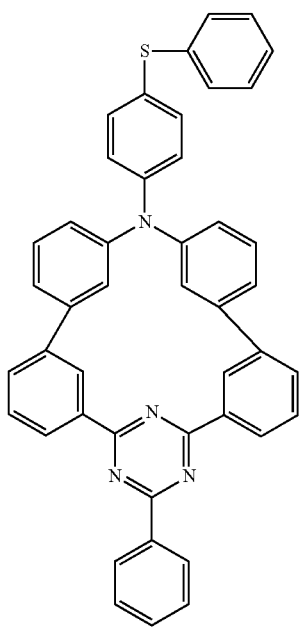
20
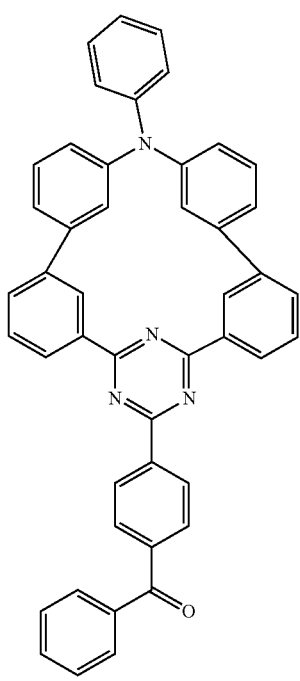
21
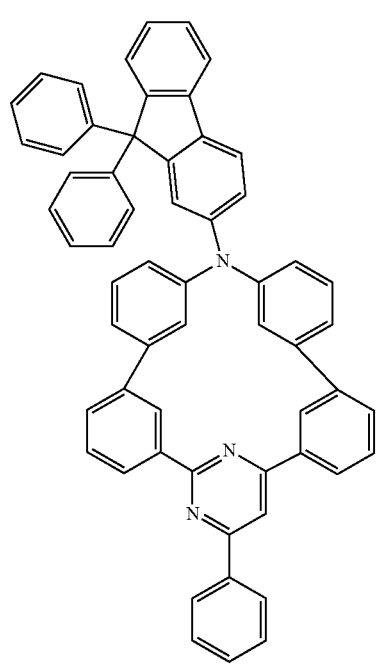
22
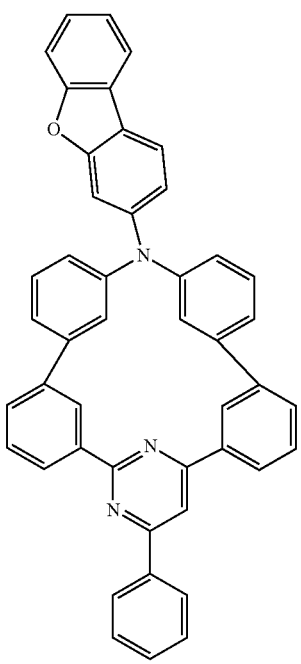

23
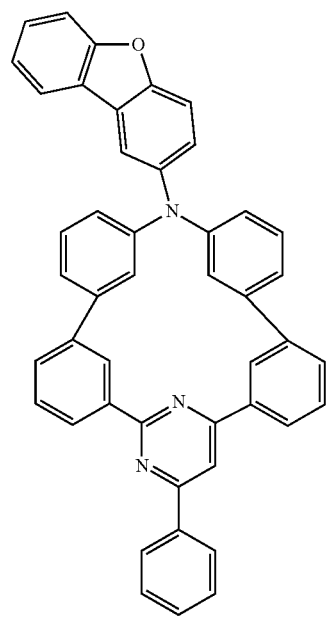
24
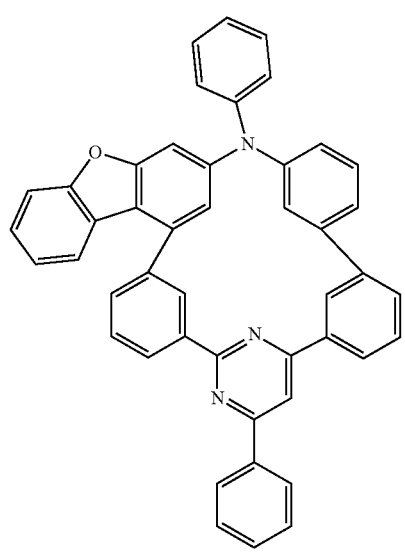
25
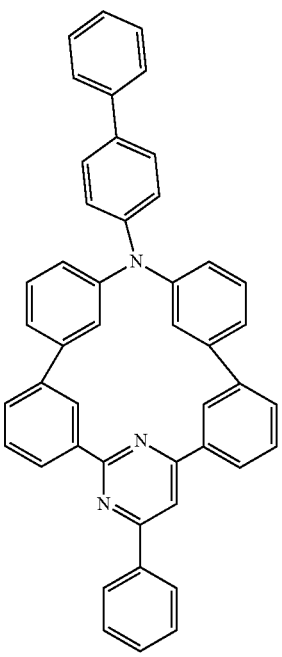
26
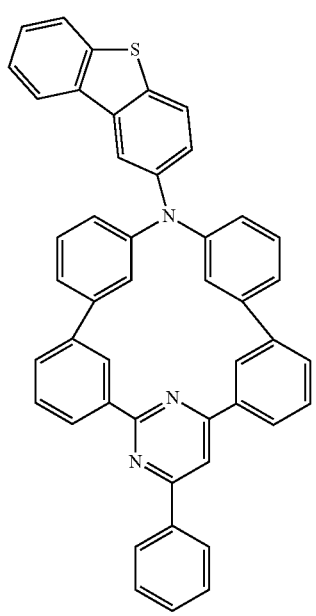

27
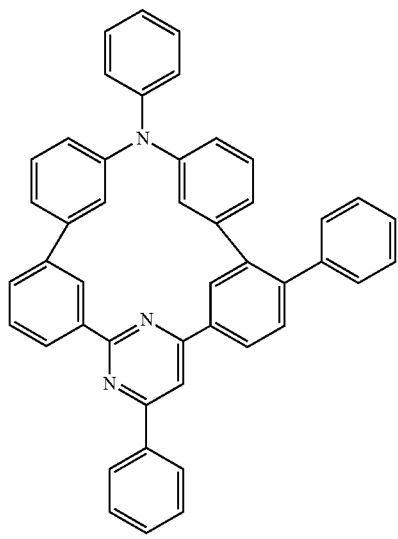
28
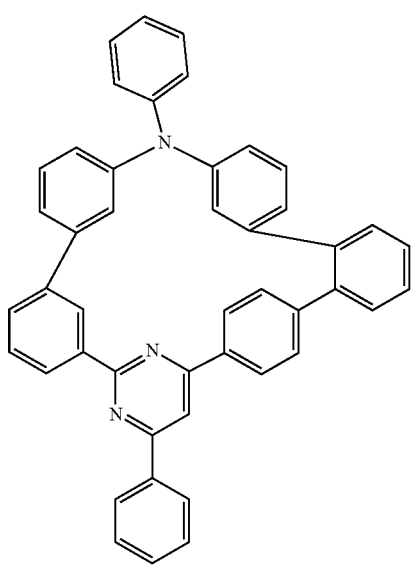
29
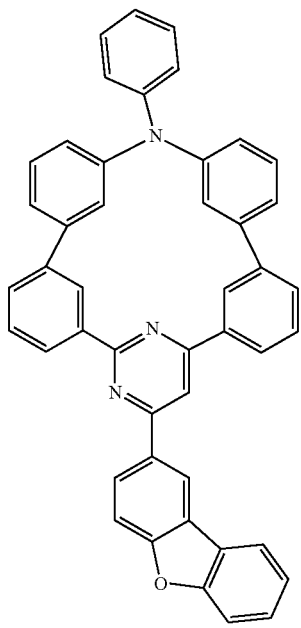
30
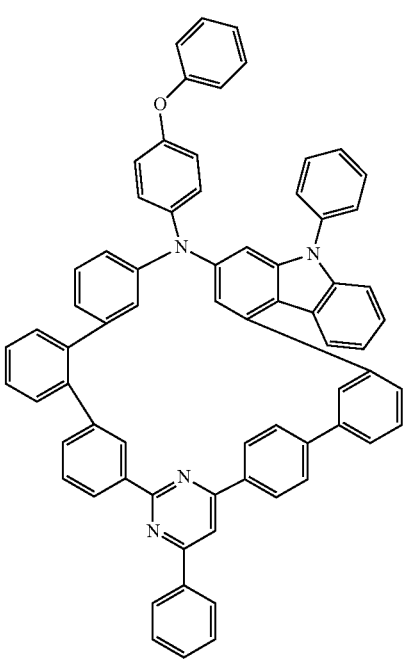

31
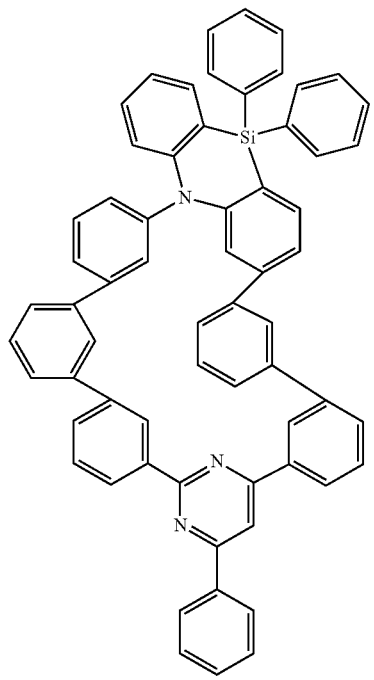
32
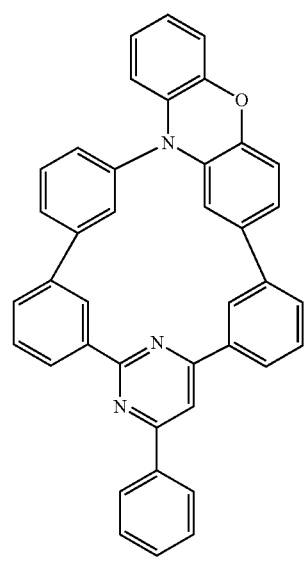
33
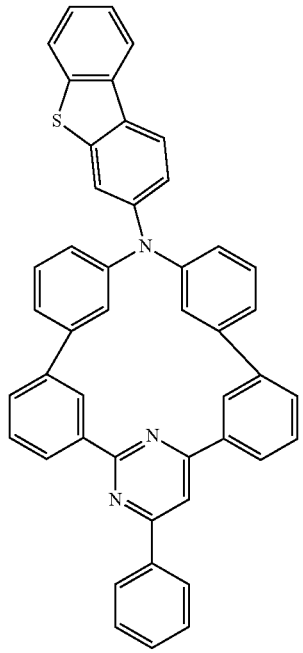
34
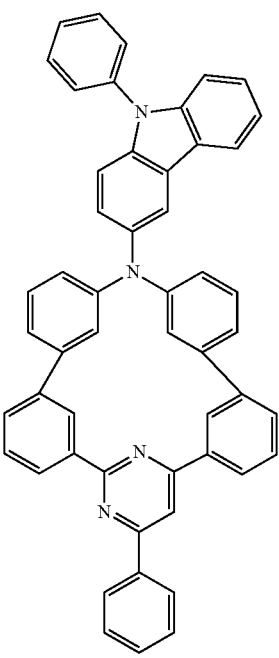

35

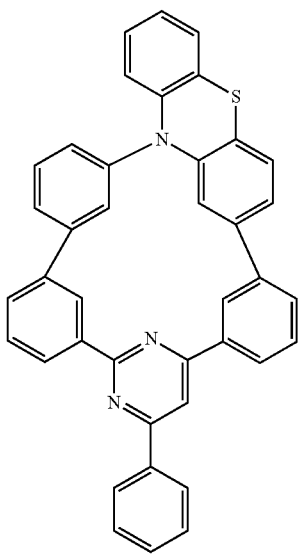

36

37

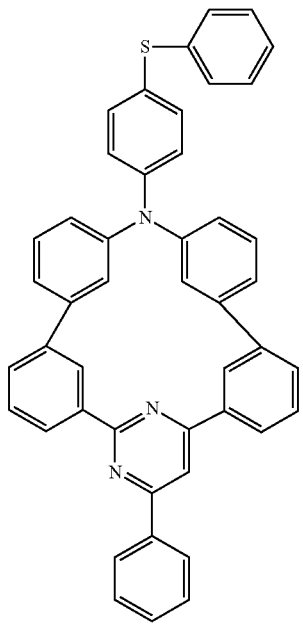

38

In some embodiments of the present disclosure, an organic electroluminescence device includes a first electrode, a hole transport region on the first electrode, an emission layer on the hole transport region and including the nitrogen-containing compound according to an embodiment of the present disclosure, an electron transport region on the emission layer, and a second electrode on the electron transport region. The first electrode and the second electrode may each independently include at least one selected from Ag, Mg, Cu, Al, Pt, Pd, Au, Ni, Nd, Ir, Cr, Li, Ca, LiF/Ca, LiF/Al, Mo, Ti, In, Sn, and Zn, a compound of two or more thereof, a mixture of two or more thereof, and an oxide thereof.

In some embodiments, the emission layer may be to emit delayed fluorescence.

In some embodiments, the emission layer may be an emission layer of a thermally activated delayed fluorescence, which may be to emit blue light.

In some embodiments, the emission layer may include a host and a dopant, and the dopant may be the nitrogen-containing compound represented by Formula 1.

In some embodiments, the host may include at least one of bis[2-(diphenylphosphino)phenyl] ether oxide (DPEPO), 4,4'-bis(carbazol-9-yl)biphenyl (CBP), 1,3-bis(carbazol-9-yl)benzene (mCP), 2,8-bis(diphenylphosphoryl)dibenzo[b,d]furan (PPF), 4,4',4"-tris(carbazol-9-yl)-triphenylamine (TcTa), 1,3,5-tris(N-phenylbenzimidazole-2-yl)benzene (TPBi), 3,3'-di(9H-carbazol-9-yl)-1,1'-biphenyl (mCBP), or (2,4,6-tris(biphenyl-3-yl)-1,3,5-triazine (T2T).

In some embodiments, the emission layer may include at least one nitrogen-containing compound represented in Compound Group 1:

Compound Group 1

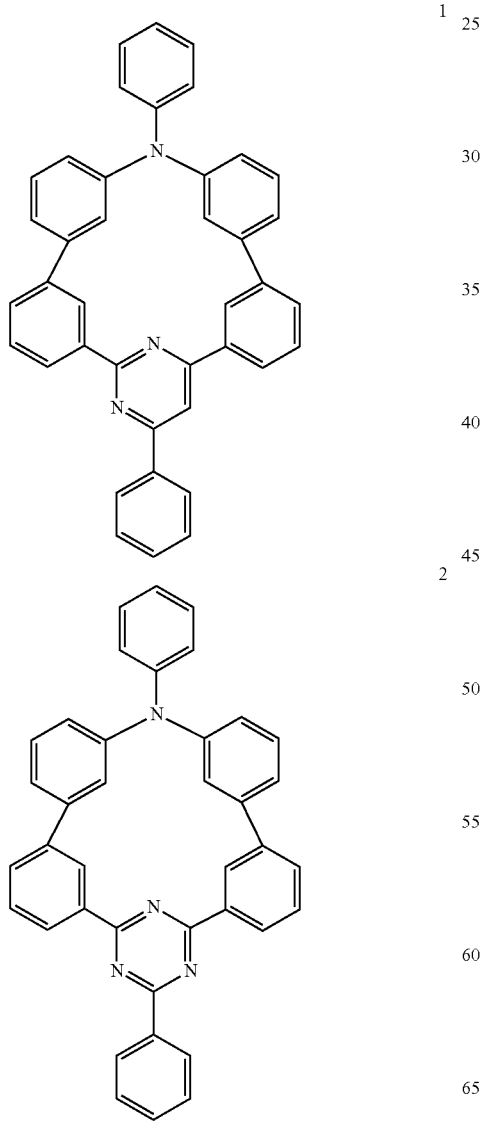

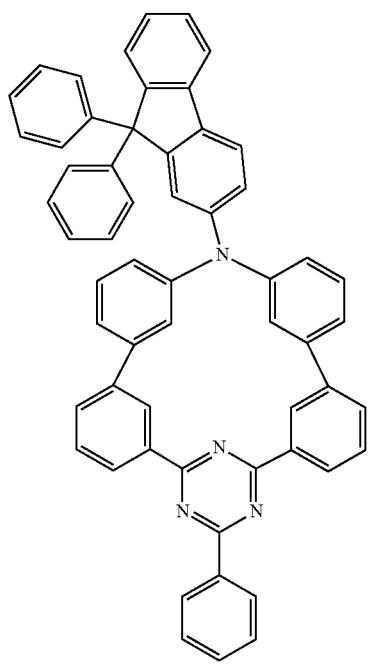

-continued

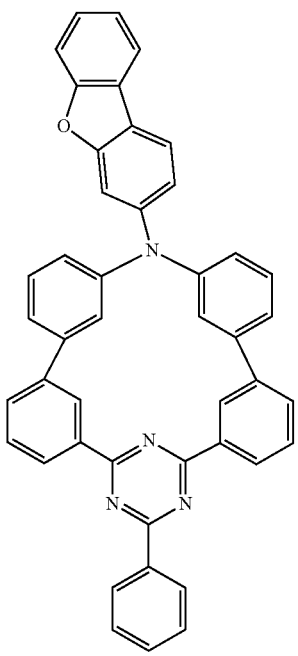

-continued
5
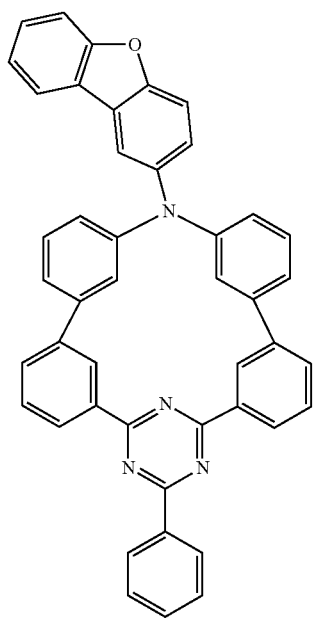
6
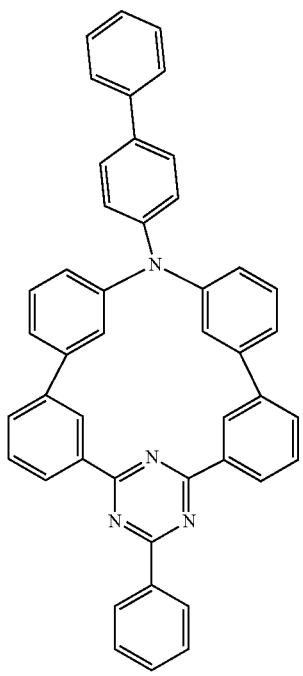
7
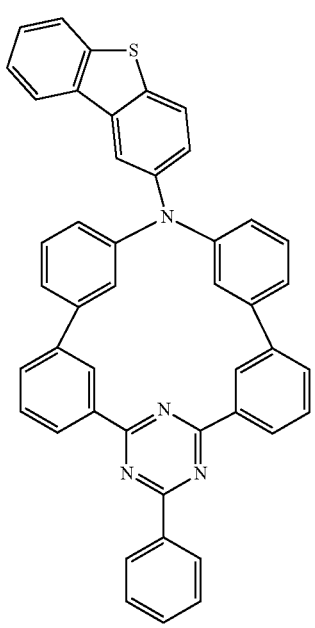
8

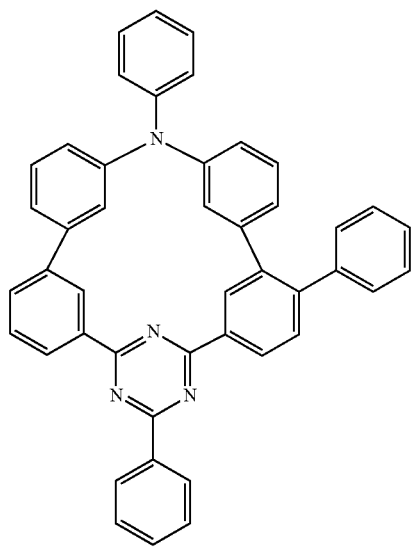
9
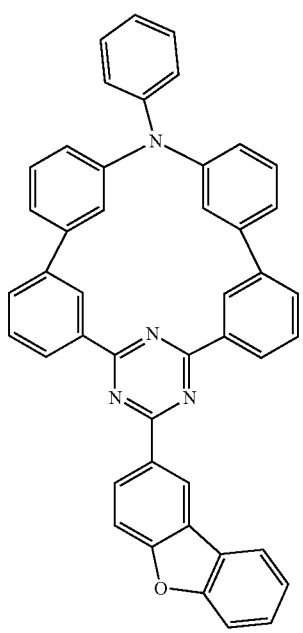
10
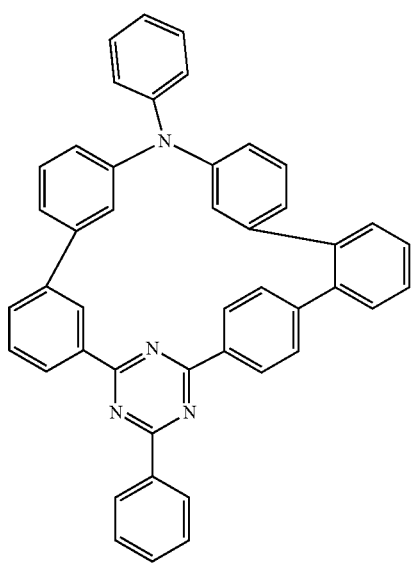
11
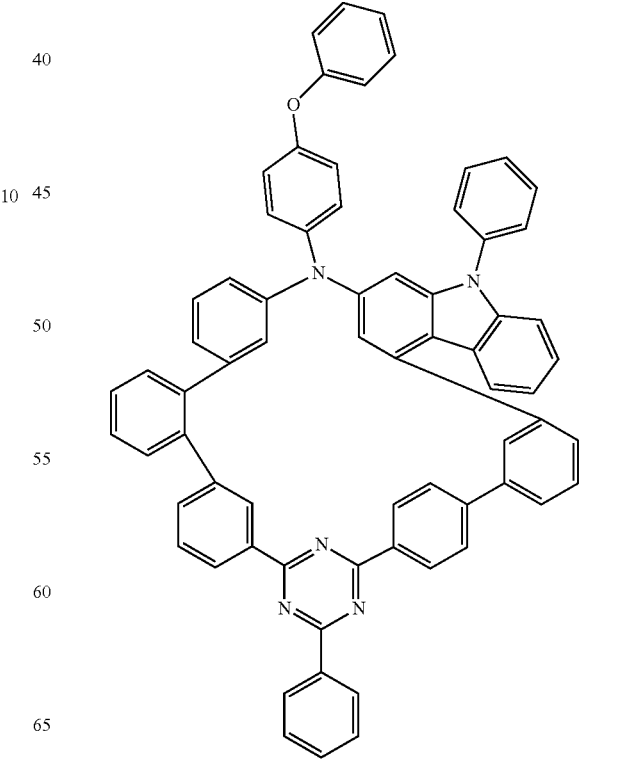
12

13
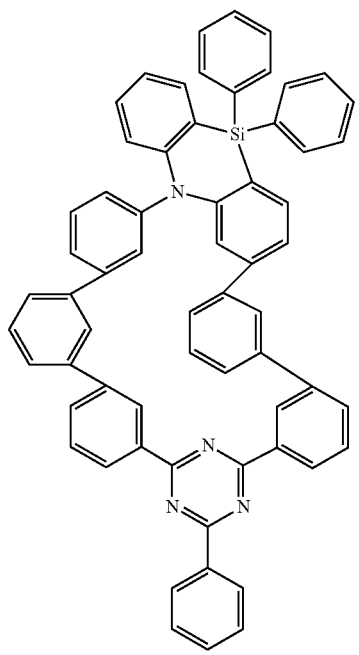
14
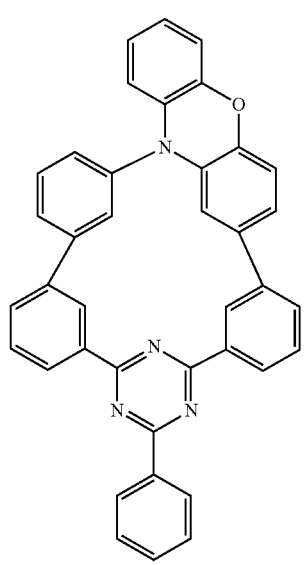
15
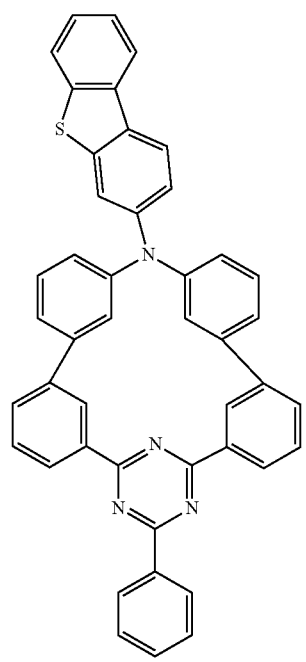
16
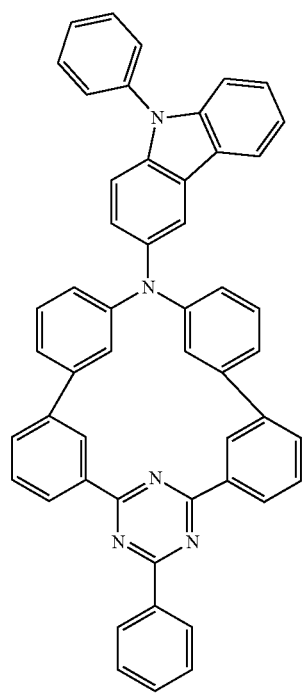

17
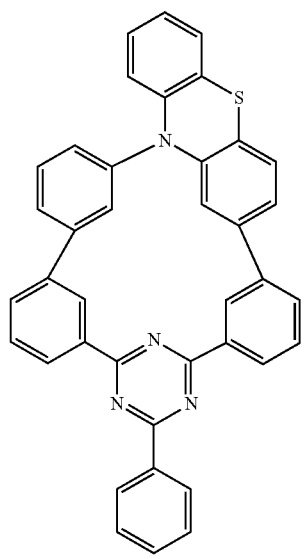
18
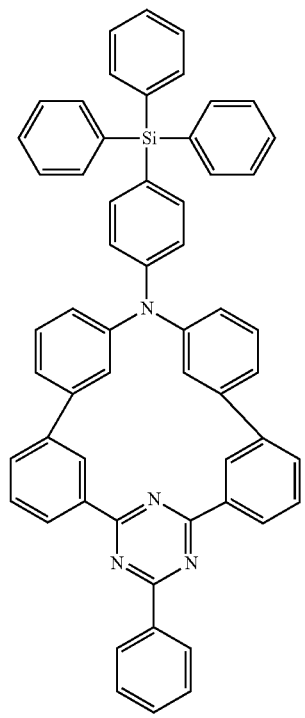
19
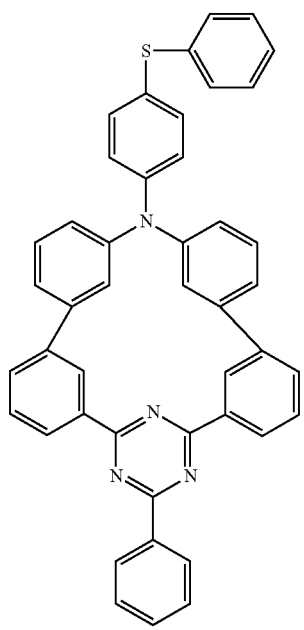
20
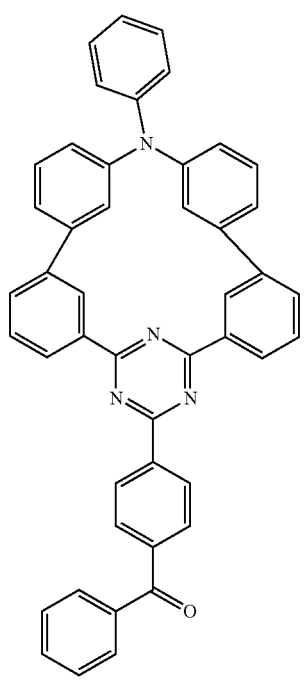

21
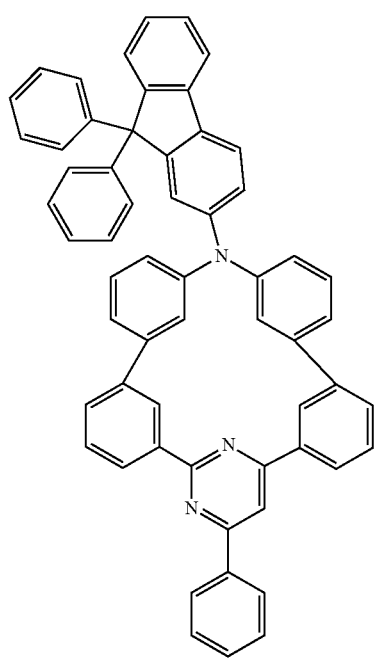
22
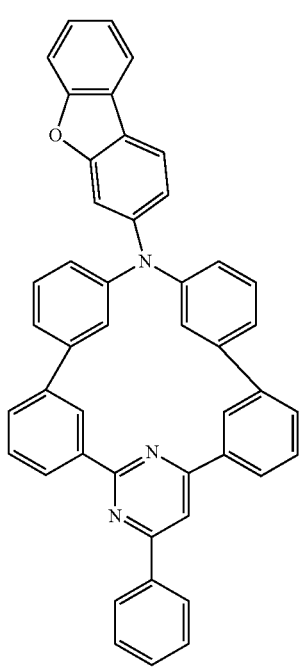
23
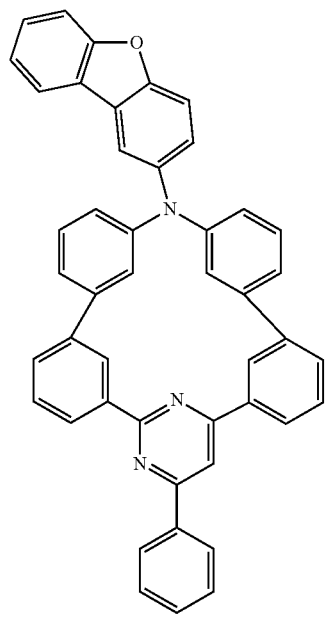
24
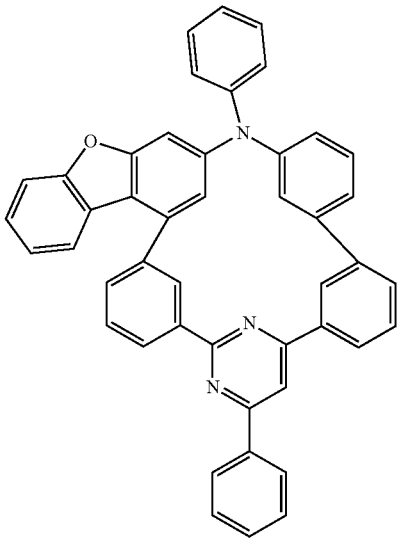

25
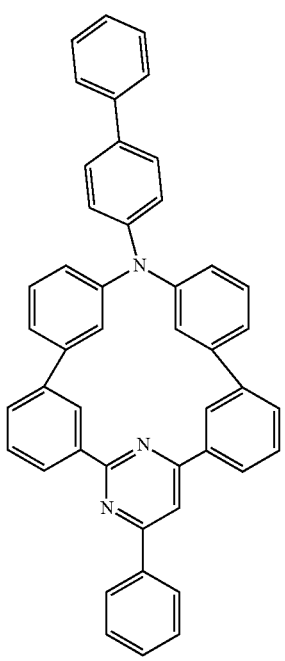
26
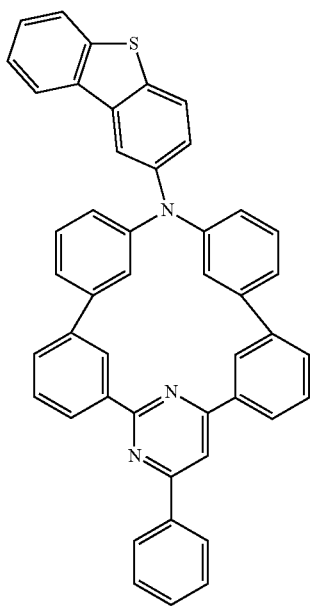
27
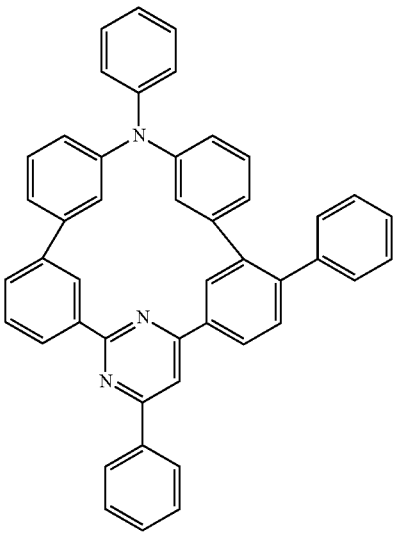
28
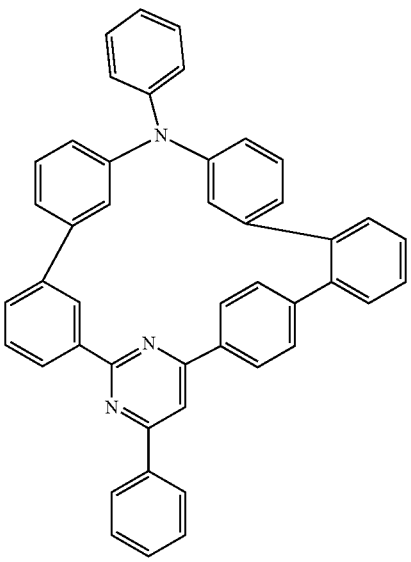

-continued
29
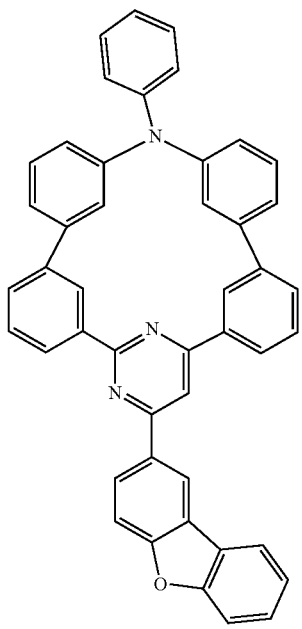
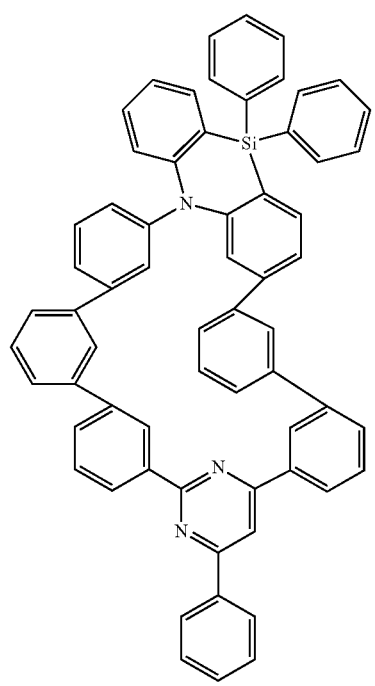
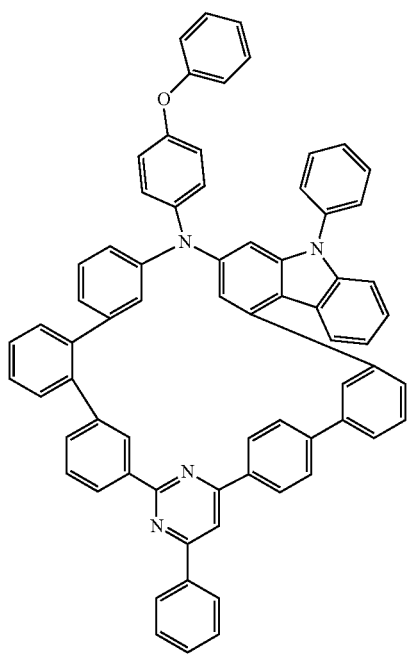
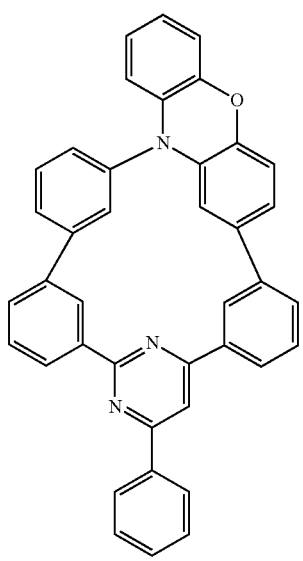

33
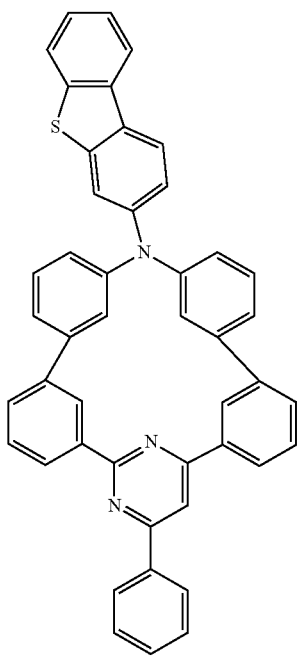
41
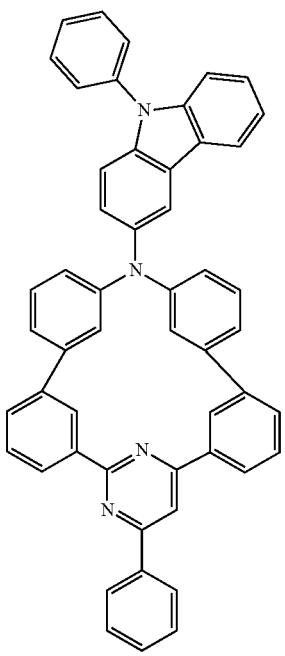
34
35
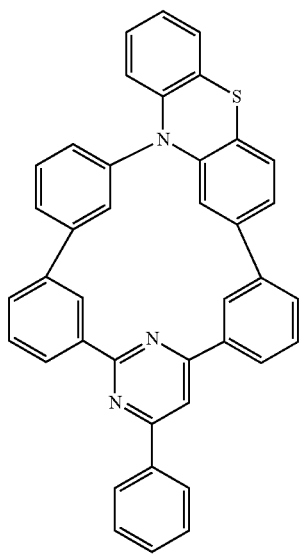
42
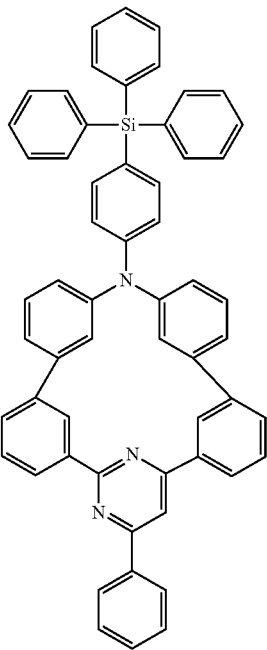
36

-continued

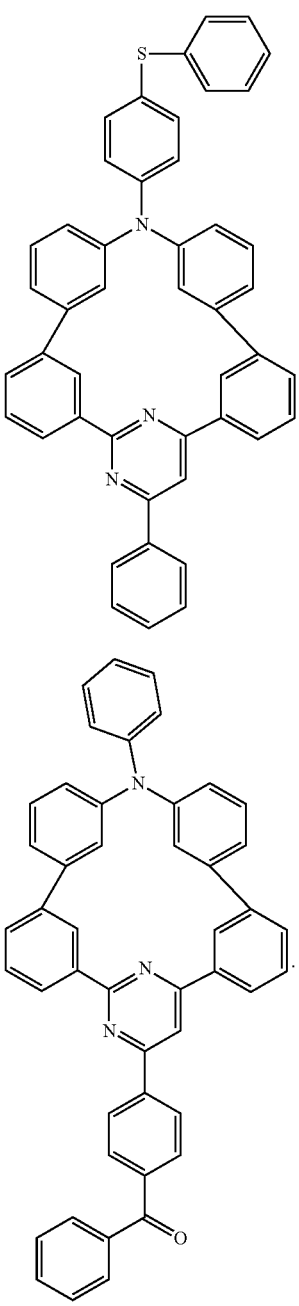

BRIEF DESCRIPTION OF THE DRAWINGS

The accompanying drawings are included to enable a further understanding of the present disclosure, and are incorporated in and constitute a part of this specification. The drawings illustrate example embodiments of the present disclosure and, together with the description, serve to explain principles of the present disclosure. In the drawings.

DETAILED DESCRIPTION

Figure 1:
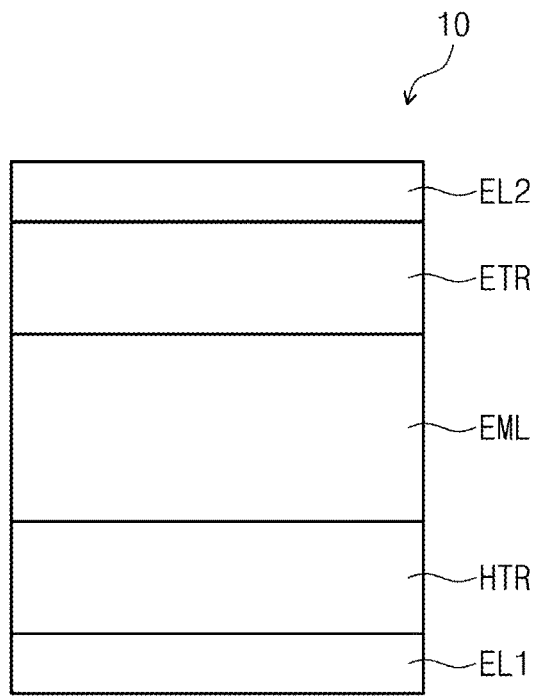
FIG. 1 is a cross-sectional view schematically illustrating an organic electroluminescence device according to an embodiment of the present disclosure.

Aspects of the present disclosure may have various modifications and may be embodied in different forms, and example embodiments will be explained in detail with reference to the accompany drawings. The present disclosure may, however, be embodied in different forms and should not be construed as being limited to the embodiments set forth herein. Rather, all modifications, equivalents, and substituents which are included in the spirit and technical scope of the present disclosure are understood to be included in the present disclosure.

Like reference numerals refer to like elements throughout, and duplicative descriptions thereof may not be provided. In the drawings, the dimensions of structures, layers, films, panels, regions, etc., may be exaggerated for clarity of illustration. It will be understood that, although the terms first, second, etc. may be used herein to describe various elements, these elements should not be limited by these terms. These terms are only used to distinguish one element from another element. Thus, a first element could be alternatively termed a second element without departing from the teachings of the present disclosure. Similarly, a second element could be alternatively termed a first element. As used herein, the singular forms are intended to include the plural forms as well, unless the context clearly indicates otherwise.

It will be further understood that the terms "comprises" and/or "comprising," when used in this specification, specify the presence of stated features, numerals, steps, operations, elements, parts, or the combination thereof, but do not preclude the presence or addition of one or more other features, numerals, steps, operations, elements, parts, or the combination thereof. It will also be understood that when a layer, a film, a region, a plate, etc. is referred to as being 'on' another part, it can be "directly on" the other part, or intervening layers may also be present. In contrast, when an element is referred to as being "directly on" another element, no intervening elements are present.

Expressions such as "at least one of", "one of", "selected from", "at least one selected from", and "one selected from", when preceding a list of elements, modify the entire list of elements and do not modify the individual elements of the list.

In the description, -* refers to a connecting position.

In the description, the term "substituted or unsubstituted" refers to the options of being unsubstituted, or substituted with at least one substituent selected from the group consisting of a deuterium atom, a halogen atom, a cyano group, a nitro group, an amino group, a silyl group, a boron group, a phosphine oxide group, a phosphine sulfide group, an alkyl group, an alkenyl group, an aryl group, and a heterocyclic group. In addition, each of the substituents may themselves be substituted or unsubstituted. For example, a biphenyl group may be interpreted as an aryl group, or may be alternatively referred to as a phenyl group substituted with a phenyl group.

In the description, references to a halogen atom may include a fluorine atom, a chlorine atom, a bromine atom, and an iodine atom.

In the description, an alkyl group may be a linear, branched or cyclic type or kind of alkyl group. The carbon number of the alkyl (e.g., the number of carbon atoms included in the alkyl group) may be 1 to 50, 1 to 30, 1 to 20, 1 to 10, or 1 to 6. Non-limiting examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, c-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc.

In the description, an aryl group may be a functional group or substituent derived from or including an aromatic hydrocarbon ring. The aryl group may be a monocyclic aryl group or a polycyclic aryl group. The carbon number for forming a ring in the aryl group (e.g., the number of carbons included in the aryl group ring) may be 6 to 30, 6 to 20, or 6 to 15. Non-limiting examples of the aryl group may include phenyl, naphthyl, fluorenyl, anthracenyl, phenanthryl, biphenyl, terphenyl, quaterphenyl, quinqphenyl, sexiphenyl, triphenylene, pyrenyl, benzofluoranthenyl, chrysenyl, etc.

In the description, the fluorenyl group may be substituted (e.g., at the 9 carbon position), and the two substituents may be combined with each other to form a spiro structure.

In the description, the heteroaryl group may be a heteroaromatic group including at least one of O, N, P, Si, or S as a heteroatom. The carbon number for forming a ring of the heteroaryl group (e.g., the number of carbons included in the heteroaryl group ring) may be 2 to 30, or 2 to 20. The heteroaryl group may be a monocyclic heteroaryl group or a polycyclic heteroaryl group. For example, the polycyclic heteroaryl group may have a bicyclic structure or a tricyclic structure. Non-limiting examples of the heteroaryl group may include thiophene, furan, pyrrole, imidazole, thiazole, oxazole, oxadiazole, triazole, pyridine, bipyridine, pyrimidine, triazine, acridine, pyridazine, pyrazine, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzimidazole, benzothiazole, benzocarbazole, benzothiophene, dibenzothiophene, thienothiophene, benzofuran, phenanthroline, thiazole, isooxazole, oxadiazole, thiadiazole, phenothiazine, dibenzosilole, dibenzofuran, etc.

In the description, a silyl group may be an alkylsilyl group or an arylsilyl group. Non-limiting examples of the silyl group may include a trimethyl silyl group, a triethylsilyl group, a t-butyldimethylsilyl group, a vinyldimethylsilyl group, a propyldimethylsilyl group, a triphenylsilyl group, a diphenylsilyl group, a phenylsilyl group, etc.

In the description, a boron group may be an alkyl boron group or an aryl boron group. Non-limiting examples of the boron group may include a trimethyl boron group, a triethylboron group, a t-butyldimethylboron group, a triphenylboron group, a diphenylboron group, a phenylboron group, etc.

In the description, an alkenyl group may be linear or branched. The carbon number of the alkenyl group is not specifically limited, and may be 2 to 30, 2 to 20, or 2 to 10. Non-limiting examples of the alkenyl group may include vinyl, 1-butenyl, 1-pentenyl, 1,3-butadienyl aryl, styrenyl, styrylvinyl, etc.

Hereinafter, the nitrogen-containing compound according to an embodiment of the present disclosure will be explained.

The nitrogen-containing compound according to an embodiment of the present disclosure may be represented by Formula 1:

Formula 1

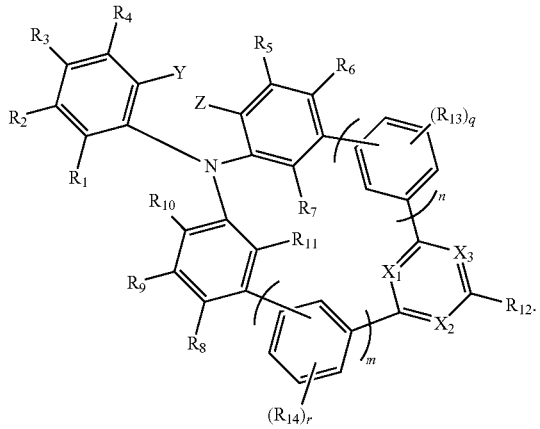

In Formula 1, at least two of $X_1$, $X_2$ or $X_3$ may be N, and the remainder thereof may be $CR_{15}$. Y and Z may each independently be a hydrogen atom, a deuterium atom, $OR_{16}$, $SR_{17}$, $CR_{18}R_{19}R_{20}$, or $SiR_{21}R_{22}R_{23}$, or may be combined with (e.g., linked to) each other to form a ring. In Formula 1, $R_1$ to $R_{14}$ may each independently be a hydrogen atom, a deuterium atom, $OR_{24}$, $SR_{25}$, $(C=O)R_{26}$, $NR_{27}R_{28}$, $CR_{29}R_{30}R_{31}$, $SiR_{32}R_{33}R_{34}$, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, or may be combined with (e.g., linked to) an adjacent group to form a ring. In addition, $R_{15}$ to $R_{34}$ may each independently be a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, or may be combined with (e.g., linked to) an adjacent group to form a ring.

In Formula 1, n and m may each independently be 1 or 2, and q and r may each independently be an integer of 0 to 4.

The nitrogen-containing compound according to an embodiment of the present disclosure, as represented by Formula 1 may have a cyclic molecular structure including a nitrogen atom in a ring. The nitrogen-containing compound according to an embodiment of the present disclosure may be a compound having a cyclic molecular structure including an aryl amine group and an azine group including two or three nitrogen atoms in its aromatic ring. In the cyclic nitrogen-containing compound according to an embodiment of the present disclosure, a plurality of substituted or unsubstituted arylene groups may be positioned between the aryl amine group nitrogen atom and the azine group. The substituted or unsubstituted arylene group(s) may be (a) linker(s) connecting the aryl amine group nitrogen atom and the azine group.

In the nitrogen-containing compound according to an embodiment of the present disclosure, as represented by Formula 1, the moiety

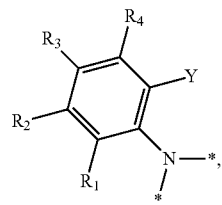

corresponding to the aryl amine group, may be or act as an electron donor, and the moiety

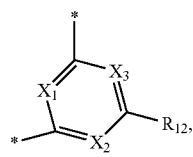

corresponding to the azine group, may be or act as an electron acceptor. However, embodiments of the present disclosure are not limited thereto.

In Formula 1, Y and Z may each independently be a hydrogen atom, a deuterium atom, $OR_{16}$, $SR_{17}$, $CR_{18}R_{19}R_{20}$, or $SiR_{21}R_{22}R_{23}$. In some embodiments, for example, Y and Z may both (e.g., simultaneously) be a hydrogen atom. In addition, $R_{16}$ to $R_{23}$ may each independently be a substituted or unsubstituted phenyl group.

In some embodiments, when Y and Z are each independently $CR_{18}R_{19}R_{20}$ or $SiR_{21}R_{22}R_{23}$, two neighboring substituents among $R_{18}$, $R_{19}$, and $R_{20}$ may be combined with (e.g., linked to) each other to form a ring, or two neighboring substituents among $R_{21}$, $R_{22}$, and $R_{23}$ may be combined with (e.g., linked to) each other to form a ring. In addition, Y and Z may be combined with (e.g., linked to) each other to form a ring. For example, the neighboring substituents of Y and Z may be combined with each other to form a heterocycle.

$R_1$ to $R_{14}$ of Formula 1 may each independently be a hydrogen atom, a deuterium atom, $OR_{24}$, $SR_{25}$, $(C=O)R_{26}$, $NR_{27}R_{28}$, $CR_{29}R_{30}R_{31}$, $SiR_{32}R_{33}R_{34}$, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring. For example, $R_1$ to $R_{14}$ may be each independently a hydrogen atom, $OR_{24}$, $SR_{25}$, $(C=O)R_{26}$, $NR_{27}R_{28}$, $CR_{29}R_{30}R_{31}$, $SiR_{32}R_{33}R_{34}$, or a substituted or unsubstituted phenyl group.

In some embodiments, $R_{24}$ to $R_{34}$ may be combined with neighboring substituents to form a ring. In some embodiments, for example, $R_{24}$ to $R_{34}$ may each independently be a hydrogen atom, a substituted or unsubstituted alkyl group having 1 to 20 carbon atoms, or a substituted or unsubstituted aryl group having 6 to 30 carbon atoms for forming a ring. For example, $R_{24}$ to $R_{34}$ may each independently be a hydrogen atom, a methyl group, or a phenyl group.

In some embodiments, in $R_1$ to $R_{14}$ in Formula 1, adjacent substituents may be combined with (e.g., linked to) each other to form a ring. For example, in $R_1$ to $R_{14}$, adjacent substituents may be combined with (e.g., linked to) each other to form a substituted or unsubstituted fluorene, a substituted or unsubstituted dibenzothiophene, a substituted or unsubstituted dibenzofuran, or a substituted or unsubstituted carbazole.

In Formula 1, $R_{12}$ may be a substituted or unsubstituted phenyl group. In some embodiments, for example, $R_{12}$ may be an unsubstituted phenyl group. In some embodiments, $R_{12}$ may be a substituted or unsubstituted dibenzofuran group, for example, $R_{12}$ may be an unsubstituted dibenzofuran group.

In some embodiments, in Formula 1, q and r may each independently an integer of 0 to 4. When q and r are each an integer of 2 or more, a plurality of $R_{13}$ and a plurality of $R_{14}$ may each independently be the same or different.

In Formula 1, at least two of $X_1$ to $X_3$ may be N. In some embodiments, for example, $X_1$ may be N, and at least one of $X_2$ or $X_3$ may be N. In some embodiments, $X_1$ and $X_2$ may be N, and $X_3$ may be $CR_{15}$; $X_1$ and $X_3$ may be N and $X_2$ may be $CR_{15}$; or all $X_1$ to $X_3$ may be N. For example, in Formula 1, the heterocycle including $X_1$ to $X_3$ may be pyrimidine or triazine.

In Formula 1, when two of $X_1$ to $X_3$ are N, and the remainder is $CR_{15}$, $R_{15}$ may be a hydrogen atom, a deuterium atom, $OR_{24}$, $SR_{25}$, $CR_{26}R_{27}R_{28}$, $SiR_{29}R_{30}R_{31}$, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring. In some embodiments, $R_{15}$ may be a hydrogen atom.

In some embodiments, the nitrogen-containing compound represented by Formula 1 may be further represented by Formula 1-1 or Formula 1-2. Formula 1-1 corresponds to a case where $X_1$ and $X_2$ are N, and Formula 1-2 corresponds to a case where all of $X_1$ to $X_3$ are N:

Formula 1-1

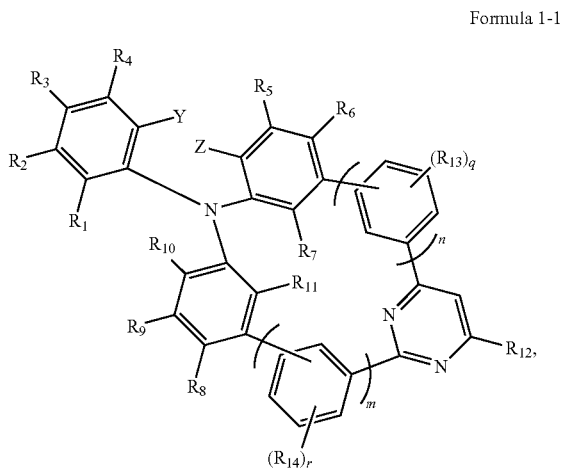

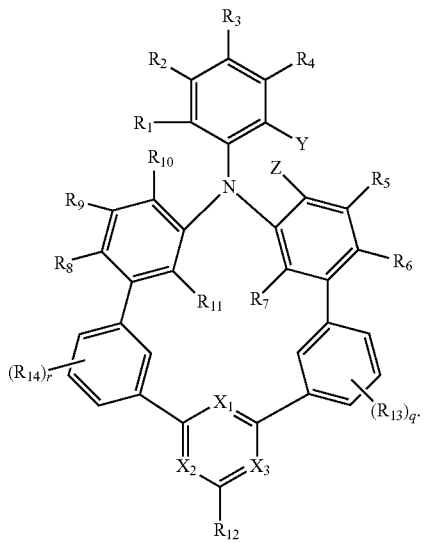

Formula 1-2

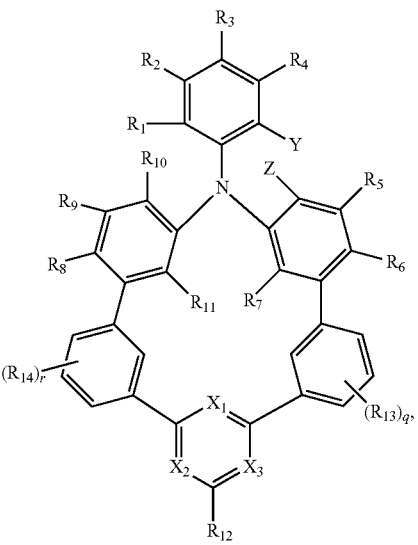

Formula 1-3

In Formula 1-1 and Formula 1-2, Y, Z, n, m, $R_1$ to $R_{34}$, q9, and r may each independently be the same as defined in Formula 1.

In the nitrogen-containing compound according to an embodiment of the present disclosure, as represented by Formula 1, n and m may each independently be 1 to 2. In some embodiments, for example, both n and m may be 1 (e.g., simultaneously), or one of n and m may be 1 and the remainder thereof may be 2, or both n and m may be 2.

In Formula 1, when both n and m are 1, the nitrogen-containing compound according to an embodiment of the present disclosure may be a cyclic compound including five connected rings. In addition, when one of n and m is 1 and the other is 2, the nitrogen-containing compound according to an embodiment of the present disclosure may be acyclic compound including six connected rings, and when both n and m are 2, the nitrogen-containing compound according to an embodiment of the present disclosure may be a cyclic compound including seven connected rings.

In some embodiments, the nitrogen-containing compound represented by Formula 1 may be further represented by Formula 1-3 or Formula 1-4. Formula 1-3 corresponds to a case where both n and m are 1, and Formula 1-4 represents a case where both n and m are 2:

Formula 1-4

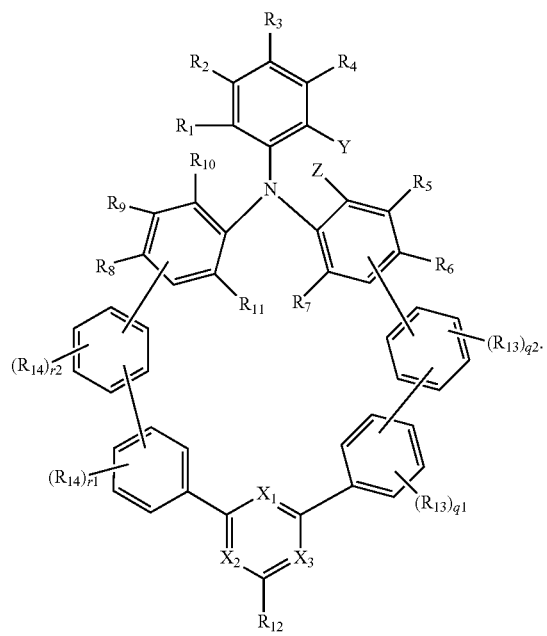

In Formula 1-3 and Formula 1-4, q1, q2, r1, and r2 may each independently be an integer of 0 to 4. In addition, in Formula 1-3 and Formula 1-4, $X_1$ to $X_3$, Y, Z, $R_1$ to $R_{34}$, q, and r may each independently be the same as defined in Formula 1.

In Formula 1-3 and Formula 1-4, when q1, q2, r1, and r2 are each independently an integer of 2 or more, the plurality of $R_{13}$ and the plurality of $R_{14}$ may each independently be the same or different.

In some embodiments, the nitrogen-containing compound represented by Formula 1 may be further represented by Formula 1-5 or Formula 1-6. Formula 1-5 corresponds to a case where both n and m are 1 (e.g., simultaneously), and Formula 1-6 corresponds to the case where both n and m are 2. Formula 1-5 corresponds to a case where q and r are both 0, and Formula 1-6 corresponds to a case where all of q1, q2, r1, and r2 are 0. In addition, Formula 1-5 and Formula 1-6 correspond to a case where both $R_7$ and $R_{11}$ are hydrogen atoms.

The nitrogen-containing compound according to an embodiment of the present disclosure, as represented by Formula 1, may be one of the compounds represented in Compound Group 1:

Compound Group 1

Formula 1-5

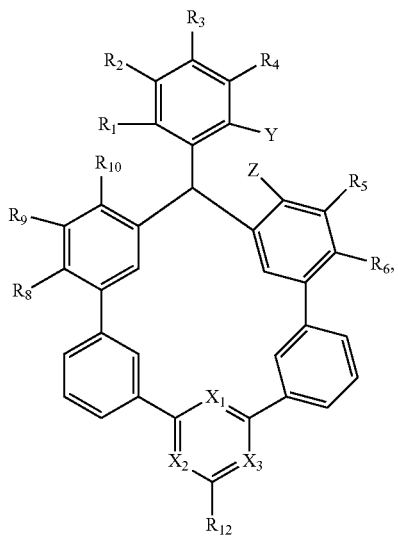

Formula 1-6

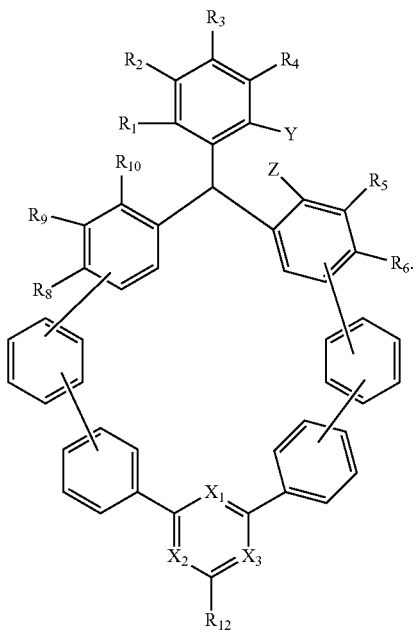

In Formula 1-5 and Formula 1-6, $X_1$ to $X_3$, Y, Z, $R_1$ to $R_6$, $R_8$, $R_9$, $R_{10}$, and $R_{12}$ may each independently be the same as defined in Formula 1.

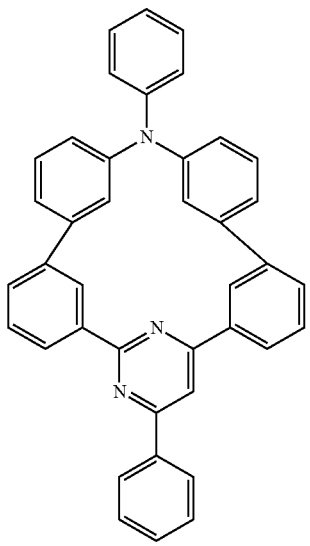

1

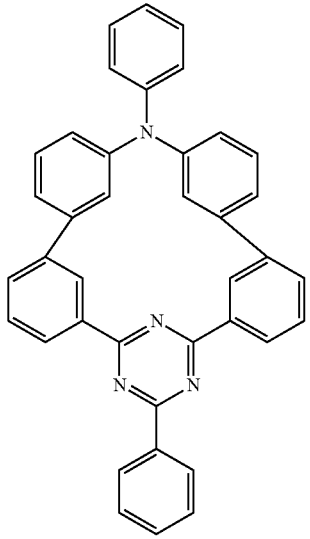

2

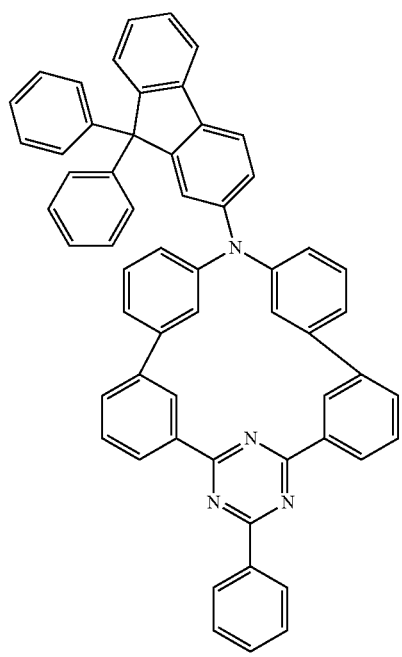
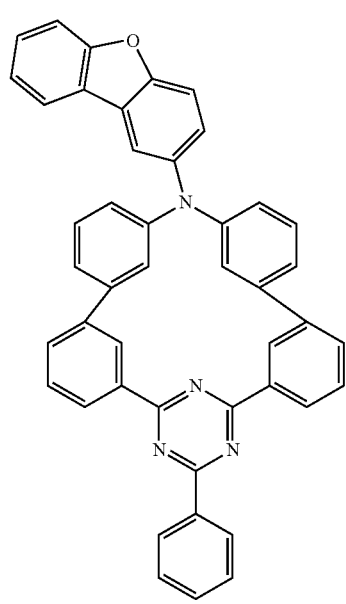
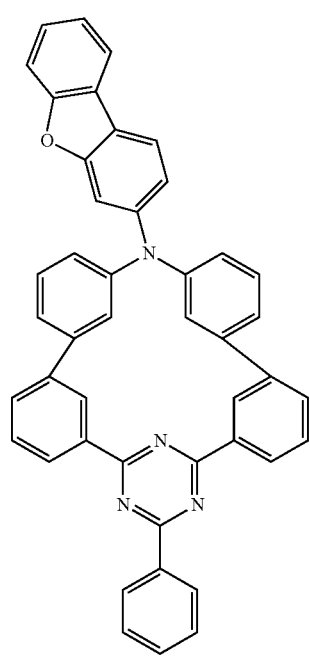
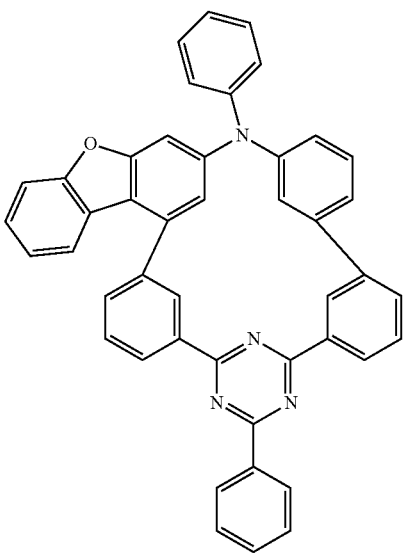

7
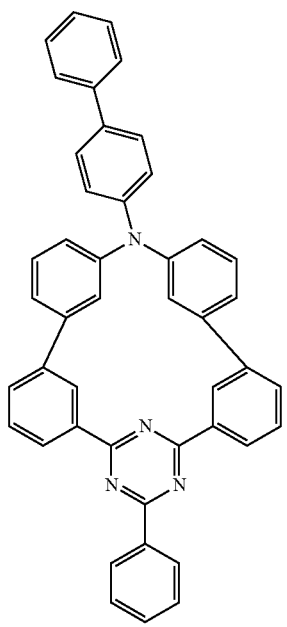
5
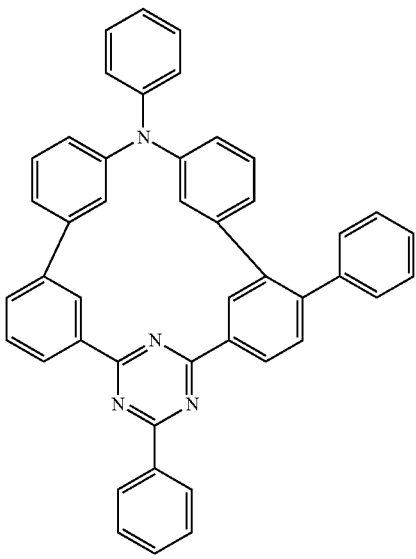
8
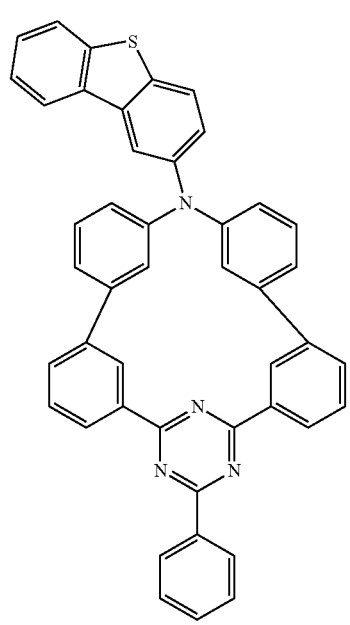
10
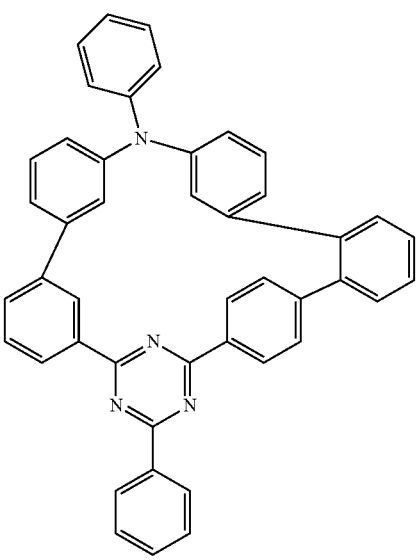

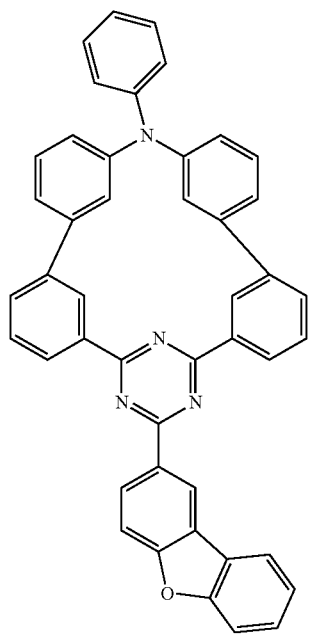
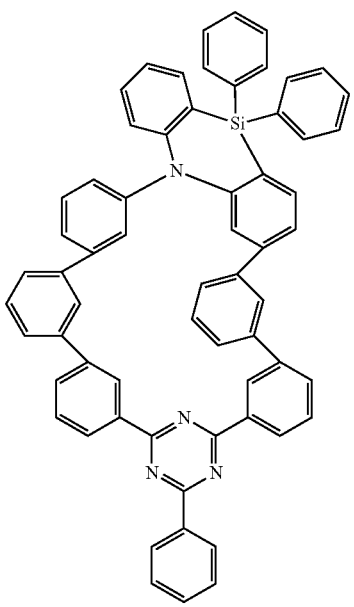

15
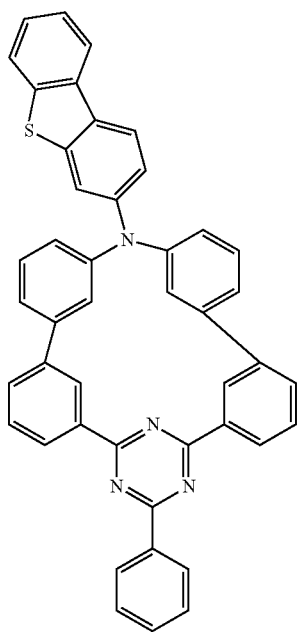
16
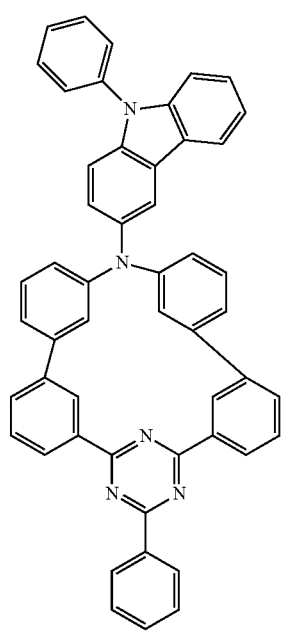
17
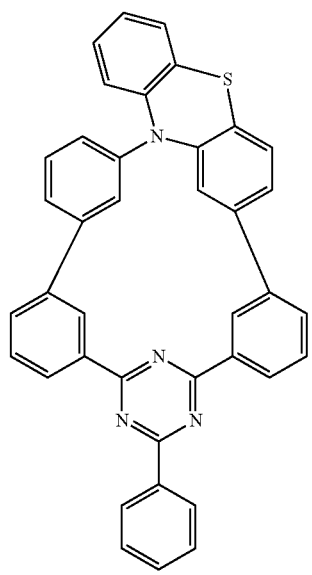
18
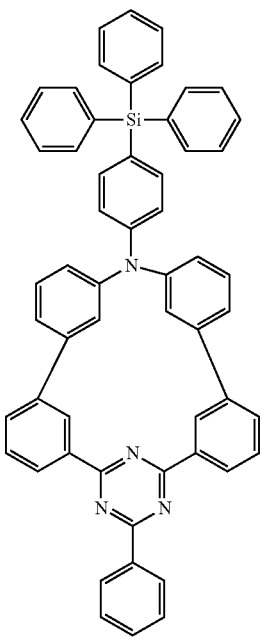

19
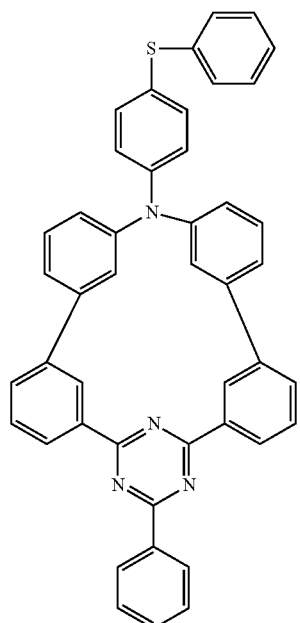
20
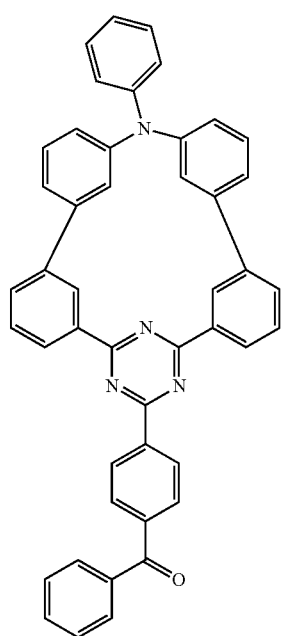
21
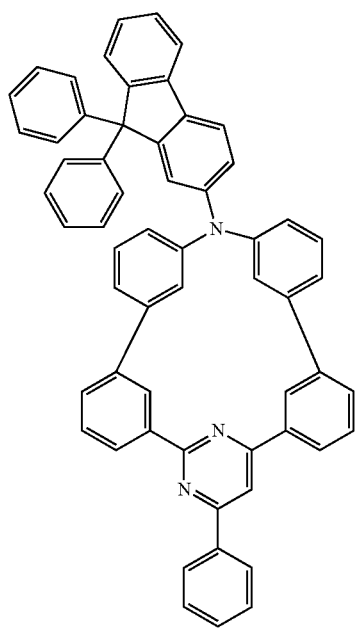
22
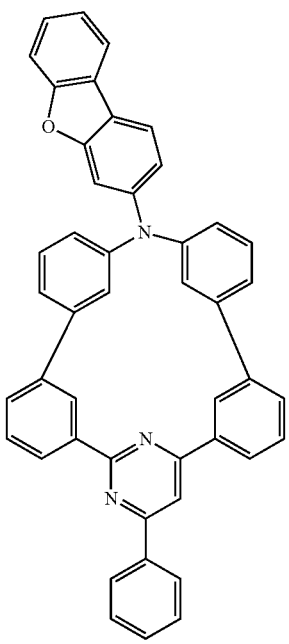

23
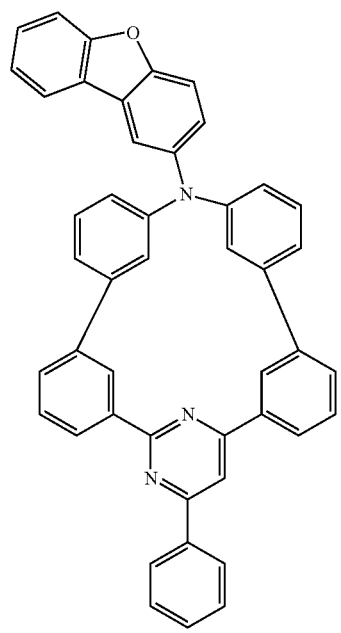
24
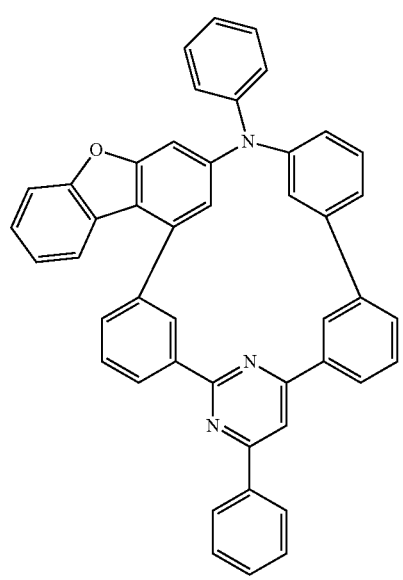
25
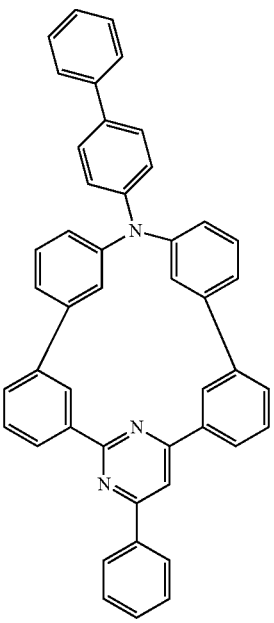
26
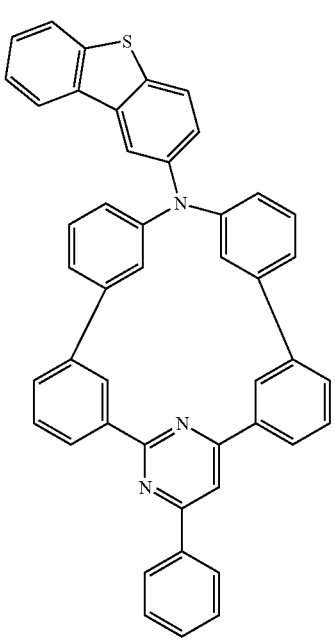

27
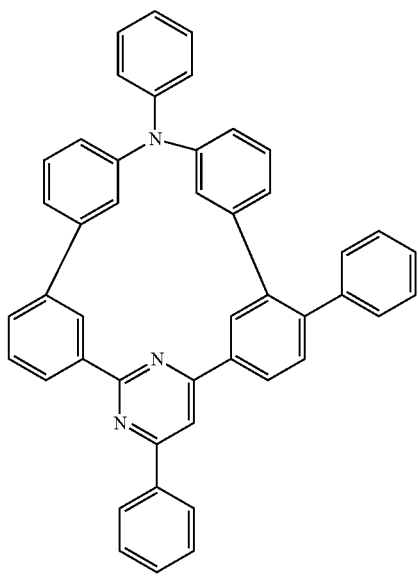
28
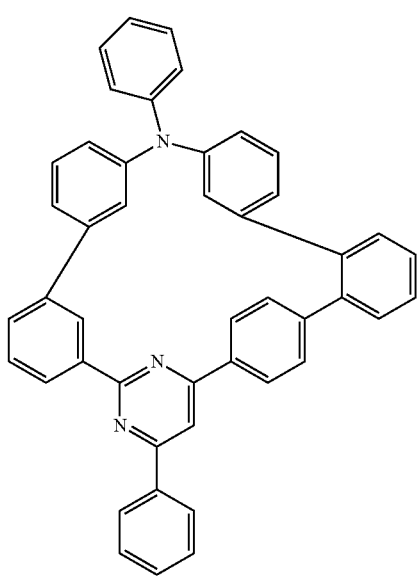
29
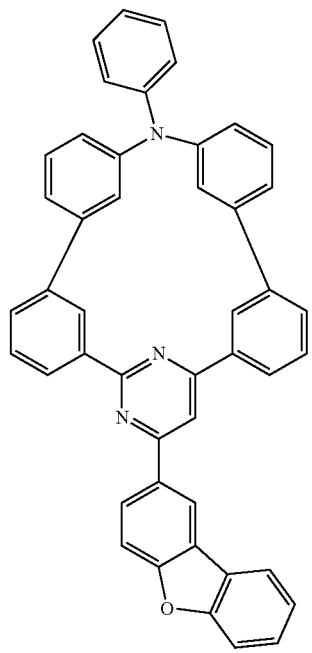
30
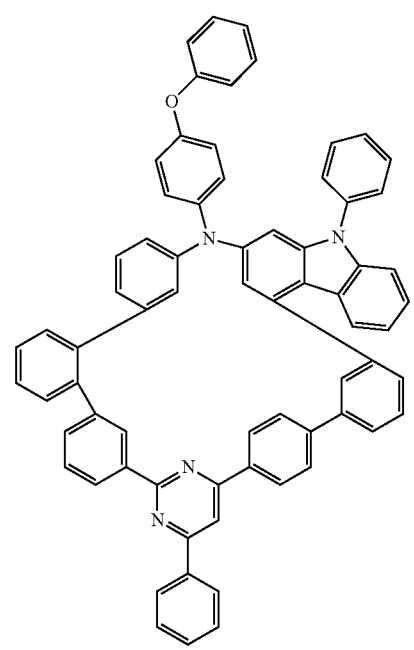

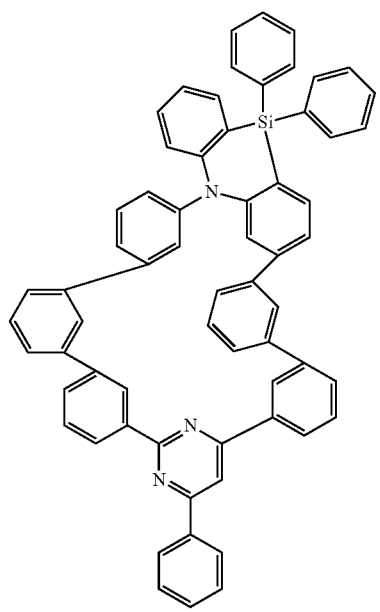
31
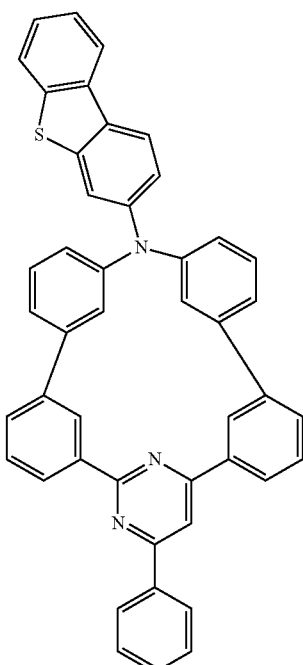
33
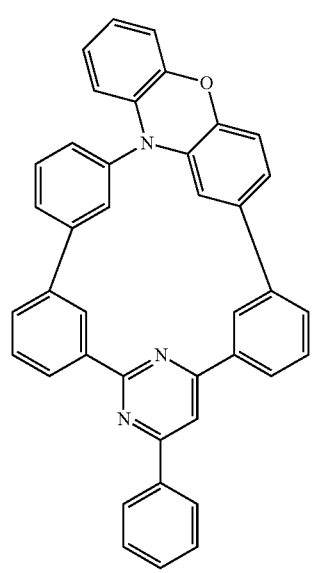
32
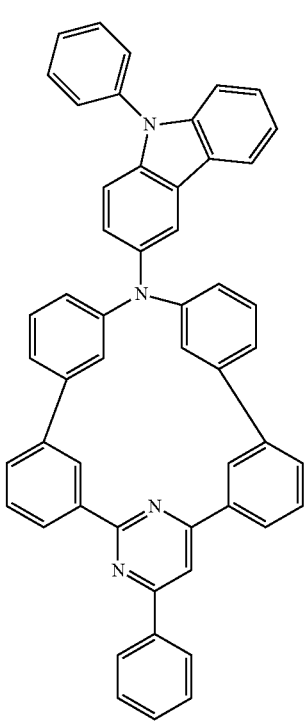
34

35

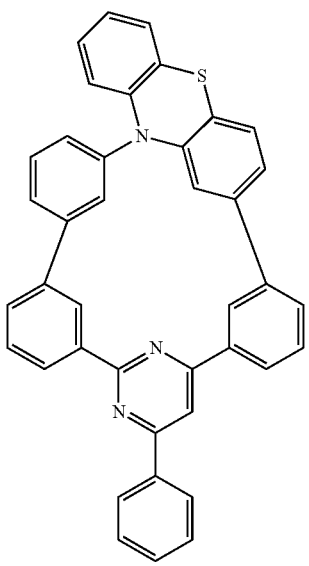

36

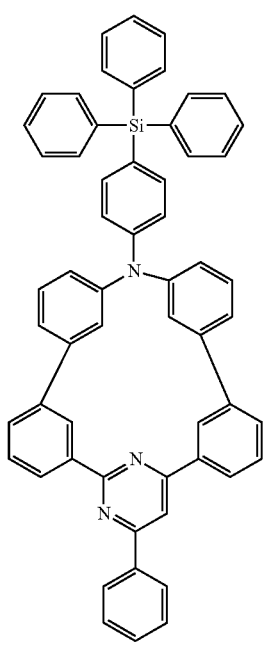

37

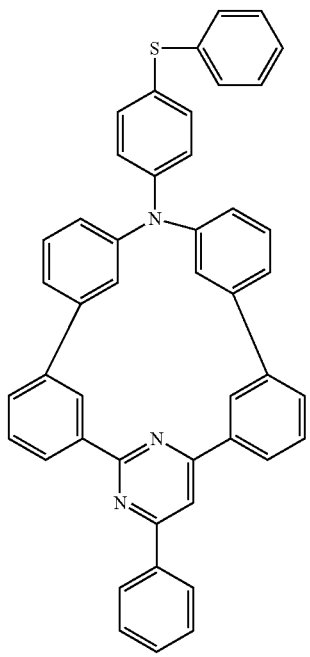

38

The nitrogen-containing compound according to an embodiment of the present disclosure may have a cyclic molecular structure, in which a plurality of aromatic rings are connected with each other, and the compound may have excellent heat resistance and/or chemical resistance. In addition, the nitrogen-containing compound according to an embodiment of the present disclosure may include an aryl amine group that acts as an electron donating group and an azine group that acts as an electron accepting group in the cyclic molecular structure, and as such, a light-emitting material having a small energy difference between the lowest excitation singlet energy level (S1) and the lowest excitation triplet energy level (T1) may be attained.

The nitrogen-containing compound according to an embodiment of the present disclosure may have a single-triplet energy difference ($\Delta E_{ST}$) between the lowest excitation singlet energy level (S1) and the lowest excitation triplet energy level (T1) of about 0.2 eV or less. The nitrogen-containing compound according to an embodiment of the present disclosure may be utilized as a material for emitting delayed fluorescence. In some embodiments, the nitrogen-containing compound may have a small $\Delta E_{ST}$ value, and may be utilized as a material for thermally activated delayed fluorescence (TADF).

The nitrogen-containing compound according to an embodiment of the present disclosure may be utilized in an organic electroluminescence device, and may thereby improve the emission efficiency of the organic electroluminescence device. The nitrogen-containing compound according to an embodiment of the present disclosure may be utilized as a material in an emission layer that is positioned between opposite electrodes of an organic electroluminescence device. In some embodiments, the nitrogen-containing compound according to an embodiment of the present disclosure may be included in an emission layer as a thermally activated delayed fluorescence dopant to further improve the emission efficiency of an organic electroluminescence device, for example, in an emission layer to emit blue light to further improve emission efficiency.

Hereinafter, an organic electroluminescence device according to an embodiment of the present disclosure will be explained in further detail. References to the above-described nitrogen-containing compound according to an embodiment of the present disclosure will be understood in the context of the above description of the nitrogen-containing compound according to an embodiment of the present disclosure.

Figure 2:
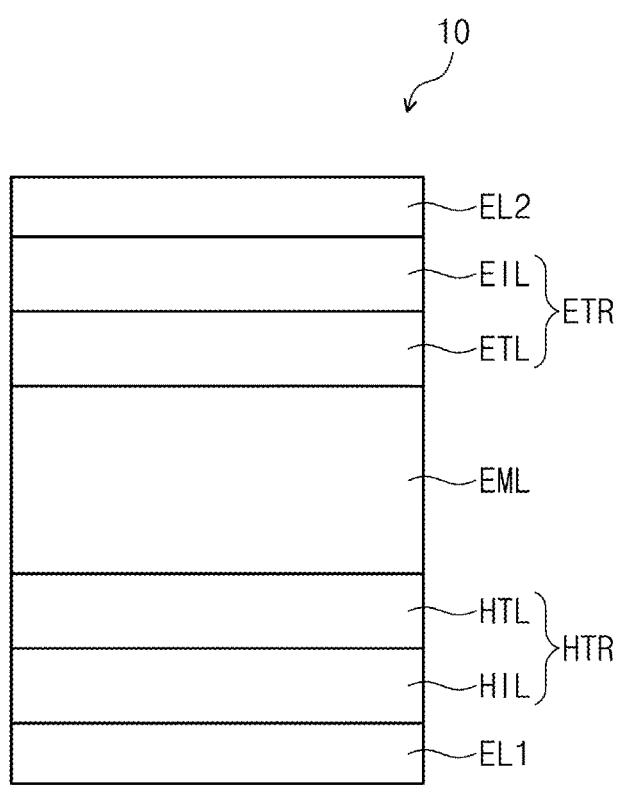
FIG. 2 is a cross-sectional view schematically illustrating an organic electroluminescence device according to an embodiment of the present disclosure.
Figure 3:
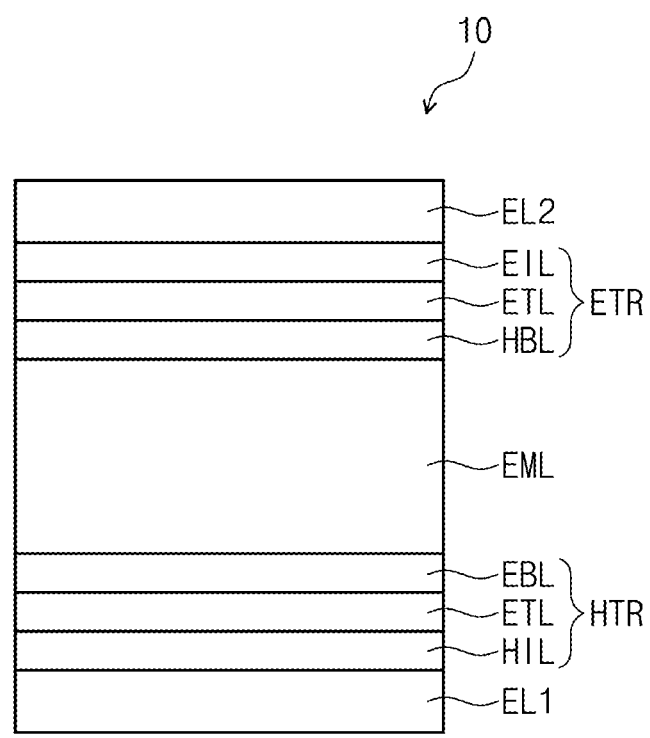
FIG. 3 is a cross-sectional view schematically illustrating an organic electroluminescence device according to an embodiment of the present disclosure.

FIGS. 1 to 3 are cross-sectional views schematically illustrating organic electroluminescence devices according to one or more example embodiments of the present disclosure. Referring to FIGS. 1 to 3, an organic electroluminescence device 10 according to an embodiment of the present disclosure may include a first electrode EL1, a hole transport region HTR, an emission layer EML, an electron transport region ETR, and a second electrode EL2, which may be laminated one by one (e.g., stacked in the stated order).

The first electrode EL1 and the second electrode EL2 may be oppositely positioned from each other (e.g., may be on opposite ends of the layer stack along a thickness direction in the device 10), and a plurality of organic layers may be positioned between the first electrode EL1 and the second electrode EL2. The plurality of the organic layers may include the hole transport region HTR, the emission layer EML, and the electron transport region ETR. The organic electroluminescence device 10 according to an embodiment of the present disclosure may include the nitrogen-containing compound according to an embodiment of the present disclosure in the emission layer EML.

FIG. 2 shows a cross-sectional view of an organic electroluminescence device according to an embodiment of the present disclosure, wherein the hole transport region HTR includes a hole injection layer HIL and a hole transport layer HTL, and the electron transport region ETR includes an electron injection layer EIL and an electron transport layer ETL. FIG. 3 shows a cross-sectional view of an organic electroluminescence device 10 according to an embodiment of the present disclosure, wherein the hole transport region HTR includes a hole injection layer HIL, a hole transport layer HTL, and an electron blocking layer EBL, and the electron transport region ETR includes an electron injection layer EIL, an electron transport layer ETL, and a hole blocking layer HBL.

The first electrode EL1 may have conductivity (e.g., may be conductive). The first electrode EL1 may be formed using a metal alloy and/or a conductive compound. In some embodiments, the first electrode EL1 may be an anode.

The first electrode EL1 may be a transmissive electrode, a transflective electrode, or a reflective electrode. When the first electrode EL1 is a transmissive electrode, the first electrode EL1 may be formed using a transparent metal oxide, for example, indium tin oxide (ITO), indium zinc oxide (IZO), zinc oxide (ZnO), indium tin zinc oxide (ITZO), etc. When the first electrode EL1 is a transflective electrode or a reflective electrode, the first electrode EL1 may include silver (Ag), magnesium (Mg), copper (Cu), aluminum (Al), platinum (Pt), palladium (Pd), gold (Au), nickel (Ni), neodymium (Nd), iridium (Ir), chromium (Cr), lithium (Li), calcium (Ca), LiF/Ca, LiF/Al, molybdenum (Mo), titanium (Ti), a compound thereof, or a mixture thereof (for example, a mixture of Ag and Mg). In some embodiments, the first electrode EL1 may have a structure of a plurality of layers including a reflective layer or a transflective layer formed using the above materials, and/or a transmissive conductive layer formed using ITO, IZO, ZnO, ITZO, etc. In some embodiments, the first electrode EL1 may include a plurality of layers of ITO/Ag/ITO.

The hole transport region HTR may be on the first electrode EL1. The hole transport region HTR may include at least one of a hole injection layer HIL, a hole transport layer HTL, a hole buffer layer, and/or an electron blocking layer.

The hole transport region HTR may have a single layer structure formed using a single material, a single layer structure formed using a plurality of different materials, or a multilayer structure including a plurality of layers formed using a plurality of different materials.

In some embodiments, for example, the hole transport region HTR may have a single layer structure including, for example, a hole injection layer HIL or a hole transport layer HTL, and the single layer may be formed using a hole injection material and a hole transport material. In some embodiments, the hole transport region HTR may have a single layer structure formed using a plurality of different materials, or a multi-layer laminated structure including a first electrode EL1 under one of: hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, without limitation.

The hole transport region HTR may be formed using one or more suitable methods, such as a vacuum deposition method, a spin coating method, a cast method, a Langmuir-Blodgett (LB) method, an inkjet printing method, a laser printing method, and/or a laser induced thermal imaging (LITI) method.

The hole injection layer HIL of the organic electroluminescence device 10 according to an embodiment of the present disclosure may include any suitable hole injection material. In some embodiments, for example, the hole injection layer HIL may include triphenylamine-containing polyetherketone (TPAPEK), 4-isopropyl-4'-methyldiphenyl-liodoniumtetrakis(pentafluorophenyl)borate (PPBL), N,N'-diphenyl-N,N'-bis-[4-(phenyl-m-tolyl-amino)-phenyl]-phenyl-4,4'-diamine (DNTPD), a phthalocyanine compound (such as copper phthalocyanine), 4,4',4"-tris(3-methylphenylphenylamino)triphenylamine (m-MTDATA), N,N'-di(1-naphthyl)-N,N'-diphenylbenzidine (NPB), N,N'-bis(1-naphthyl)-N,N'-diphenyl-4,4'-diamine (α-NPD), 4,4',4"-tris(N,N-diphenylamino)triphenylamine (TDATA), 4,4',4"-tris(N,N-2-naphthylphenylamino)triphenylamine (2-TNATA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), dipyrazino[2,3-f: 2',3'-h] quinoxaline-2,3,6,7,10,11-hexacarbonitrile (HAT-CN), etc. However, embodiments of the present disclosure are not limited thereto.

The hole transport layer HTL of the organic electroluminescence device 10 according to an embodiment of the present disclosure may include any suitable hole transport material. For example, the hole transport layer HTL may include 1,1-bis[(di-4-tolylamino)phenyl]cyclohexane (TAPC), a carbazole derivative (such as N-phenyl carbazole and/or polyvinyl carbazole), N,N'-bis(3-methylphenyl)-N,N'-diphenyl-[1,1-biphenyl]-4,4'-diamine (TPD), 4,4',4"-tris(N-carbazolyl)triphenylamine (TCTA), N,N'-di(1-naphthyl)-N,N'-diphenylbenzidine (NPB), N,N'-bis(1-naphthyl)-N,N'-diphenyl-4,4'-diamine (α-NPD), etc. However, embodiments of the present disclosure are not limited thereto.

The electron blocking layer EBL may include any suitable material available in the art. The electron blocking layer EBL may include, for example, a carbazole-based derivative (such as N-phenylcarbazole), a fluorene-based derivative, N,N'-bis(3-methylphenyl)-N,N'-diphenyl-[1,1-biphenyl]-4,4'-diamine (TPD), a triphenylamine-based derivative (such as 4,4',4"-tris(N-carbazolyl)triphenylamine (TCTA)), N,N'-di(naphthalene-1-yl)-N,N'-diphenyl-benzidine (NPD), 4,4'-cyclohexylidene bis[N,N-bis(4-methylphenyl)benzeneamine] (TAPC), 4,4'-bis[N,N-(3-tolyl)amino]-3,3'-dimethylbiphenyl (HMTPD), mCP, etc. In addition, as described above, the electron blocking layer EBL may include the nitrogen-containing compound according to an embodiment of the present disclosure.

In some embodiments, the thickness of the hole transport region HTR may be about 100 Å to about 10,000 Å, for example, about 100 Å to about 5,000 Å. In some embodiments, the thickness of the hole injection layer HIL may be, for example, about 30 Å to about 1,000 Å, and the thickness of the hole transport layer HTL may be about 30 Å to about 1,000 Å. In some embodiments, for example, the thickness of the electron blocking layer EBL may be about 10 Å to about 1,000 Å. When the thicknesses of the hole transport region HTR, the hole injection layer HIL, the hole transport layer HTL, and the electron blocking layer EBL satisfy the above-described ranges, satisfactory hole transport properties may be achieved without a substantial increase in driving voltage.

In some embodiments, the hole transport region HTR may further include a charge generating material in addition to the above-described materials in order to increase conductivity. The charge generating material may be dispersed substantially uniformly or non-uniformly in the hole transport region HTR. In some embodiments, the charge generating material may be, for example, a p-dopant. The p-dopant may be a quinone derivative, a metal oxide, or a cyano group-containing compound, without limitation. Non-limiting examples of the p-dopant may include quinone derivatives (such as tetracyanoquinodimethane (TCNQ) and/or 2,3,5,6-tetrafluoro-7,7,8,8-tetracyanoquinodimethane (F4-TCNQ)), metal oxides (such as tungsten oxide and/or molybdenum oxide), etc.

As described above, the hole transport region HTR may further include at least one of a hole buffer layer or an electron blocking layer EBL in addition to the hole injection layer HIL and the hole transport layer HTL. The hole buffer layer may compensate for an optical resonance distance according to the wavelength of light emitted from the emission layer EML, and may thereby increase the light emission efficiency. The materials included in the hole transport region HTR may be utilized as materials in the hole buffer layer.

In some embodiments, the hole transport region HTR may further include an electron blocking layer EBL, and the electron blocking layer EBL may be between the hole transport layer HTL and the emission layer EML. The electron blocking layer EBL is a layer that may play the role of blocking electron injection from the electron transport region ETR to the hole transport region HTR.

The emission layer EML may be on the hole transport region HTR. The thickness of the emission layer EML may be, for example, about 100 Å to about 300 Å. The emission layer EML may have a single layer structure formed using a single material, a single layer structure formed using a plurality of different materials, or a multilayer structure having a plurality of layers formed using a plurality of different materials.

The emission layer EML may be to emit red, green, blue, white, yellow, and/or cyan light. The emission layer EML may include a fluorescence emitting material and/or a phosphorescence emitting material.

The emission layer EML in the organic electroluminescence device 10 according to an embodiment of the present disclosure may be a fluorescence emission layer. The emission layer EML in the organic electroluminescence device 10 according to an embodiment of the present disclosure may be a fluorescence emission layer to emit blue light. For example, a portion of light that may be emitted from the emission layer EML may be due to thermally activated delayed fluorescence. In some embodiments, the emission layer EML of the organic electroluminescence device 10 according to an embodiment of the present disclosure may include a light-emitting component to emit thermally activated delayed fluorescence, and the emission layer EML of the organic electroluminescence device 10 according to an embodiment of the present disclosure may be a blue emission layer to emit thermally activated delayed fluorescence In some embodiments, in the organic electroluminescence device 10 according to an embodiment of the present disclosure, the emission layer EML may include a host and a dopant. The dopant may include the nitrogen-containing compound according to an embodiment of the present disclosure. In this case, the emission layer EML may have a thickness of about 100 Å to about 600 Å.

In the organic electroluminescence device 10 according to an embodiment of the present disclosure, the emission layer EML may include the nitrogen-containing compound according to an embodiment of the present disclosure. The organic electroluminescence device according to an embodiment of the present disclosure may include the nitrogen-containing compound represented by Formula 1 in the emission layer EML, which may be to emit fluorescence:

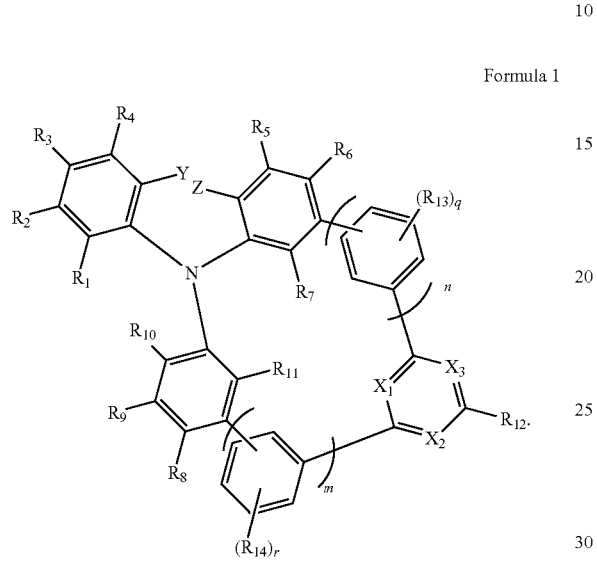

Formula 1

In some embodiments, in the organic electroluminescence device 10 according to an embodiment of the present disclosure, an emission layer EML may include a nitrogen-containing compound represented by Formula 1-1 or Formula 1-2:

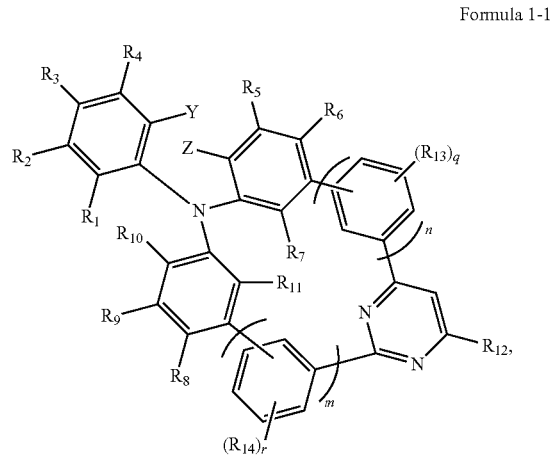

Formula 1-1

In Formula 1, at least two of $X_1$, $X_2$ or $X_3$ may be N, and the remainder thereof may be $CR_{15}$. Y and Z may each independently be a hydrogen atom, a deuterium atom, $OR_{16}$, $SR_{17}$, $CR_{18}R_{19}R_{20}$, or $SiR_{21}R_{22}R_{23}$, or may be combined with (e.g., linked to) each other to form a ring. In Formula 1, $R_1$ to $R_{14}$ may each independently be a hydrogen atom, a deuterium atom, $OR_{24}$, $SR_{25}$, $(C=O)R_{26}$, $NR_{27}R_{28}$, $CR_{29}R_{30}R_{31}$, $SiR_{32}R_{33}R_{34}$, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, or may be combined with (e.g., linked to) an adjacent group to form a ring. In addition, $R_{15}$ to $R_{34}$ may each independently be a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, or may be combined with (e.g., linked to) an adjacent group to form a ring.

In Formula 1, n and m may each independently be 1 or 2, and q and r may each independently be an integer of 0 to 4.

In the description of the nitrogen-containing compound represented by Formula 1, which is utilized in the organic electroluminescence device 10 according to an embodiment of the present disclosure, $X_1$ to $X_3$, Y, Z, $R_1$ to $R_{34}$, n, m, q, and r may each independently be the same as described above.

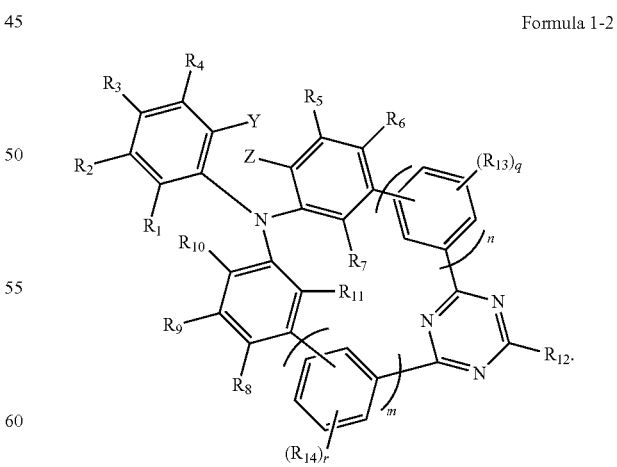

Formula 1-2

In Formula 1-1 and Formula 1-2, Y, Z, n, m, $R_1$ to $R_{34}$, q, and r may each independently be the same as defined in Formula 1.

In some embodiments, in the organic electroluminescence device 10 according to an embodiment of the present disclosure, an emission layer EML may include a nitrogen-containing compound represented by one of Formula 1-3 to Formula 1-6:

Formula 1-3
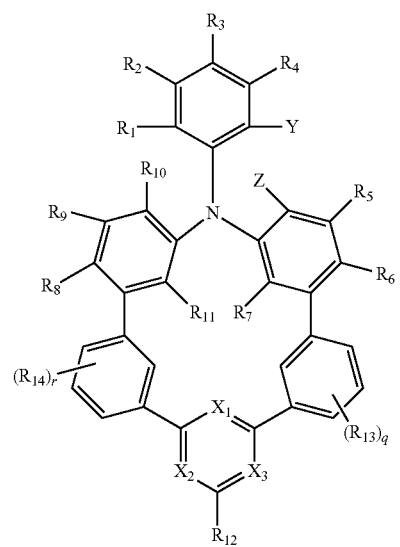

,

Formula 1-4
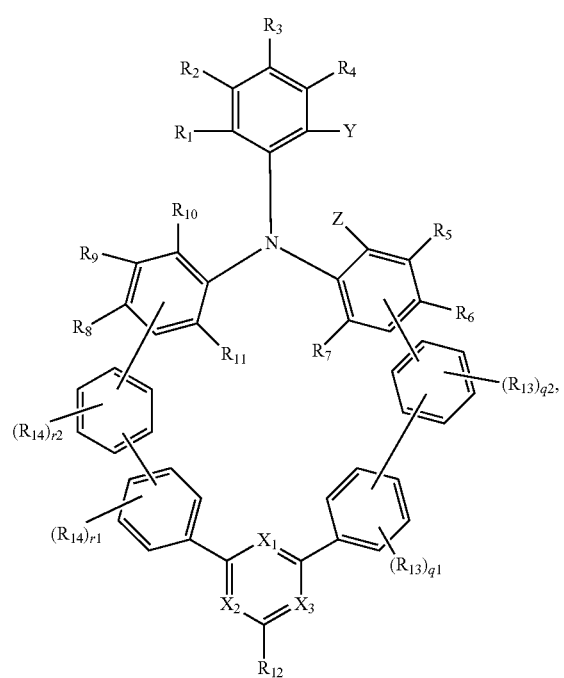

Formula 1-5
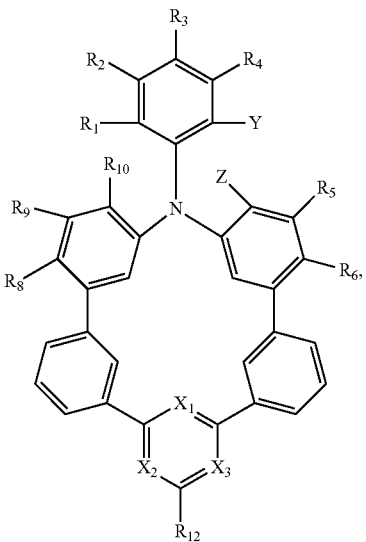

,

Formula 1-6
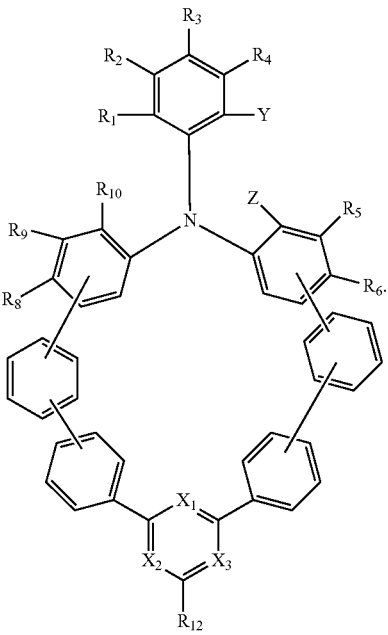

In Formula 1-3 and Formula 1-4, q1, q2, r1, and r2 may each independently be an integer of 0 to 4. In addition, in Formula 1-3 to Formula 1-6, $X_1$ to $X_3$, Y, Z, $R_1$ to $R_{34}$, q, and r may each independently be the same as described in connection with Formula 1.

The organic electroluminescence device 10 according to an embodiment of the present disclosure may include the nitrogen-containing compound represented by Formula 1 in an emission layer EML, and may be to emit delayed fluorescence. For example, the organic electroluminescence device 10 according to an embodiment of the present disclosure may include the nitrogen-containing compound according to an embodiment of the present disclosure, as represented by Formula 1, in an emission layer EML, and may be to emit thermally activated delayed fluorescence. The emission layer EML of the organic electroluminescence device 10 according to an embodiment of the present disclosure may include the nitrogen-containing compound represented by Formula 1 as a dopant material for emitting thermally activated delayed fluorescence.

The organic electroluminescence device 10 according to an embodiment of the present disclosure may include at least one compound represented in Compound Group 1 in an emission layer EML. For example, the organic electroluminescence device 10 according to an embodiment of the present disclosure may include at least one compound represented in Compound Group 1 in an emission layer EML as a dopant material. At least one nitrogen-containing compound selected from the compounds represented in Compound Group 1 may be included in the emission layer EML of the organic electroluminescence device 10 according to an embodiment of the present disclosure as a dopant material for thermally activated delayed fluorescence:

Compound Group 1

1
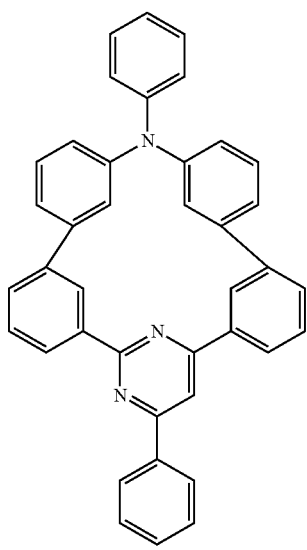

2
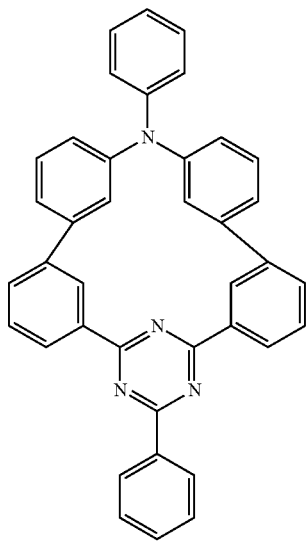

3
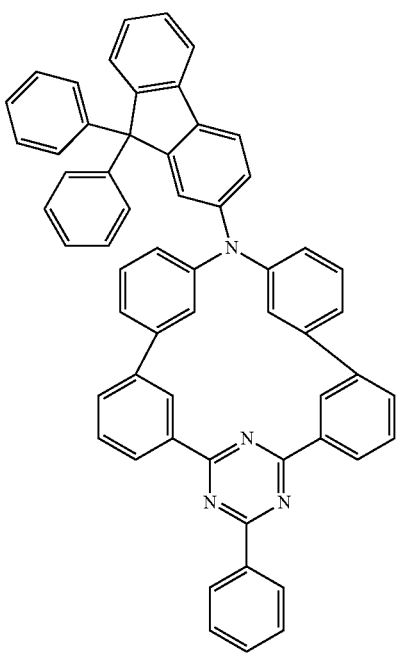

4
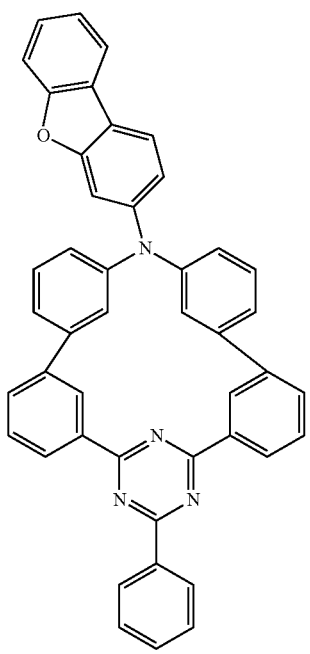

-continued
5
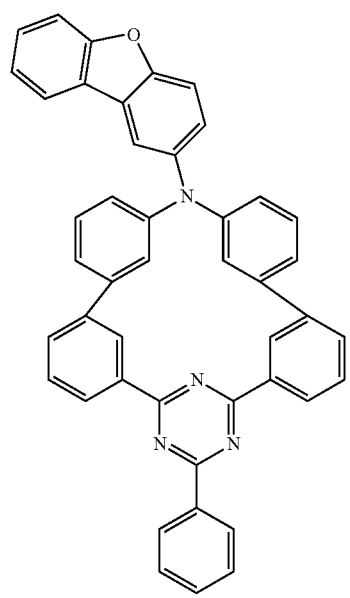
6
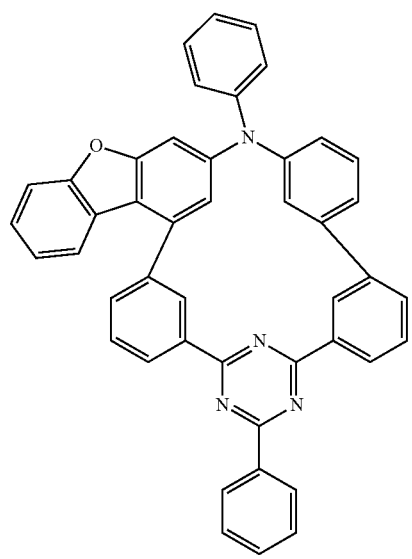
-continued
7
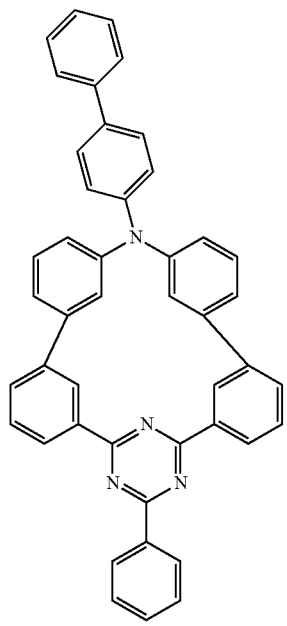
8
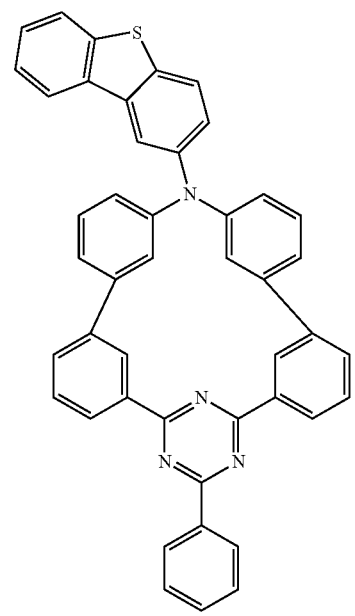

9
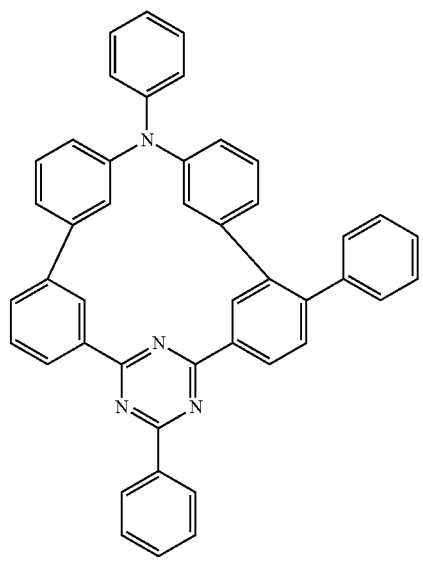
11
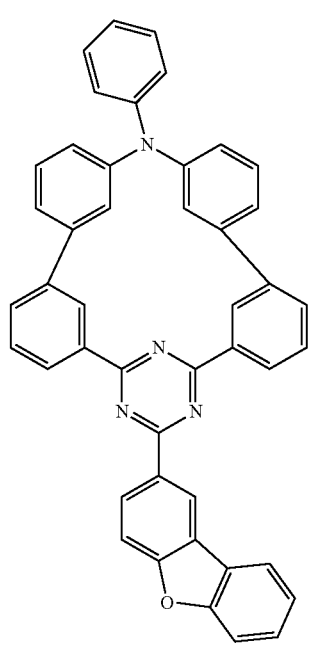
10
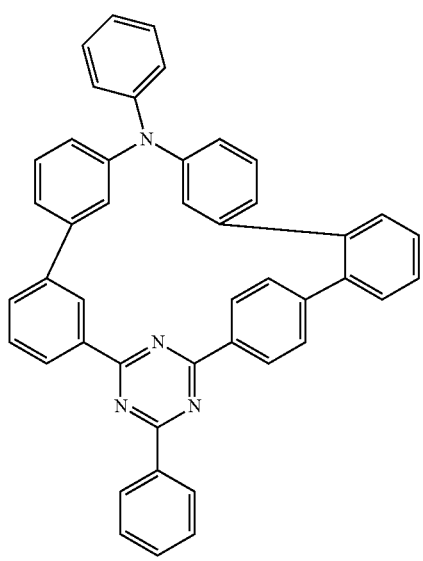
12
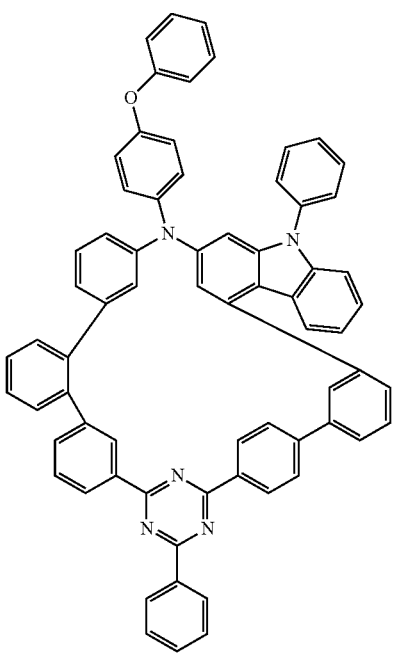

13
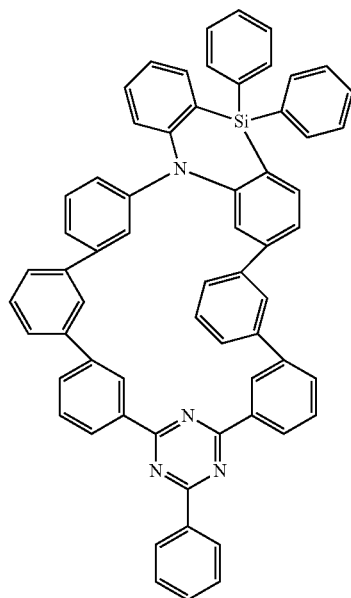
14
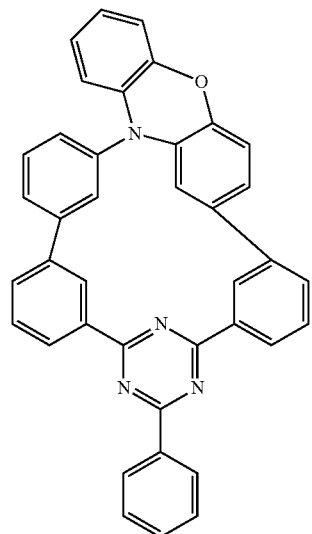
15
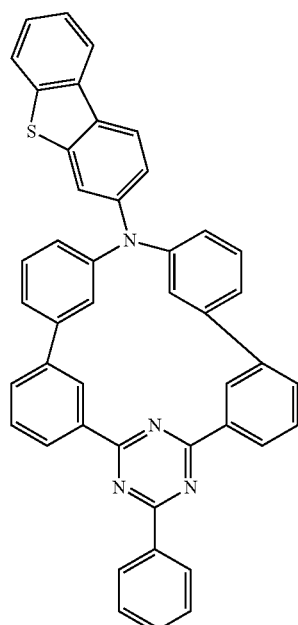
16
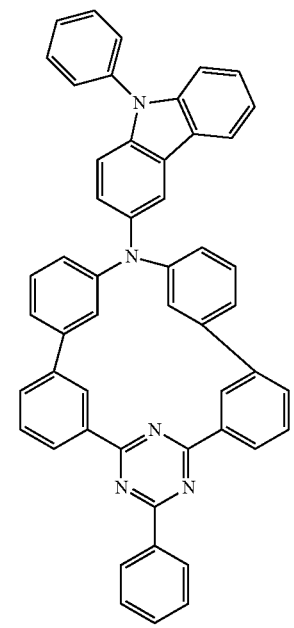

87
-continued
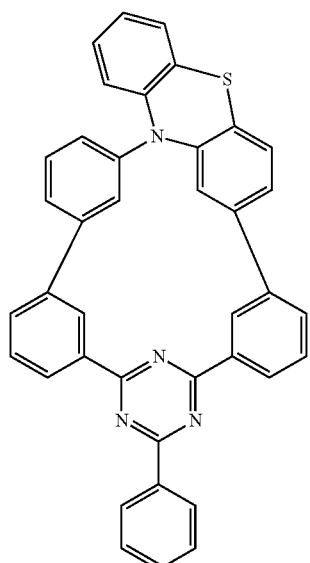
17
88
-continued
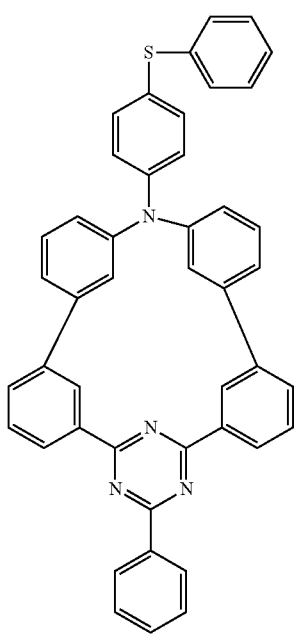
19
18
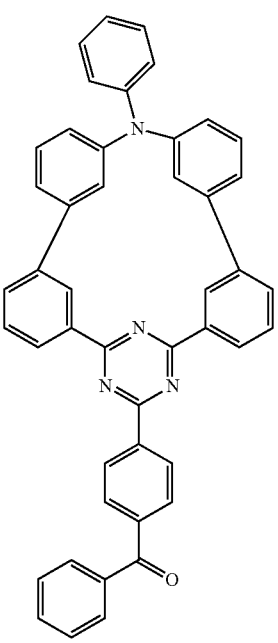
20

21
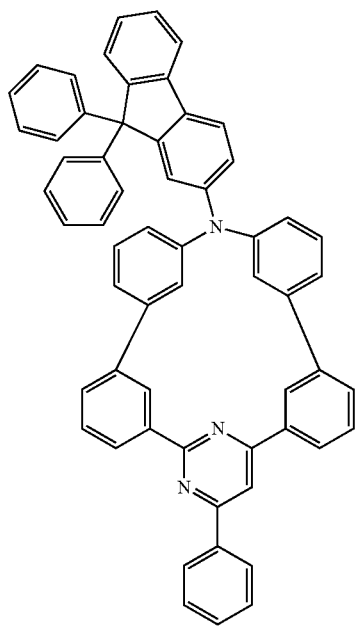
23
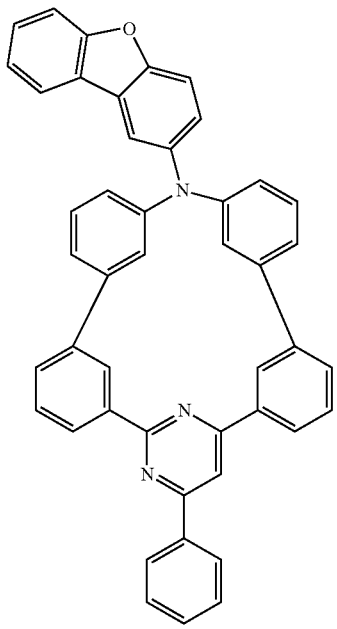
22
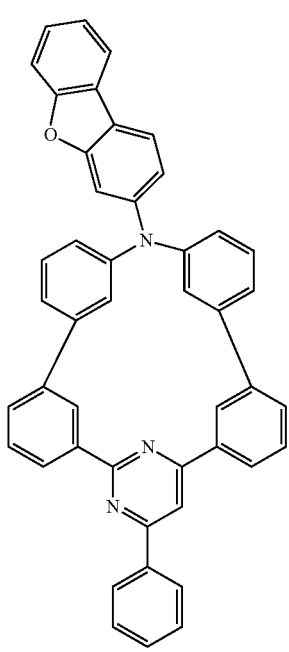
24
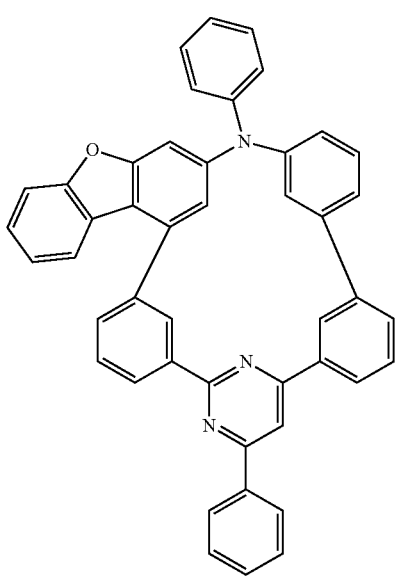

25
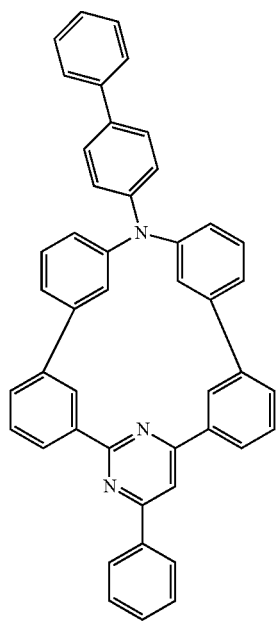
26
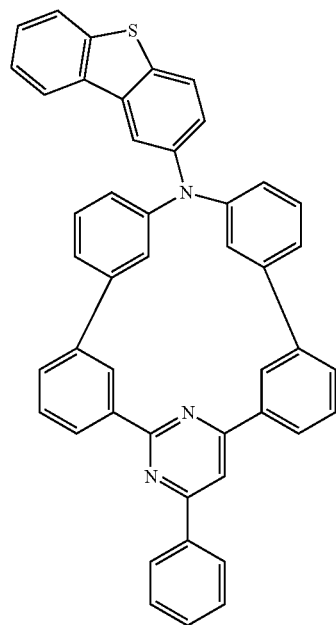
27
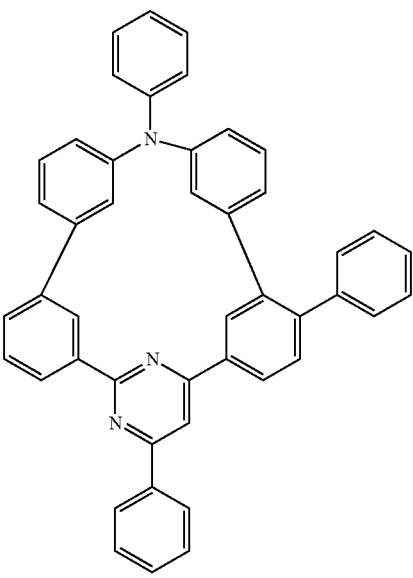
28
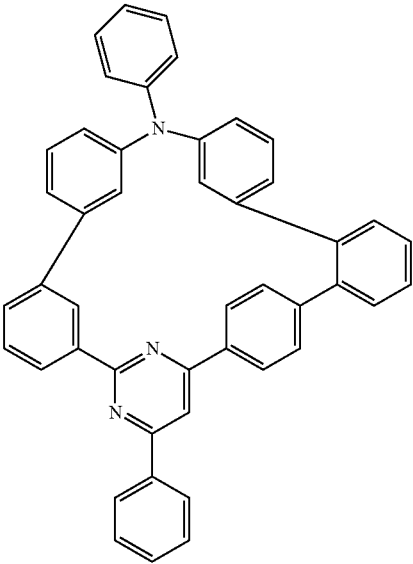

93
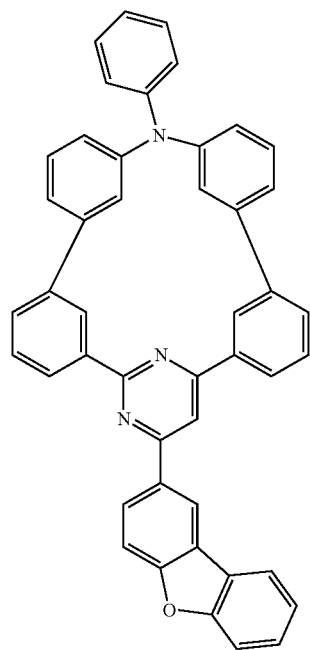
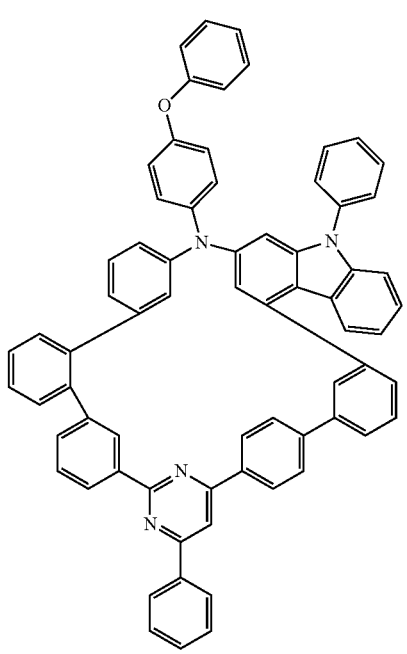
94
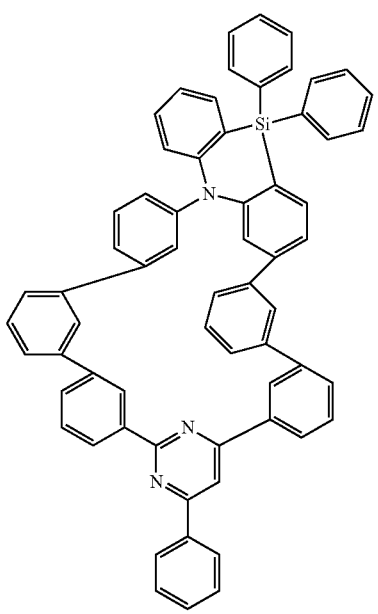
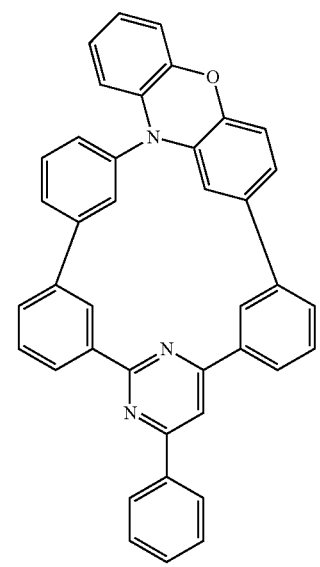

33
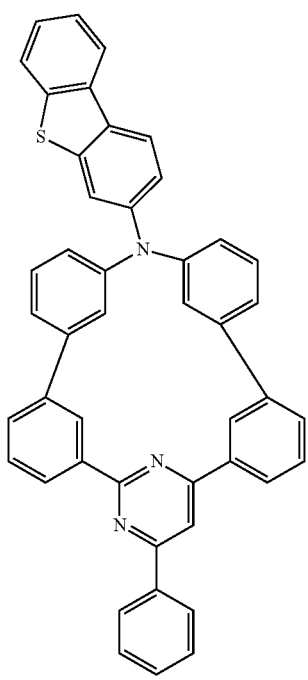
34
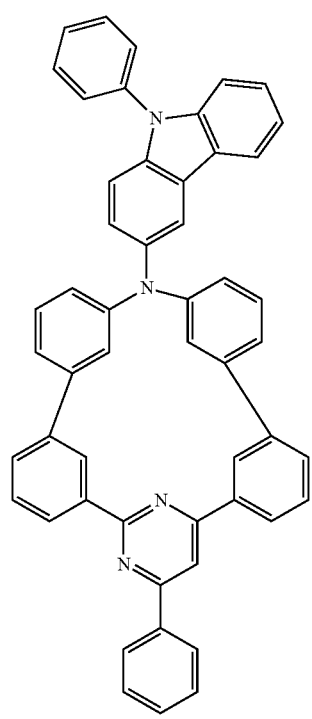
35
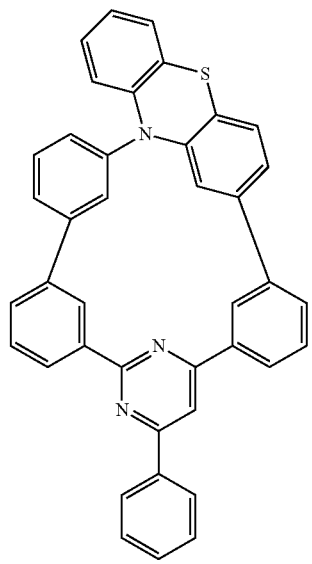
36
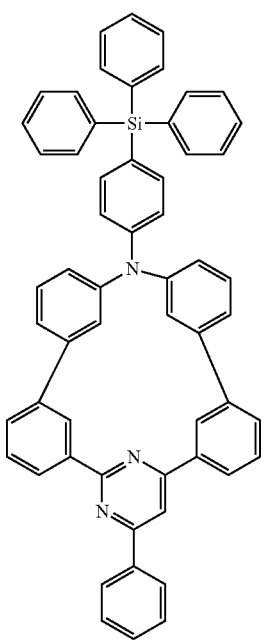

-continued

37

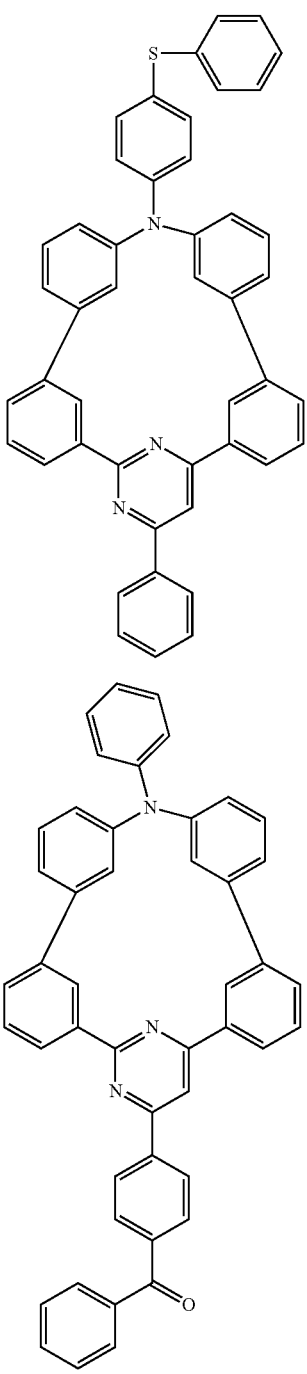

38

In some embodiments, an emission layer EML in the organic electroluminescence device according to an embodiment of the present disclosure may include the nitrogen-containing compound according to an embodiment of the present disclosure as a dopant for thermally activated delayed fluorescence, and may further include a host material for thermally activated delayed fluorescence. In some embodiments, for example, the emission layer EML according to an embodiment of the present disclosure may include as a host material at least one of bis[2-(diphenylphosphino) phenyl] ether oxide (DPEPO), 4,4'-bis(carbazol-9-yl)biphenyl (CBP), 1,3-bis(carbazol-9-yl)benzene (mCP), 2,8-bis (diphenylphosphoryl)dibenzo[b,d]furan (PPF), 4,4',4"-tris (carbazol-9-yl)-triphenylamine (TcTa), 1,3,5-tris(N-phenylbenzimidazole-2-yl)benzene (TPBi), 3,3'-bis(N-carbazolyl)-1,1'-biphenyl (mCBP), and/or 2,4,6-tris (biphenyl-3-yl)-1,3,5-triazine (T2T). In some embodiments, the emission layer EML in the organic electroluminescence device according to an embodiment of the present disclosure may further include any suitable host material, for example, tris(8-hydroxyquinolino)aluminum (Alq$_3$), poly(n-vinylcarbazole) (PVK), 9,10-di(naphthalene-2-yl)anthracene (ADN), 3-tert-butyl-9,10-di(naphth-2-yl)anthracene (TBADN), distyrylarylene (DSA), 4,4'-bis(9-carbazolyl)-2, 2"-dimethyl-biphenyl (CDBP), 2-methyl-9,10-bis(naphthalen-2-yl)anthracene (MADN), hexaphenyl cyclotriphosphazene (CP1), 1,4-bis(triphenylsilyl)benzene (UGH2), hexaphenylcyclotrisiloxane (DPSiO$_3$), and/or octaphenylcyclotetrasiloxane (DPSiO$_4$).

In some embodiments, the emission layer EML may further include any suitable dopant for emitting delayed fluorescence in addition to the nitrogen-containing compound according to an embodiment of the present disclosure. For example, the emission layer EML of the organic electroluminescence device 10 according to an embodiment of the present disclosure may further include as a dopant, at least one of 10-phenyl-10H,10'H-spiro[acridine-9,9"-anthracene]-10'-one (ACRSA), 3,4,5,6-tetra-9H-carbazol-9-yl-1,2-benzenedicarbonitrile (4CzPN), 2,4,5,6-tetra-9H-carbazol-9-yl-isophthalonitrile (4CzIPN), bis[4-9,9-dimethyl-9,10-dihydroacridine)phenyl]sulfone (DMAC-DPS), and 2-phenoxazine-4,6-diphenyl-1,3,5-triazine (PSZ-TRZ). In some embodiments, the emission layer EML may further include any suitable dopant material, for example, a styryl derivative (such as 1,4-bis[2-(3-N-ethylcarbazolyl)vinyl] benzene (BCzVB), 4-(di-p-tolylamino)-4'-[(di-p-tolylamino)styryl]stilbene (DPAVB), and/or N-(4-((E)-2-(6-((E)-4-(diphenylamino)styryl)naphthalen-2-yl)vinyl) phenyl)-N-phenylbenzenamine (N-BDAVBi)), perylene and derivatives thereof (such as 2,5,8,11-tetra-t-butylperylene (TBP)), pyrene and derivatives thereof (such as 1,1-dipyrene, 1,4-dipyrenylbenzene, and/or 1,4-bis(N,N-diphenylamino)pyrene), etc.

In some embodiments, the emission layer EML of the organic electroluminescence device 10 according to an embodiment of the present disclosure may be to emit blue light. The emission layer EML may be to emit light having a wavelength of about 450 nm to about 490 nm.

In the organic electroluminescence device 10 according to an embodiment of the present disclosure, the electron transport region ETR may be on the emission layer EML. The electron transport region ETR may include at least one of a hole blocking layer HBL, an electron transport layer ETL, and/or an electron injection layer EIL. However, embodiments of the present disclosure are not limited thereto.

The electron transport region ETR may have a single layer structure formed using a single material, a single layer structure formed using a plurality of different materials, or a multilayer structure having a plurality of layers formed using a plurality of different materials.

In some embodiments, for example, the electron transport region ETR may have a single layer structure including an electron injection layer EIL or an electron transport layer ETL, and the single layer structure may be formed using an electron injection material and an electron transport material. In some embodiments, the electron transport region ETR may have a single layer structure including a plurality of different materials, or a laminated multilayer structure on the emission layer EML including an electron transport layer ETL/electron injection layer EIL, or hole blocking layer/electron transport layer ETL/electron injection layer EIL, without limitation. In some embodiments, the thickness of the electron transport region ETR may be, for example, about 100 Å to about 1,500 Å.

The electron transport region ETR may be formed using one or more suitable methods (such as a vacuum deposition method, a spin coating method, a cast method, a Langmuir-Blodgett (LB) method, an inkjet printing method, a laser printing method, and/or a laser induced thermal imaging (LITI) method).

When the electron transport region ETR includes an electron transport layer ETL, the electron transport region ETR may include, for example, tris(8-hydroxyquinolinato) aluminum (Alq3), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,08)-(1,1'-biphenyl-4-olato)aluminum (BAlq), beryllium bis(benzoquinolin-10-olate (Bebq2), 9,10-di(naphthalene-2-yl)anthracene (ADN), or a mixture thereof, without limitation.

When the electron transport region ETR includes an electron transport layer ETL, the thickness of the electron transport layer ETL may be about 100 Å to about 1,000 Å, for example, about 150 Å to about 500 Å. When the thickness of the electron transport layer ETL satisfies the above-described range, satisfactory electron transport properties may be obtained without a substantial increase in driving voltage.

When the electron transport region ETR includes the electron injection layer EIL, the electron transport region ETR may include, for example, LiF, lithium quinolate (LiQ), Li$_2$O, BaO, NaCl, CsF, a lanthanide metal (such as Yb), or a metal halide (such as RbCl, RbI and/or KI). However, embodiments of the present disclosure are not limited thereto. In some embodiments, the electron injection layer EIL may be formed using a mixture of an electron transport material and an insulating organometallic salt. The organometallic salt may be a material having an energy band gap of about 4 eV or more. In some embodiments, the organometallic salt may include, for example, a metal acetate, a metal benzoate, a metal acetoacetate, a metal acetylacetonate, and/or a metal stearate.

When the electron transport region ETR includes an electron injection layer EIL, the thickness of the electron injection layer EIL may be about 1 Å to about 100 Å, and about 3 Å to about 90 Å. When the thickness of the electron injection layer EIL satisfies the above described range, satisfactory electron injection properties may be obtained without inducing a substantial increase in driving voltage.

The electron transport region ETR may include a hole blocking layer as described above. The hole blocking layer may include, for example, at least one of 2,9-dimethyl-4,7-diphenyl-1,10-phenanthroline (BCP) or 4,7-diphenyl-1,10-phenanthroline (Bphen). However, embodiments of the present disclosure are not limited thereto.

The second electrode EL2 may be on the electron transport region ETR. The second electrode EL2 may have conductivity (e.g., may be conductive). The second electrode EL2 may be formed using a metal alloy and/or a conductive compound. The second electrode EL2 may be a cathode. The second electrode EL2 may be a transmissive electrode, a transflective electrode, or a reflective electrode. When the second electrode EL2 is a transmissive electrode, the second electrode EL2 may include a transparent metal oxide, for example, ITO, IZO, ZnO, ITZO, etc.

When the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). In some embodiments, the second electrode EL2 may have a multi-layered structure including a reflective layer or a transfective layer formed using the above-described materials and a transparent conductive layer formed using ITO, IZO, ZnO, ITZO, etc.

In some embodiments, the second electrode EL2 may be connected with an auxiliary electrode. When the second electrode EL2 is connected with the auxiliary electrode, the resistance of the second electrode EL2 may decrease.

In the organic electroluminescence device 10, when a voltage is applied to each of the first electrode EL1 and second electrode EL2, holes injected from the first electrode EL1 may move via the hole transport region HTR into the emission layer EML, and electrons injected from the second electrode EL2 may move via the electron transport region ETR into the emission layer EML. The electrons and the holes may be recombined in the emission layer EML to produce excitons, and the excitons may emit light (e.g., cause light to be emitted) upon transitioning from an excited state to a ground state.

When the organic electroluminescence device 10 is atop emission type (e.g., top emission OLED), the first electrode EL1 may be a reflective electrode and the second electrode EL2 may be a transmissive electrode or a transflective electrode. When the organic electroluminescence device 10 is a bottom emission type (e.g., bottom emission OLED), the first electrode EL1 may be a transmissive electrode or a transflective electrode and the second electrode EL2 may be a reflective electrode.

The organic electroluminescence device according to an embodiment of the present disclosure may include the nitrogen-containing compound according to an embodiment of the present disclosure in an emission layer, and may have improved emission efficiency. For example, the organic electroluminescence device according to an embodiment of the present disclosure may include the nitrogen-containing compound according to an embodiment of the present disclosure as a dopant material in the emission layer so that the emission layer may be to emit light via a thermally activated delayed fluorescence component, thereby showing improved emission efficiency.

Hereinafter, a nitrogen-containing compound according to an embodiment of the present disclosure and an organic electroluminescence device including the nitrogen-containing compound will be explained in more detail with reference to embodiments and comparative embodiments. The following embodiments are illustrations to assist the understanding of the present disclosure, and do not limit the scope of the present disclosure.

EXAMPLES

1. Synthesis of Nitrogen-Containing Compounds

First, the synthetic method of the nitrogen-containing compound according to an embodiment of the present disclosure will be explained by referring to the synthetic methods of Compound 1, Compound 2, Compound 3, Compound 4, and Compound 11. The synthetic methods of the nitrogen-containing compound presented herein are only example embodiments, and synthetic methods for producing nitrogen-containing compounds according to embodiments of the present disclosure are not limited thereto.

Synthesis of Compound 1

Compound 1 including nitrogen according to an embodiment of the present disclosure may be synthesized by performing, for example, the steps of Reaction 1-1 to Reaction 1-3:

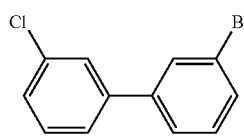
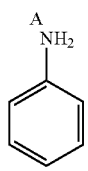
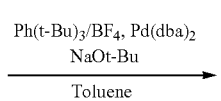
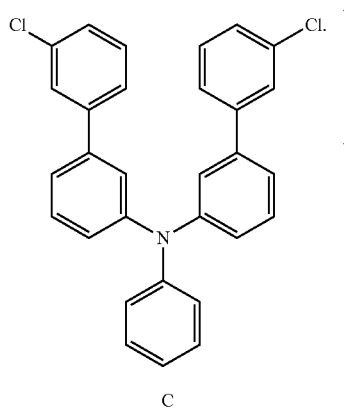

Compound C was synthesized by the process of Reaction 1-1. In Reaction 1-1, 6.3 g of Compound A, 1.1 g of Compound B, 0.27 g of Pd(dba)$_2$, 0.14 g of PH(tBu)$_3$/BF$_4$, and 2.3 g of NaOt-Bu were added to a 500 mL three neck flask under an argon atmosphere, followed by heating and refluxing in 200 mL of toluene for about 15 hours. After cooling in the air, water was added, an organic layer was separated, and solvents were removed. The crude product thus obtained was separated by silica gel chromatography (using a mixed solvent of toluene/hexane), and recrystallized using hexane to obtain 4.6 g (yield 83%) of the target product as a white solid. The molecular weight of the target product as measured by FAB-MS was 466. From the results, the target product was identified as Compound C.

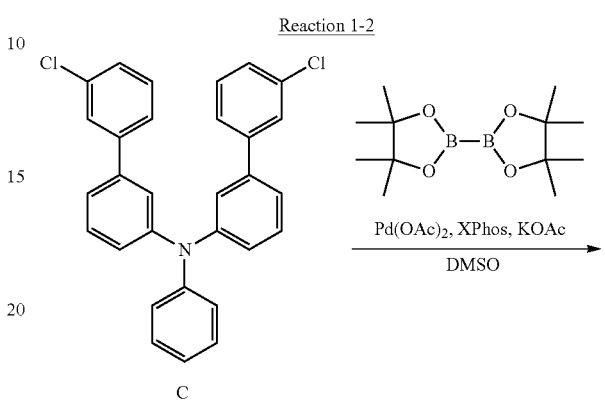
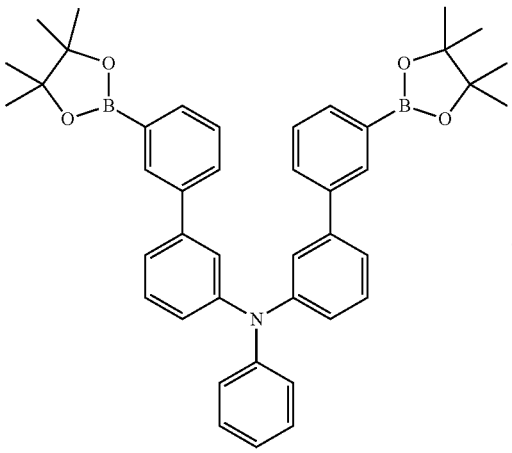

Then, Compound D was synthesized from Compound C by the process of Reaction 1-2. 3.0 g of Compound C, 5.0 g of bis(pinacolato)diboron, 0.15 g of Pd(OAc)$_2$, 0.32 g of XPhos, and 2.6 g of KOAc were added to a 300 mL three neck flask under an argon atmosphere, followed by heating and refluxing in 60 mL of a DMSO solvent for about 15 hours. After cooling in the air, water was added, an organic layer was separated, and solvents were removed. The crude product thus obtained was separated by silica gel chromatography (using toluene), and recrystallized using hexane to obtain 4.0 g (yield 87%) of the target product as a white solid. The molecular weight of the target product as measured by FAB-MS was 689. From the results, the target product was identified as Compound D.

Reaction 1-3

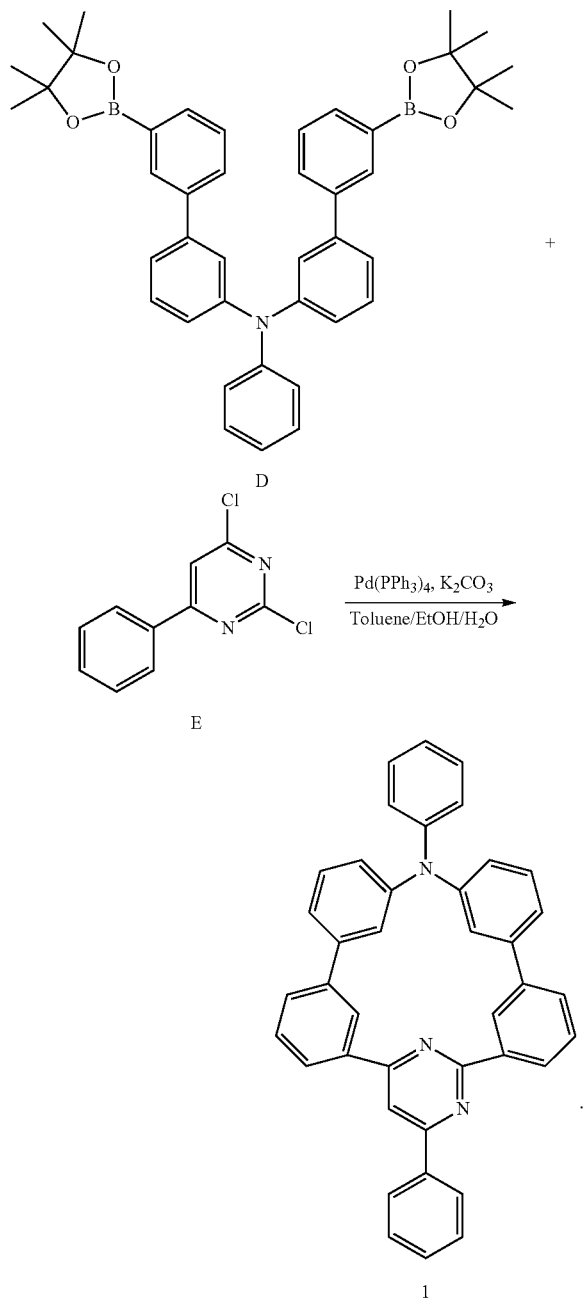

Synthesis of Compound 2

Reaction 2

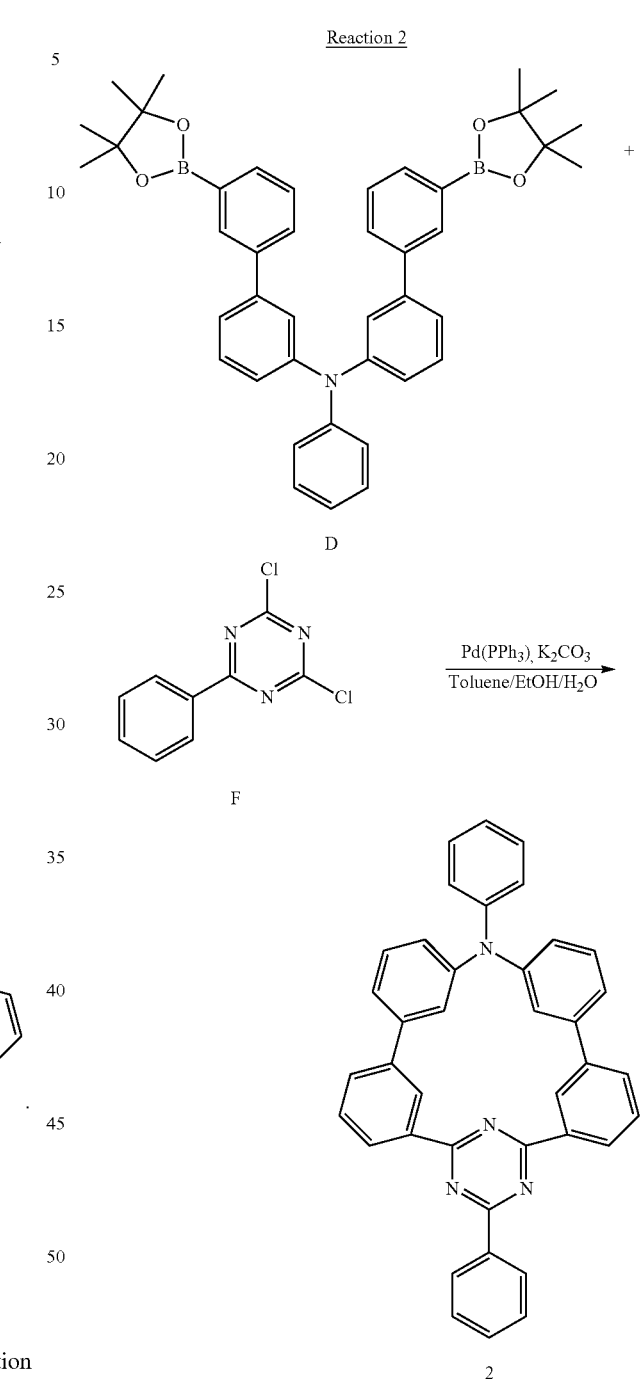

Compound 1 was synthesized by the process of Reaction 1-3. 1.4 g of Compound D, 0.5 g of Compound E, 0.26 g of Pd(PPh$_3$)$_4$, and 0.92 g of K$_2$CO$_3$ were added to a 300 mL three neck flask under an argon atmosphere, followed by heating and refluxing in a mixed solvent of 100 mL toluene, 5 mL ethanol and 10 mL distilled water for about 15 hours. After cooling in the air, water was added, an organic layer was separated, and solvents were removed. The crude product thus obtained was separated by silica gel chromatography (using a mixed solvent of toluene/hexane), and recrystallized using hexane to obtain 0.61 g (yield 50%) of a target product as a white solid. The molecular weight of the target product measured by FAB-MS was 550. From the results, the target product was identified as Compound 1.

Compound 2 including nitrogen according to an embodiment of the present disclosure may be synthesized by, for example, by the process of Reaction 2. In the synthetic method of Compound 2, the same method as the synthetic method of Compound 1 was performed except for using Compound F instead of Compound E to obtain 0.63 g (yield 73%) of the target product, Compound 2. The molecular weight of the target product as measured by FAB-MS was 551. From the results, the target product was identified as Compound 2.

Synthesis of Compound 3

Compound 3 including nitrogen according to an embodiment of the present disclosure may be synthesized by, for example, performing the steps of Reaction 3-1 to Reaction 3-3:

Reaction 3-1

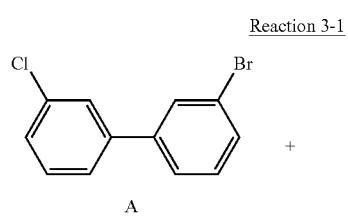

A

+

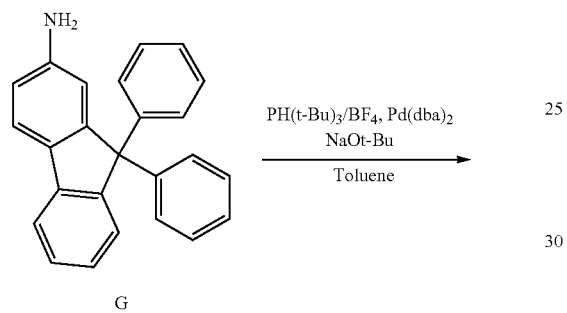

G

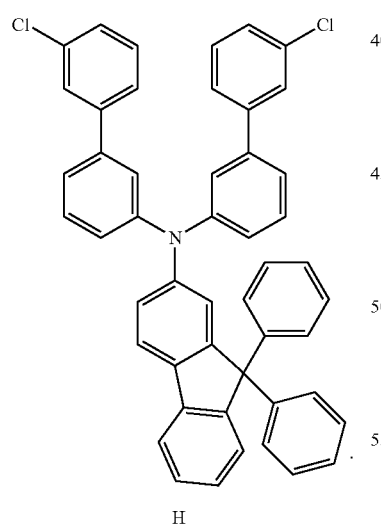

H

Compound H was synthesized by the process of Reaction 3-1. In the synthesis of Compound H, the same method as the synthetic method of Compound C of Reaction 1-1 was performed except for using Compound G instead of Compound B to obtain 6.4 g (yield 78%) of the target product Compound H. The molecular weight of Compound H as measured by FAB-MS was 707.

Reaction 3-2

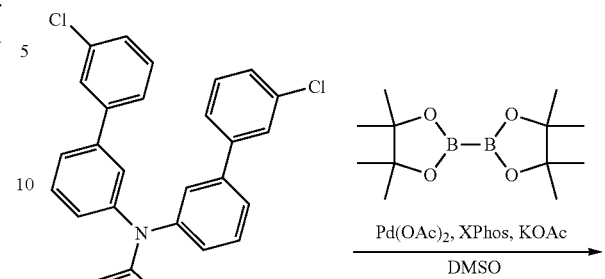

H

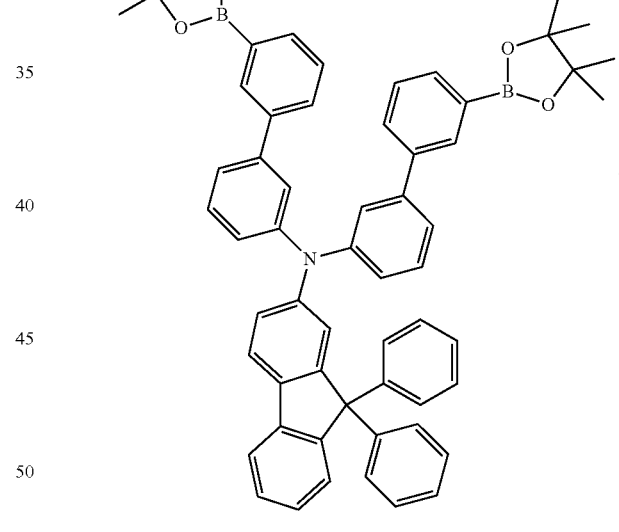

I

Then, Compound I was synthesized from Compound H by the process of Reaction 3-2. In the synthesis of Compound I, the same method as the synthetic method of Compound D of Reaction 1-2 was performed except for using Compound H instead of Compound C to obtain 3.4 g (yield 91%) of the target product Compound I. The molecular weight of Compound I as measured by FAB-MS was 890, and from the results, the target product was identified as Compound I.

Reaction 3-3

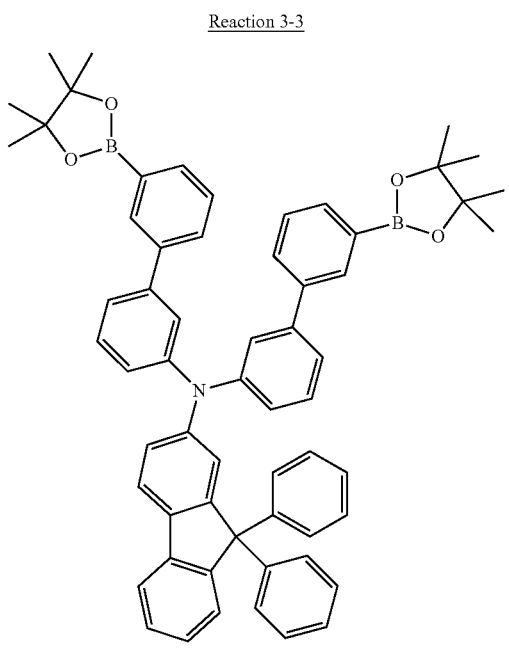

I

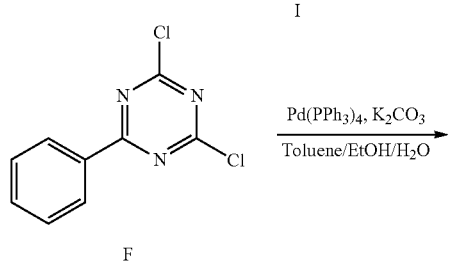

F

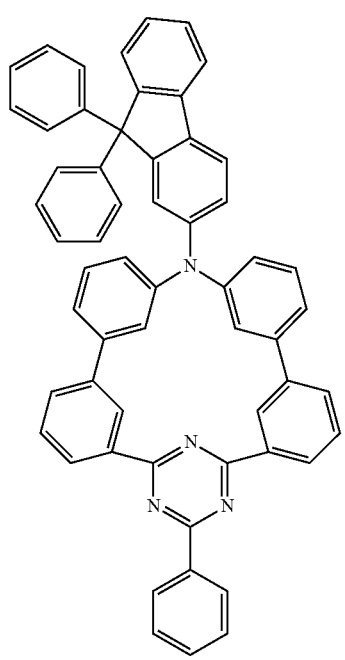

3

Then, Compound 3 was synthesized by the process of Reaction 3-3. In the synthesis of Compound 3, the same method as the synthetic method of Compound I of Reaction 1-3 was performed except for using Compound I instead of Compound D and Compound F instead of Compound E to obtain 0.74 g (yield 43%) of the target product Compound 3. The molecular weight of Compound 3 as measured by FAB-MS was 778, and from the results, the target product was identified as Compound 3.

Synthesis of Compound 4

Compound 4 including nitrogen according to an embodiment of the present disclosure may be synthesized by, for example, performing the steps of Reaction 4-1 to Reaction 4-3:

Reaction 4-1

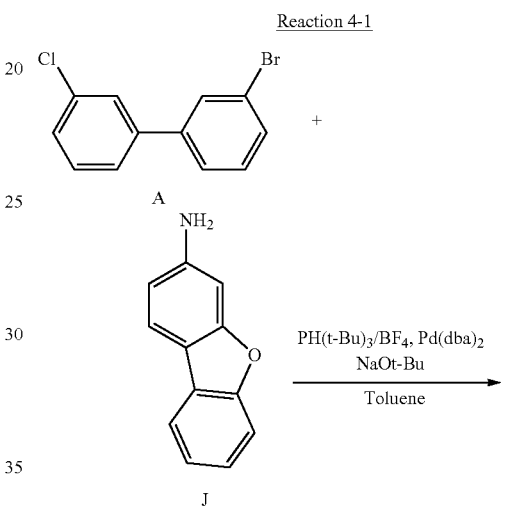

J

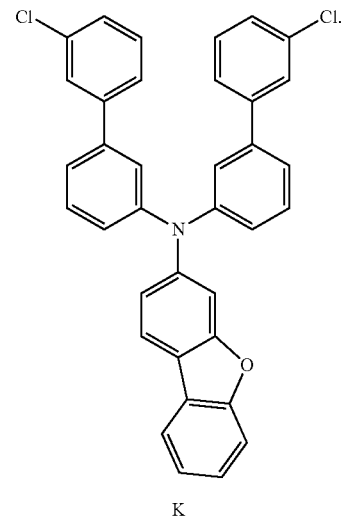

K

Compound K was synthesized by the process of Reaction 4-1. In the synthesis of Compound K, the same method as the synthetic method of Compound C of Reaction 1-1 was performed except for using Compound J instead of Compound B to obtain 6.2 g (yield 95%) of the target product Compound K. The molecular weight of Compound K as measured by FAB-MS was 557.

Reaction 4-2

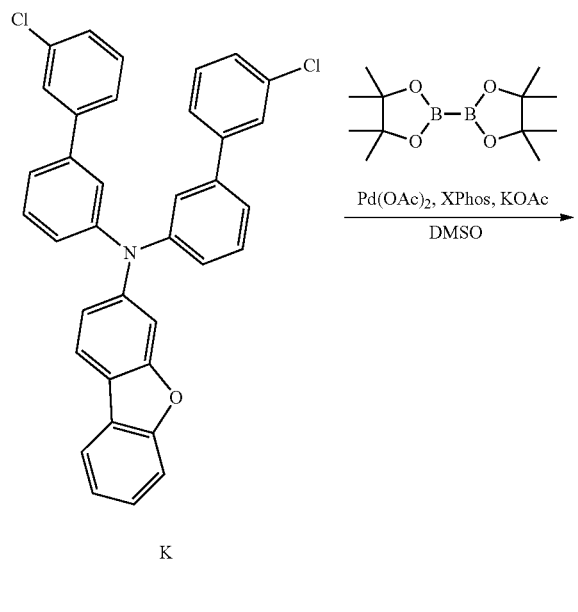

K

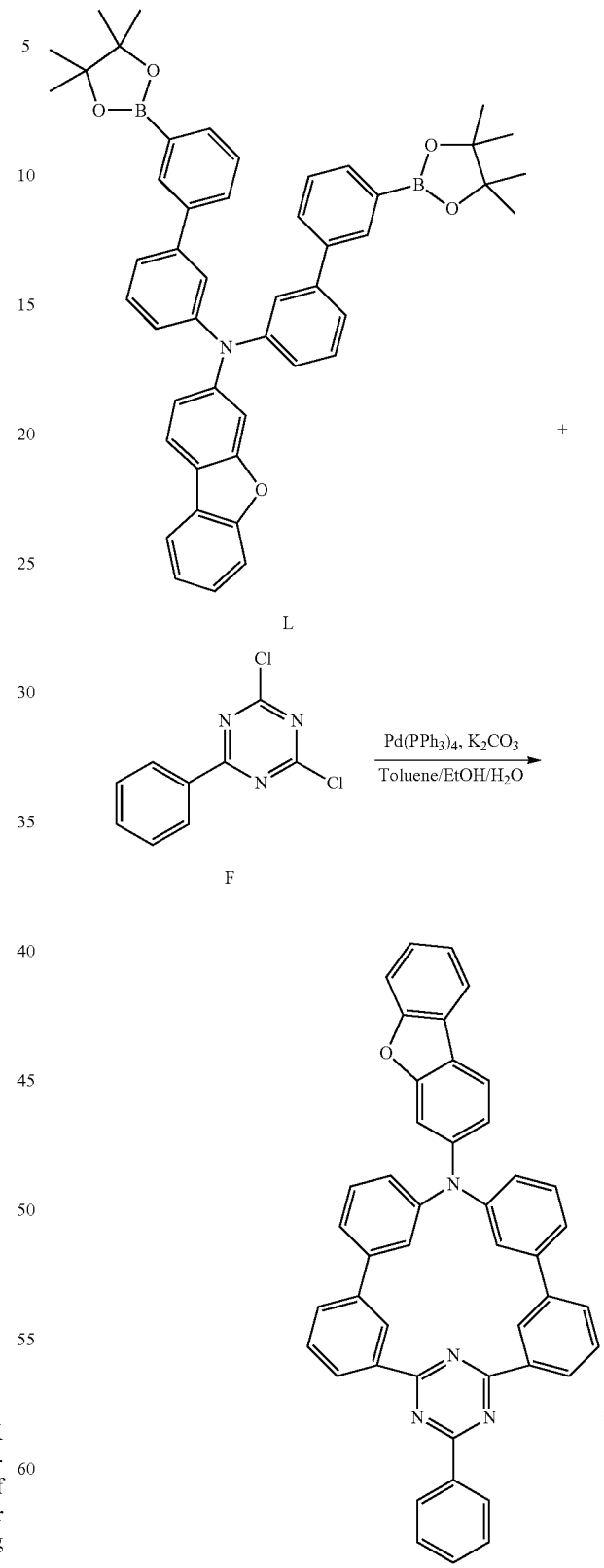

Then, Compound L was synthesized from Compound K by the process of Reaction 4-2. In the synthesis of Compound L, the same method as the synthetic method of Compound D of Reaction 1-2 was performed except for using Compound K instead of Compound C to obtain 3.7 g (yield 93%) of the target product Compound L. The molecular weight of Compound L as measured by FAB-MS was 740, and from the results, the target product was identified as Compound L.

Then, Compound 4 was synthesized by the process of Reaction 4-3. In the synthesis of Compound 4, the same method as the synthetic method of Compound 1 of Reaction 1-3 was performed except for using Compound L instead of Compound D and using Compound F instead of Compound E to obtain 0.51 g (yield 36%) of the target product Compound 4. The molecular weight of Compound 4 as measured by FAB-MS was 641, and from the results, the target product was identified as Compound 4.

Synthesis of Compound 11

Reaction 5

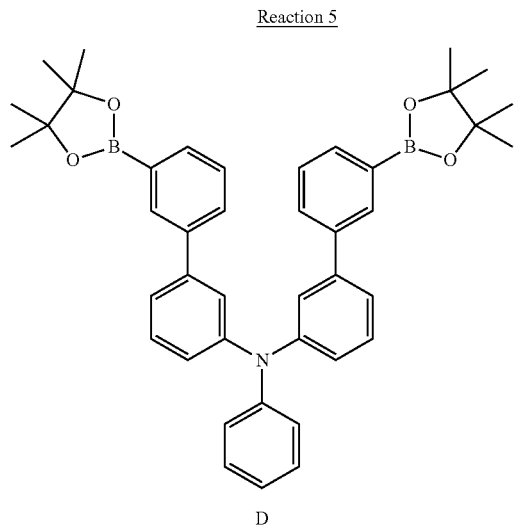

D

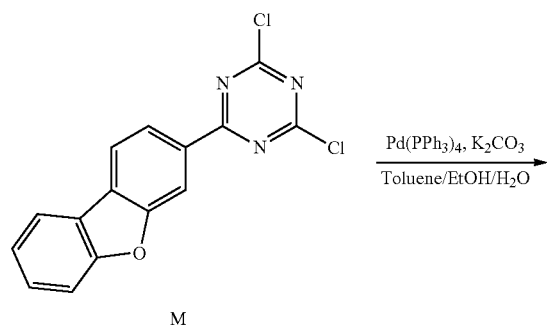

M

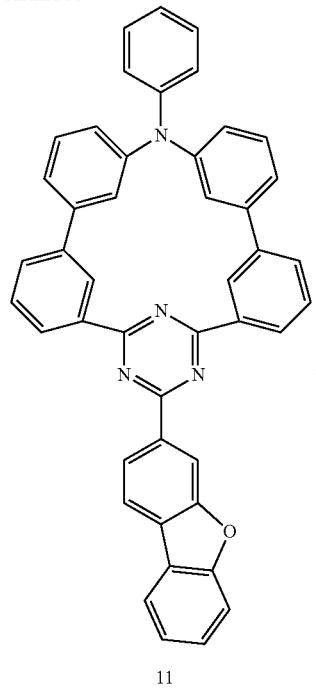

11

Compound 11 including nitrogen according to an embodiment of the present disclosure may be synthesized, for example, by Reaction 5. In the synthesis of Compound 11, the same method as the synthetic method of Compound 1 of Reaction 1-3 was performed except for using Compound M instead of Compound E to obtain 0.42 g (yield 41%) of the target product Compound 11. The molecular weight of the target product as measured by FAB-MS was 641, and from the results, the target product was identified as Compound 11.

2. Calculation of Energy Level of Nitrogen-Containing Compounds

The lowest excitation singlet energy levels (S1 energy level) and the lowest excitation triplet energy levels (T1 energy level) of each of the nitrogen-containing compounds of the example embodiments and the comparative compounds were calculated using a non-empirical molecular orbital method.

Table 1 shows the example compounds and comparative compounds used for the calculation of energy levels, and Table 2 shows the S1 energy level, T1 energy level, and $\Delta E_{ST}$ (difference between S1 energy level and T1 energy level, S1-T1) of each of the compounds shown in Table 1 (units are in eV). The energy levels shown in Table 2 were calculated using a B3LYP functional and 6-31G(d) basis set using Gaussian 09 (Gaussian Inc., Wallingford, Conn.).

TABLE 1
Example Compound 1
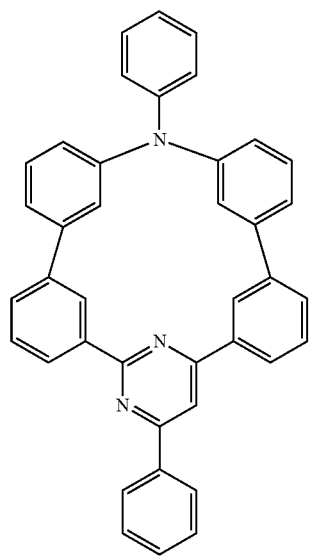 [SMILES: c1ccc(-c2cc3nc(n2)-c2cccc(c2)-c2cccc(c2)N(c2ccccc2)c2cccc(c2)-c2cccc-3c2)cc1]
1
Example Compound 2
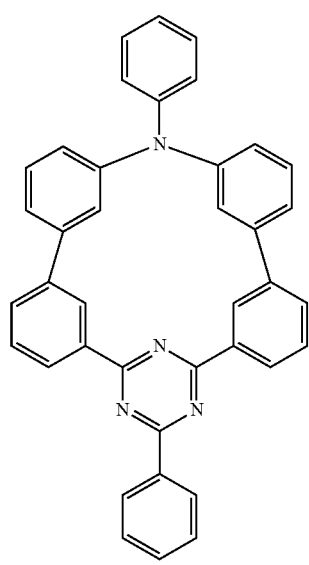 [SMILES: c1ccc(-c2nc3nc(n2)-c2cccc(c2)-c2cccc(c2)N(c2ccccc2)c2cccc(c2)-c2cccc-3c2)cc1]
2

TABLE 1-continued
| Example Compound 3 | 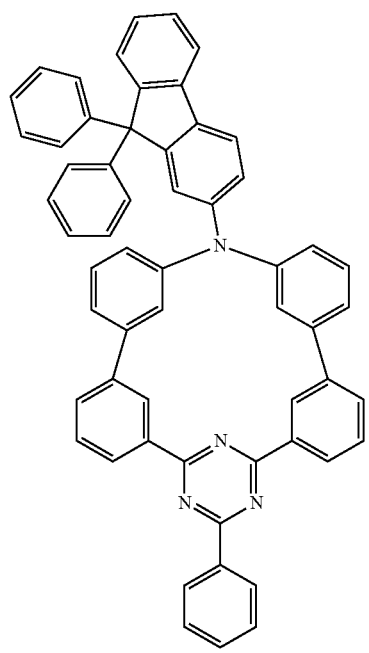 [SMILES: c1ccc(-c2nc3nc(n2)-c2cccc(c2)-c2cccc(c2)N(c2ccc4c(c2)C(c2ccccc2)(c2ccccc2)c2ccccc2-4)c2cccc(c2)-c2cccc-3c2)cc1] |
| --- | --- |
| | 3 |
| Example Compound 4 | 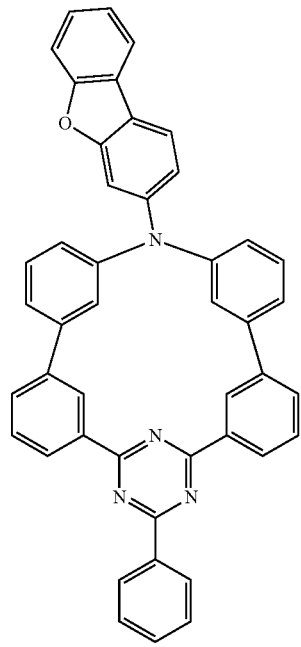 [SMILES: c1ccc(-c2nc3nc(n2)-c2cccc(c2)-c2cccc(c2)N(c2ccc4c(c2)oc2ccccc24)c2cccc(c2)-c2cccc-3c2)cc1] |
| | 4 |

TABLE 1-continued
| Example Compound 5 | 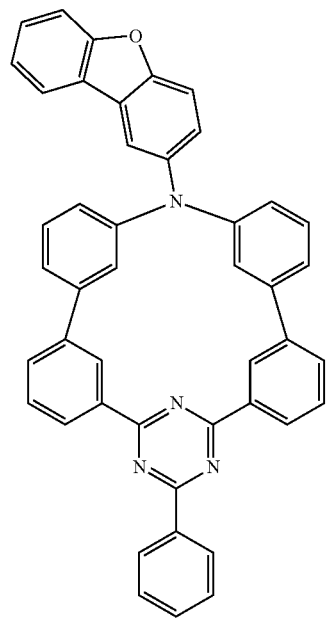 [SMILES: c1ccc(-c2nc3nc(n2)-c2cccc(c2)-c2cccc(c2)N(c2ccc4oc5ccccc5c4c2)c2cccc(c2)-c2cccc-3c2)cc1] |
5
| Comparative Compound X-1 | 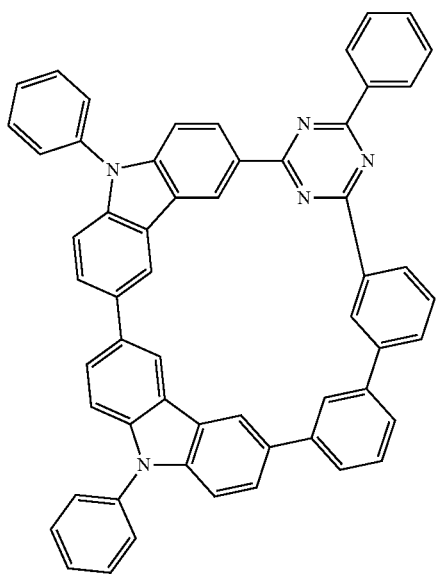 [SMILES: c1ccc(-c2nc3nc(n2)c2ccc4c(c2)c2cc(ccc2n4-c2ccccc2)c2ccc4c(c2)c2cc(ccc2n4-c2ccccc2)c2cccc(c2)c2cccc3c2)cc1] |
X-1

TABLE 1-continued
| Comparative Compound X-2 | 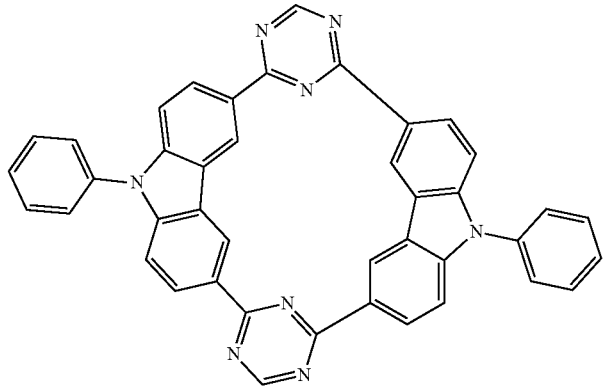 [SMILES: c1ccc(-n2c3ccc4cc3c3cc(ccc32)c2ncnc(n2)c2ccc3c(c2)c2cc(ccc2n3-c2ccccc2)c2ncnc4n2)cc1] |
| --- | --- |
| | X-2 |
| Comparative Compound X-3 | 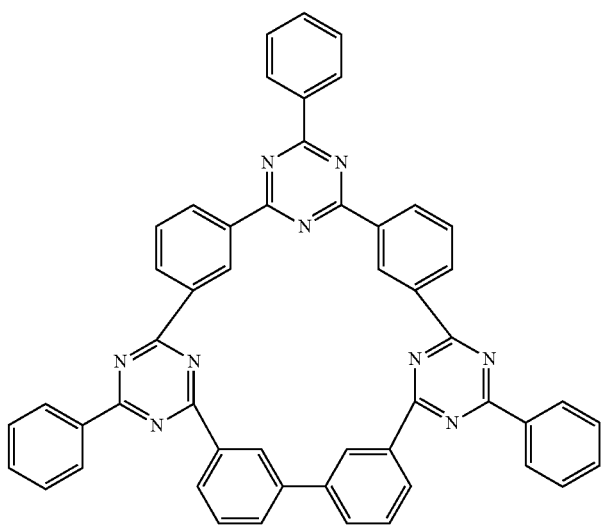 [SMILES: c1ccc(-c2nc3nc(n2)-c2cccc(c2)-c2nc(-c4ccccc4)nc(n2)-c2cccc(c2)-c2nc(-c4ccccc4)nc(n2)-c2cccc(c2)-c2cccc-3c2)cc1] |
| | X-3 |
| Comparative Compound X-4 | 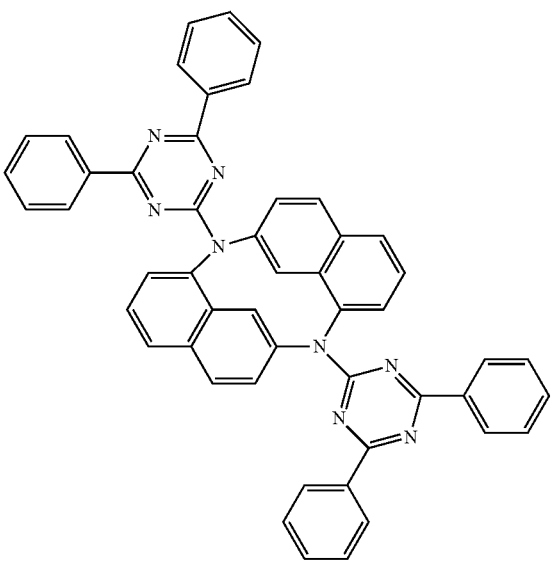 [SMILES: c1ccc(-c2nc(-c3ccccc3)nc(-n3c4ccc5cccc(c5c4)n(-c4nc(-c5ccccc5)nc(-c5ccccc5)n4)c4ccc5cccc3c5c4)n2)cc1] |
| | X-4 |

TABLE 1-continued
Example Compound 6
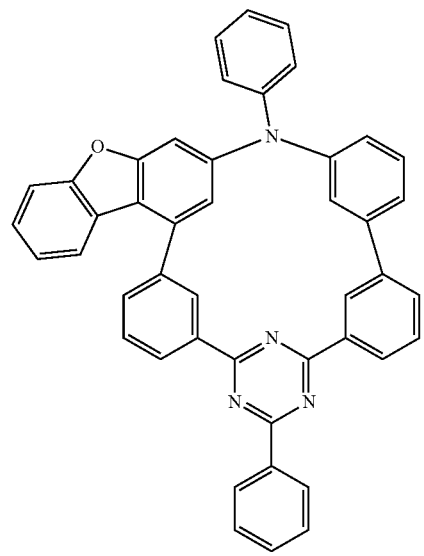 [SMILES: c1ccc(-c2nc3nc(n2)-c2cccc(c2)-c2cc(cc4oc5ccccc5c24)N(c2ccccc2)c2cccc(c2)-c2cccc-3c2)cc1]
6
Example Compound 7
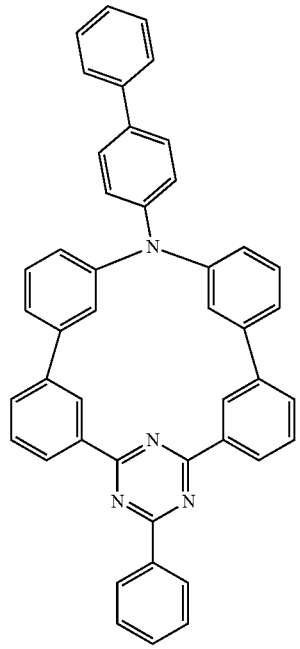 [SMILES: c1ccc(-c2ccc(N3c4cccc(c4)-c4cccc(c4)-c4nc(-c5ccccc5)nc(n4)-c4cccc(c4)-c4cccc3c4)cc2)cc1]
7

TABLE 1-continued
| Example Compound 8 | 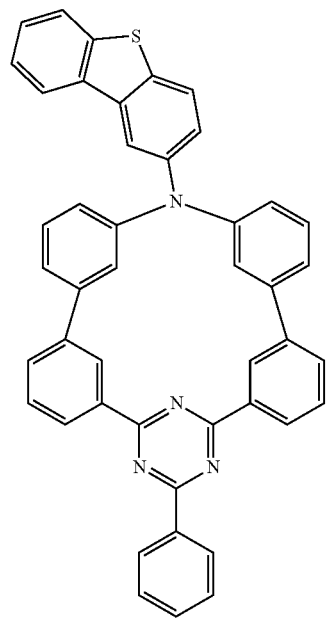 [SMILES: c1ccc(-c2nc3nc(n2)-c2cccc(c2)-c2cccc(c2)N(c2ccc4sc5ccccc5c4c2)c2cccc(c2)-c2cccc-3c2)cc1] |
|---|---|
| | 8 |
| Example Compound 9 | 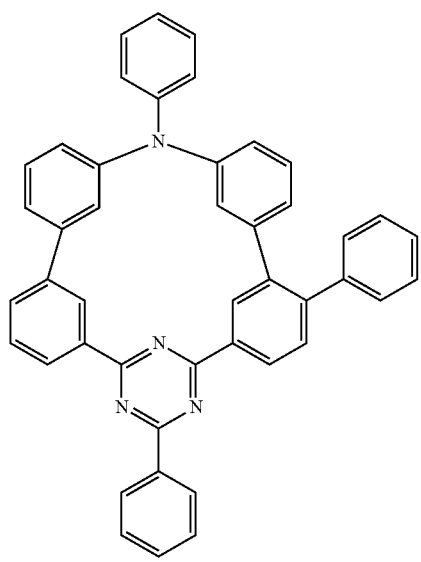 [SMILES: c1ccc(-c2nc3nc(n2)-c2ccc(-c4ccccc4)c(c2)-c2cccc(c2)N(c2ccccc2)c2cccc(c2)-c2cccc-3c2)cc1] |
|---|---|
| | 9 |

TABLE 1-continued
Example Compound 10
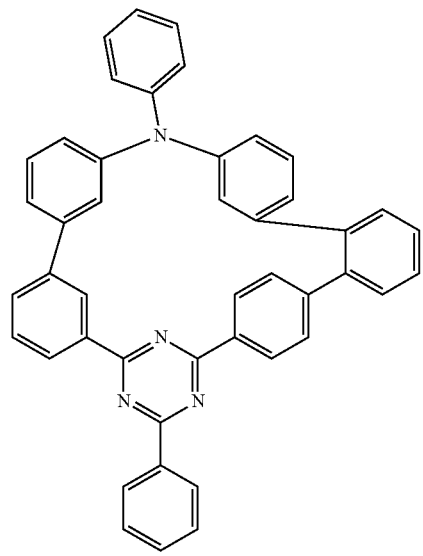 [SMILES: c1ccc(-c2nc3nc(n2)-c2cccc(c2)-c2cccc(c2)N(c2ccccc2)c2cccc(c2)-c2ccccc2-c2ccc-3cc2)cc1]
10
Example Compound 11
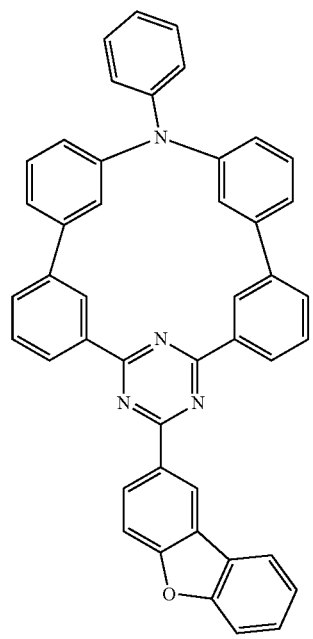 [SMILES: c1ccc(N2c3cccc(c3)-c3cccc(c3)-c3nc(nc(-c4ccc5oc6ccccc6c5c4)n3)-c3cccc(c3)-c3cccc2c3)cc1]
11

TABLE 1-continued
Example Compound 12
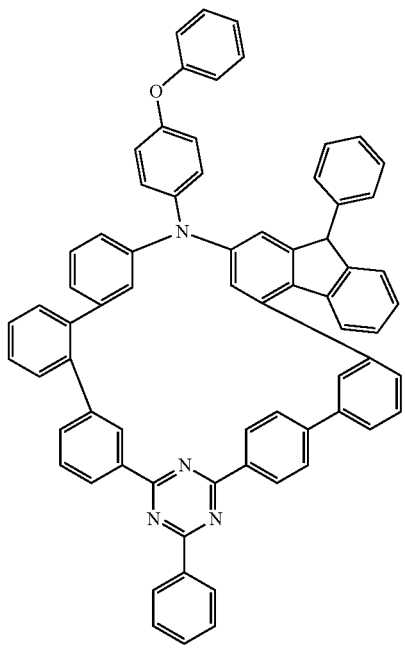 [SMILES: c1ccc(Oc2ccc(N3c4cccc(c4)-c4ccccc4-c4cccc(c4)-c4nc(-c5ccccc5)nc(n4)-c4ccc(cc4)-c4cccc(c4)-c4cc3cc3c4-c4ccccc4C3c3ccccc3)cc2)cc1]
12
Example Compound 13
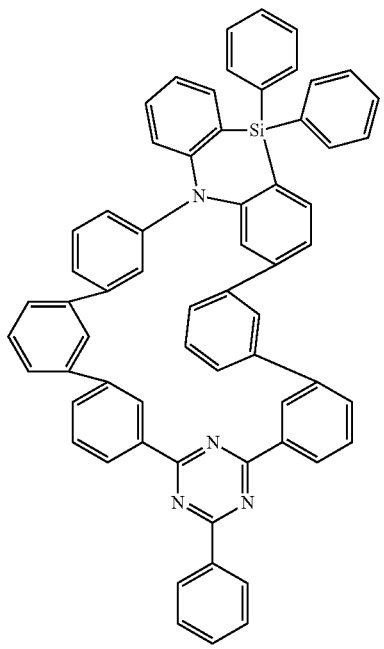 [SMILES: c1ccc(-c2nc3nc(n2)-c2cccc(c2)-c2cccc(c2)-c2ccc4c(c2)N(c2cccc(c2)-c2cccc(c2)-c2cccc-3c2)c2ccccc2[Si]4(c2ccccc2)c2ccccc2)cc1]
13
TABLE 2
| Compound | S1 energy level | T1 energy level | $\Delta E_{ST}$ |
|---|---|---|---|
| Example Compound 1 | 2.96 | 2.90 | 0.06 |
| Example Compound 2 | 2.86 | 2.79 | 0.07 |
| Example Compound 3 | 2.81 | 2.75 | 0.06 |
| Example Compound 4 | 2.86 | 2.79 | 0.07 |
| Example Compound 5 | 2.85 | 2.78 | 0.07 |
| Example Compound 6 | 2.78 | 2.63 | 0.15 |
| Example Compound 7 | 2.84 | 2.78 | 0.06 |
| Example Compound 8 | 2.85 | 2.78 | 0.07 |
| Example Compound 9 | 2.76 | 2.70 | 0.06 |
| Example Compound 10 | 2.83 | 2.75 | 0.06 |
| Example Compound 11 | 2.85 | 2.78 | 0.07 |
| Example Compound 12 | 2.52 | 2.50 | 0.02 |

TABLE 2-continued

| Compound | S1 energy level | T1 energy level | $\Delta E_{ST}$ |
|---|---|---|---|
| Example Compound 13 | 2.98 | 2.98 | 0.00 |
| Comparative Compound X-1 | 3.06 | 2.76 | 0.30 |
| Comparative Compound X-2 | 3.18 | 2.78 | 0.40 |
| Comparative Compound X-3 | 3.88 | 2.97 | 0.91 |
| Comparative Compound X-4 | 2.71 | 2.16 | 0.55 |

Referring to Table 2, each of the example compounds were found to have smaller $\Delta E_{ST}$ values than all of the comparative compounds. Example Compounds 1 to 13 were found to have $\Delta E_{ST}$ values of about 0.2 eV or less. In comparison, Comparative Compounds X-1 to X-4 were found to have $\Delta E_{ST}$ values greater than about 0.2 eV, which is different from (e.g., larger than) the example compounds.

Accordingly, the example compounds have a cyclic structure different from the comparative compounds (e.g., the amine group that may act as an electron donor is cyclically linked through two or more rings with the azine group that may act as an electron acceptor), and also have effectively separated HOMO and LUMO levels (e.g., have a high degree of HOMO and LUMO spatial separation, and/or a lower degree of HOMO and LUMO orbital overlap) when compared to the comparative examples, resulting in small $\Delta E_{ST}$ values.

3. Manufacture and Evaluation of Organic Electroluminescence Devices Including a Nitrogen-Containing Compounds
Manufacture of Organic Electroluminescence Device An organic electroluminescence device according to an embodiment of the present disclosure, in which a nitrogen-containing compound according to an embodiment of the present disclosure and a delayed fluorescence emitting component are included in an emission layer was manufactured by the method described below. A case in which an emission layer of an organic electroluminescence device according to an embodiment of the present disclosure includes a nitrogen-containing compound as a fluorescence dopant, will be explained as illustration.

Organic electroluminescence devices according to Examples 1 to 5 were manufactured using the nitrogen-containing compounds of Compound 1, Compound 2, Compound 3, Compound 4, and Compound 11, respectively, as emission layer materials; and organic electroluminescence devices according to Comparative Examples 1 to 4 were manufactured using Comparative Compound X-1 to X-4, respectively, as emission layer materials.

On a glass substrate, ITO was patterned to a thickness of about 1,500 Å and washed with ultra-pure water, and a UV ozone treatment was conducted for about 10 minutes. Then, HAT-CN was deposited to a thickness of about 100 Å, α-NPD was deposited to a thickness of about 800 Å, and mCP was deposited to a thickness of about 50 Å to form a hole transport region.

Then, the nitrogen-containing compound according to an embodiment of the present disclosure or the comparative compound was co-deposited with DPEPO in a ratio of 18:82 during formation of an emission layer to a thickness of about 200 Å. For example, the emission layer formed by the co-deposition was obtained by depositing a mixture of each of Compound 1, Compound 2, Compound 3, Compound 4, or Compound 11 with DPEPO in Example 1 to Example 5, respectively, or by depositing a mixture of each of Comparative Compounds X-1, X-2, X-3, or X-4 with DPEPO in Comparative Example 1 to Comparative Example 4, respectively.

After forming the emission layer, a layer was formed using DPEPO to a thickness of about 100 Å. Then, a layer was formed using TPBi to a thickness of about 300 Å, and an electron transport region layer was formed using LiF to a thickness of about 5 Å. Then, a second electrode was formed using aluminum (Al) to a thickness of about 1000 Å.

In an embodiment of the present disclosure, a hole transport region, an emission layer, an electron transport region, and a second electrode were formed using a vacuum deposition apparatus.

The materials utilized for the manufacture of the organic electroluminescence devices may be represented by the following formulae:

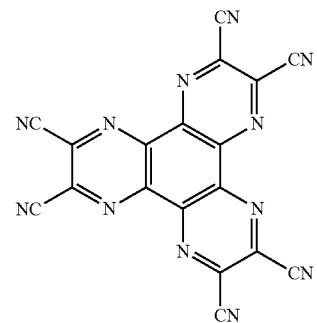

HAT-CN

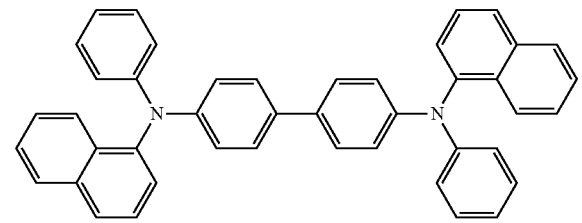

α-NOA

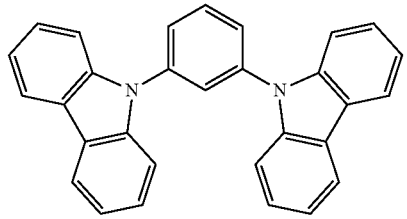

mCP

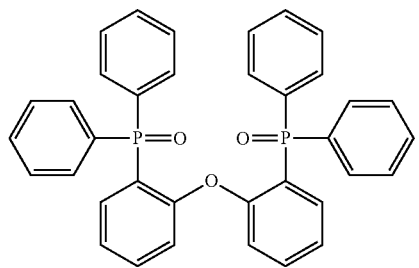

DPEPO

-continued

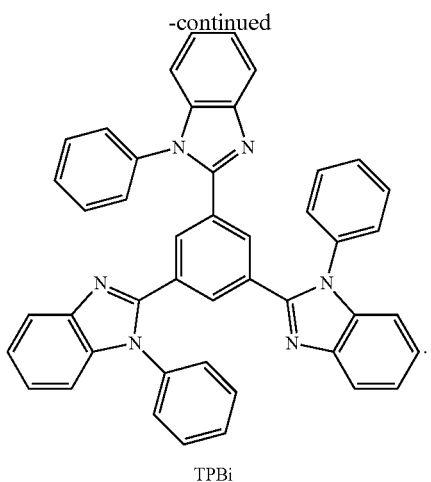

TPBi

Evaluation of Properties of Organic Electroluminescence Device

In Table 3, the evaluation results of the organic electroluminescence devices of Examples 1 to 5 and Comparative Examples 1 to 4 are shown. In Table 3, $\lambda_{max}$ represents the maximum emission wavelength of light emitted from an organic electroluminescence device, and $\eta_{ext}$ represents external quantum efficiency. The emission properties of the organic electroluminescence devices according to the Examples and the Comparative Examples were measured using a C9920-12 brightness light distribution characteristics measurement system (HAMAMATSU Photonics Co., Ltd., Hamamatsu, Japan).

TABLE 3

| Device manufacturing example | Dopant material | $\lambda_{max}$ (nm) | $\eta_{ext}$ (%) |
|---|---|---|---|
| Example 1 | Compound 1 | 456 | 8.3 |
| Example 2 | Compound 2 | 479 | 10.6 |
| Example 3 | Compound 3 | 483 | 11.5 |
| Example 4 | Compound 4 | 482 | 12.6 |
| Example 5 | Compound 11 | 468 | 10.3 |
| Comparative Example 1 | Comparative Compound X-1 | 482 | 2.5 |
| Comparative Example 2 | Comparative Compound X-2 | 476 | 2.2 |
| Comparative Example 3 | Comparative Compound X-3 | 412 | 1.6 |
| Comparative Example 4 | Comparative Compound X-4 | 435 | 3.7 |

Referring to the results of Table 3, it was found that the examples of the organic electroluminescence devices using the nitrogen-containing compound according to an embodiment of the present disclosure as a material in the emission layer, showed high external quantum efficiencies in the blue emission region. For example, the organic electroluminescence devices according to Examples 1 to 5 were found to have maximum emission wavelengths of about 450 nm to about 490 nm, and the organic electroluminescence devices according to Examples 1 to 5 were found to emit blue light.

In addition, it was found that the organic electroluminescence devices according to Example 1 to Example 5 showed higher external quantum efficiency than the organic electroluminescence devices according to Comparative Example 1 to Comparative Example 4. As in the evaluation results of Table 2, when the nitrogen-containing compound according to an embodiment of the present disclosure has an appropriate or suitable cyclic molecular structure, a small $\Delta E_{ST}$ value may be obtained, and from the results, it may be found that an organic electroluminescence device according to an embodiment of the present disclosure, including a nitrogen-containing compound according to an embodiment of the present disclosure in the emission layer may exhibit thermally activated delayed fluorescence emission and show improved external quantum efficiency. In comparison, in the Comparative Examples, since the comparative compounds utilized in the emission layer did not have a small $\Delta E_{ST}$ values (which is connected to exhibiting thermally delayed fluorescence), the external quantum efficiency was low.

For example, the emission efficiency of an organic electroluminescence device may be improved by using the nitrogen-containing compound according to an embodiment of the present disclosure in the emission layer.

A nitrogen-containing compound according to an embodiment of the present disclosure has a cyclic molecular structure including a nitrogen atom, and exhibits thermally and/or chemically stable properties. In addition, when the nitrogen-containing compound according to an embodiment of the present disclosure has an aryl amine moiety and an azine moiety (e.g., triazine or pyrimidine) in the cyclic molecular structure, the HOMO and LUMO of a molecule may be effectively separated (e.g., spatially separated), resulting in a small $\Delta E_{ST}$ value, and the nitrogen-containing compound may be utilized as a material for emitting delayed fluorescence.

The organic electroluminescence device according to an embodiment of the present disclosure includes a nitrogen-containing compound according to an embodiment of the present disclosure in an emission layer, and may exhibit thermally activated delayed fluorescence emission, thereby enabling improved emission efficiency.

The nitrogen-containing compound according to an embodiment of the present disclosure may improve the emission efficiency of an organic electroluminescence device.

The organic electroluminescence device according to an embodiment of the present disclosure may include the nitrogen-containing compound according to an embodiment of the present disclosure in an emission layer, and may achieve high efficiency.

As used herein, expressions such as "at least one of", "one of", and "selected from", when preceding a list of elements, modify the entire list of elements and do not modify the individual elements of the list. Further, the use of "may" when describing embodiments of the present disclosure refers to "one or more embodiments of the present disclosure".

In addition, as used herein, the terms "use", "using", and "used" may be considered synonymous with the terms "utilize", "utilizing", and "utilized", respectively.

As used herein, the terms "substantially", "about", and similar terms are used as terms of approximation and not as terms of degree, and are intended to account for the inherent deviations in measured or calculated values that would be recognized by those of ordinary skill in the art.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although the example embodiments of the present disclosure have been described, it is understood that the present disclosure should not be limited to these example embodiments but various changes and modifications can be made by one ordinary skilled in the art within the spirit and scope of the present disclosure as defined by the following claims and equivalents thereof.

The invention claimed is:

1. A nitrogen-containing compound represented by Formula 1:

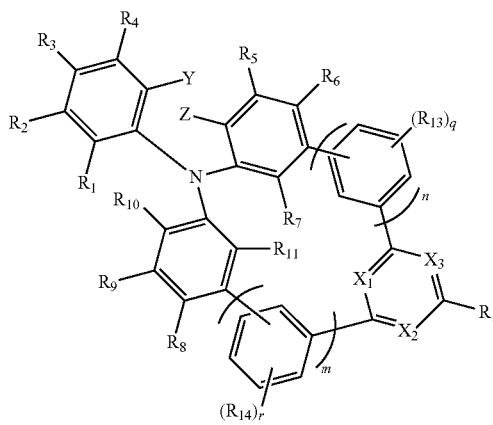

Formula 1 wherein in Formula 1,
at least two of $X_1$, $X_2$ or $X_3$ are N, and the remainder thereof is $CR_{15}$,
Y and Z are each independently a hydrogen atom, a deuterium atom, $OR_{16}$, $SR_{17}$, $CR_{18}R_{19}R_{20}$, or $SiR_{21}R_{22}R_{23}$, or combined with each other to form a ring,
$R_1$ to $R_{14}$ are each independently a hydrogen atom, a deuterium atom, $OR_{24}$, $SR_{25}$, (C=O)$R_{26}$, $NR_{27}R_{28}$, $CR_{29}R_{30}R_{31}$, $SiR_{32}R_{33}R_{34}$, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring,
wherein adjacent ones of $R_1$ to $R_4$ are optionally combined to form a ring, $R_5$ and $R_6$ are optionally combined to form a ring, adjacent ones of $R_8$ to $R_{10}$ are optionally combined to form a ring, adjacent ones of $R_{13}$ are optionally combined to form a ring, and adjacent ones of $R_{14}$ are optionally combined to form a ring, and
$R_{15}$ to $R_{34}$ are each independently a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, or combined with an adjacent group to form a ring,
n and m are each independently 1 or 2, and
q and r are each independently an integer of 0 to 4.

2. The nitrogen-containing compound of claim 1, wherein $X_1$ is N, and at least one of $X_2$ or $X_3$ is N.

3. The nitrogen-containing compound of claim 1, wherein n and m are 1.

4. The nitrogen-containing compound of claim 1, wherein m is 1, and n is 1 or 2.

5. The nitrogen-containing compound of claim 1, wherein $R_{12}$ is a substituted or unsubstituted phenyl group, or a substituted or unsubstituted dibenzofuran group.

6. The nitrogen-containing compound of claim 1, wherein Formula 1 is represented by Formula 1-1 or Formula 1-2:

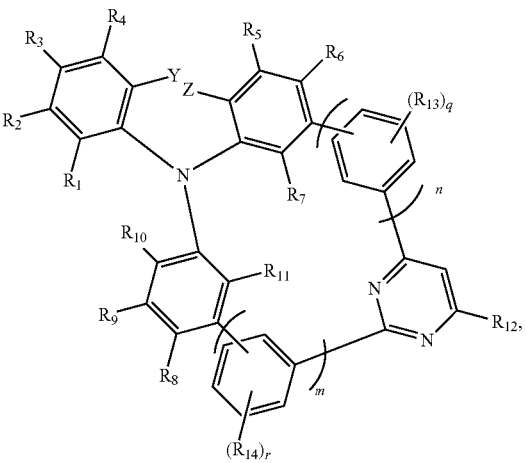

Formula 1-1

Formula 1-2 wherein in Formula 1-1 and Formula 1-2, Y, Z, n, m, $R_1$ to $R_{34}$, q9, and rare each independently the same as defined in Formula 1.

7. The nitrogen-containing compound of claim 1, wherein Formula 1 is represented by Formula 1-3 or Formula 1-4:

8. The nitrogen-containing compound of claim 1, wherein Formula 1 is represented by Formula 1-5 or Formula 1-6:

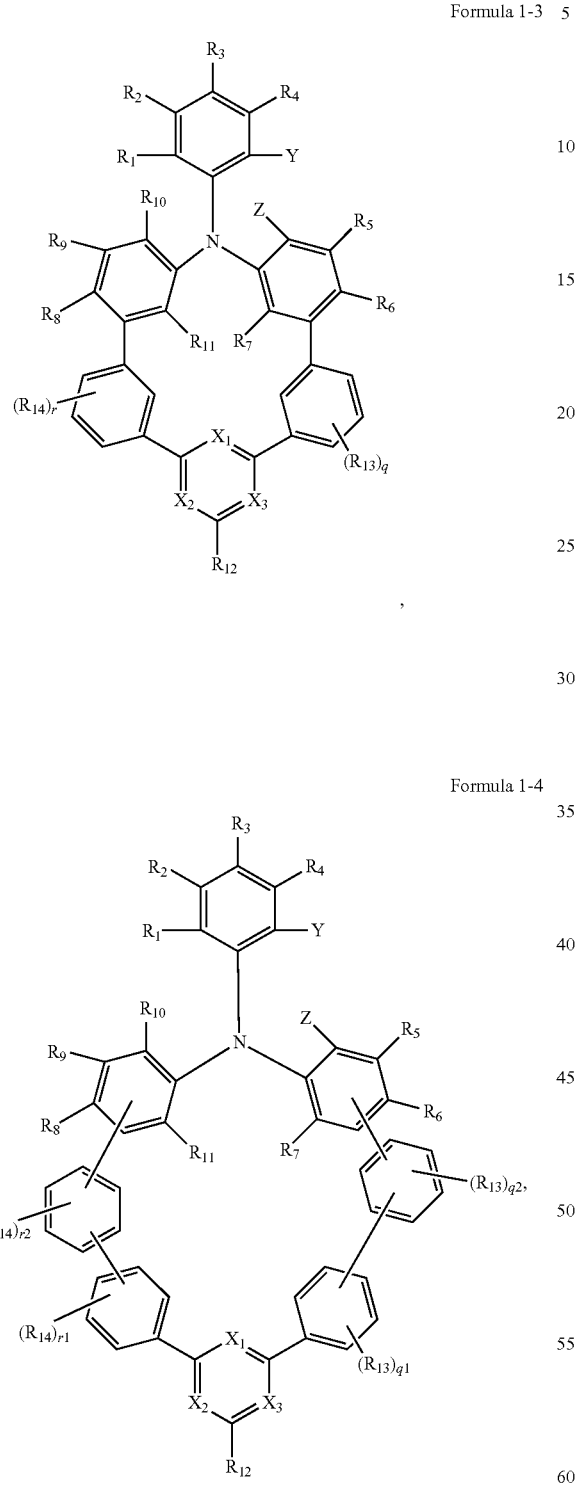

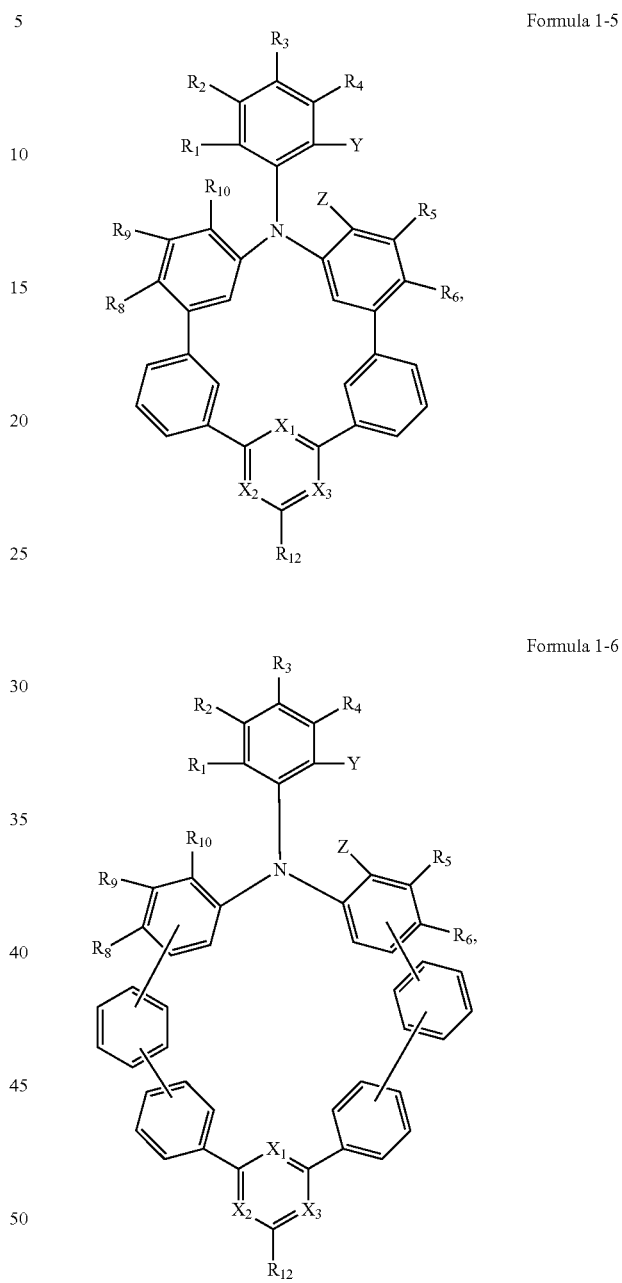

wherein in Formula 1-4, q1, q2, r1, and r2 are each independently an integer of 0 to 4, and in Formula 1-3 and Formula 1-4, $X_1$ to $X_3$, Y, Z, $R_1$ to $R_{34}$, q, and r are each independently the same as defined in Formula 1.

wherein in Formula 1-5 and Formula 1-6, $X_1$ to $X_3$, Y, Z, $R_1$ to $R_6$, $R_8$, $R_9$, $R_{10}$ and $R_{12}$ are each independently the same as defined in Formula 1.

9. The nitrogen-containing compound of claim 1, wherein the nitrogen-containing compound represented by Formula 1 has a difference between the lowest excitation singlet energy level (S1) and the lowest excitation triplet energy level (T1) of about 0.2 eV or less.

10. The nitrogen-containing compound of claim 1, wherein the nitrogen-containing compound represented by Formula 1 is a thermally activated delayed fluorescence emission material.

11. The nitrogen-containing compound of claim 1, wherein the nitrogen-containing compound represented by Formula 1 is a compound represented in Compound Group 1:
Compound Group 1
1
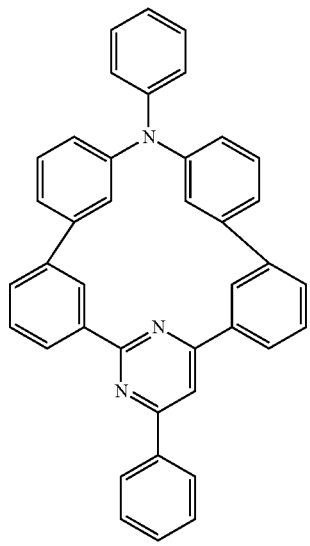
2
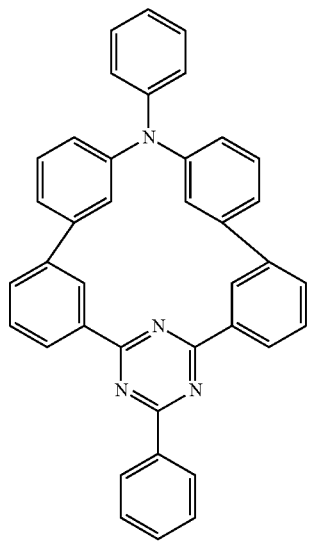
3
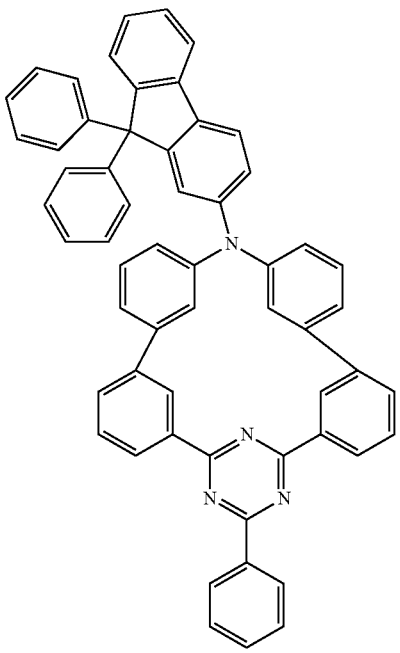
4
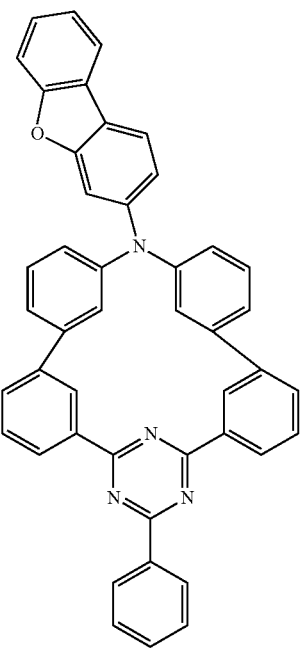

139
-continued
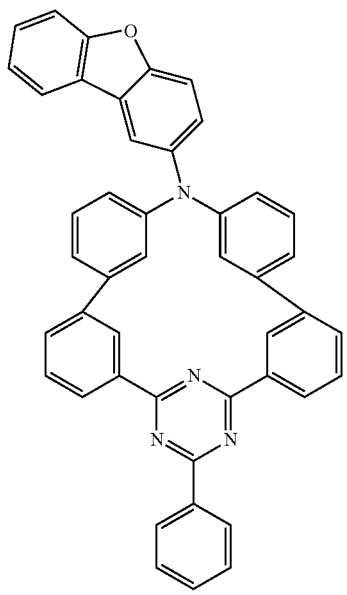
5
140
-continued
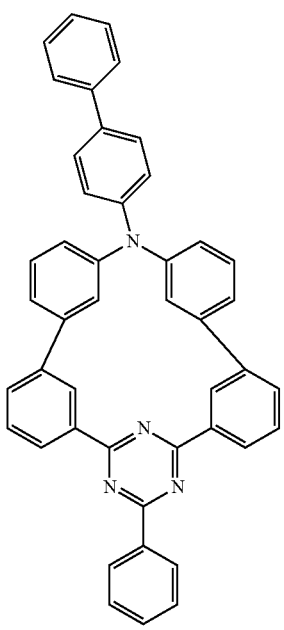
7
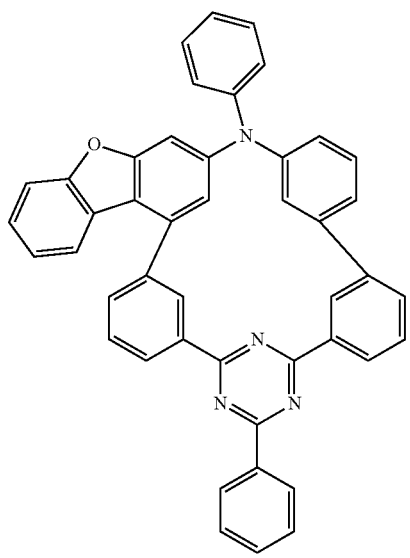
6
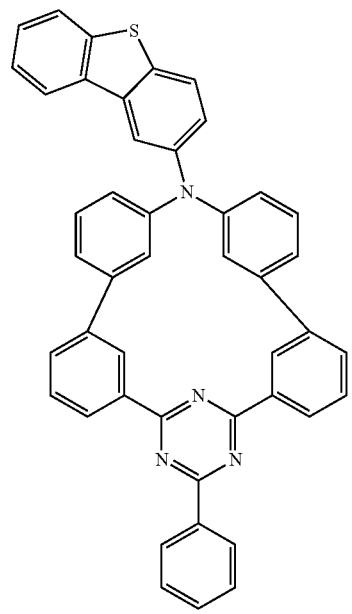
8

9
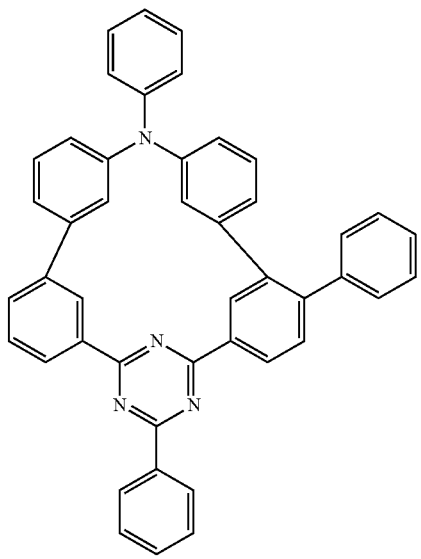
11
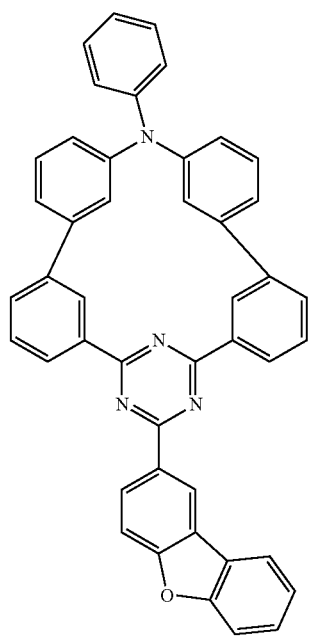
10
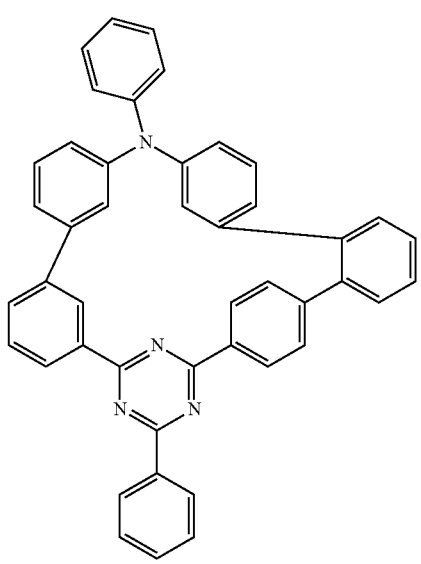
12
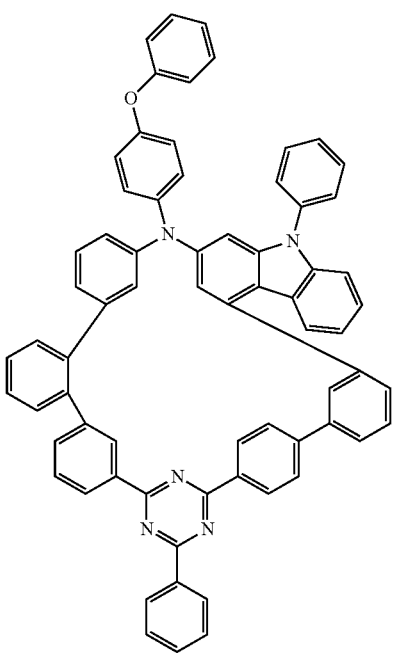

13
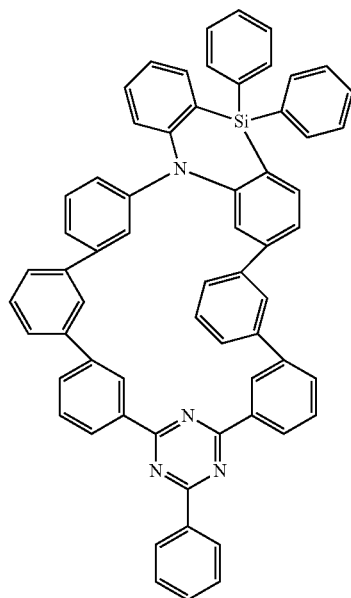
14
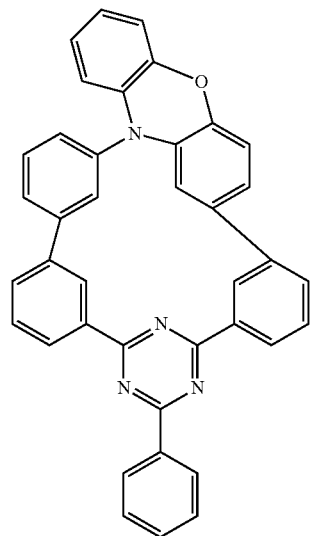
15
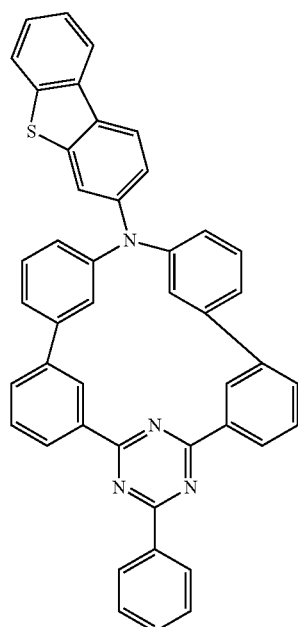
16
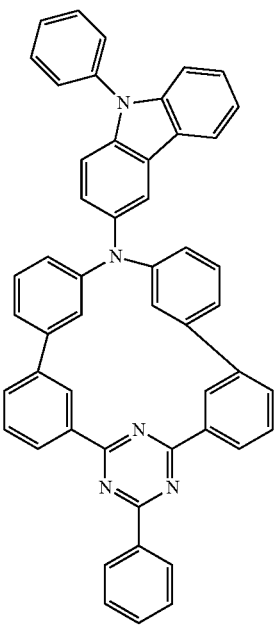

145
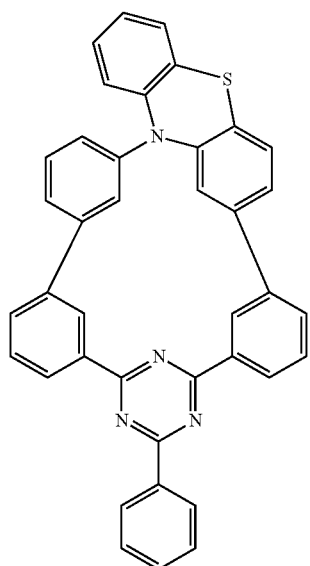
146
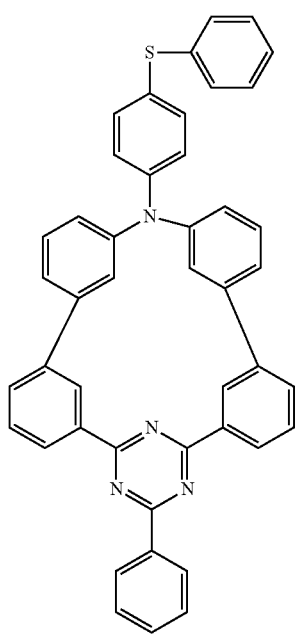
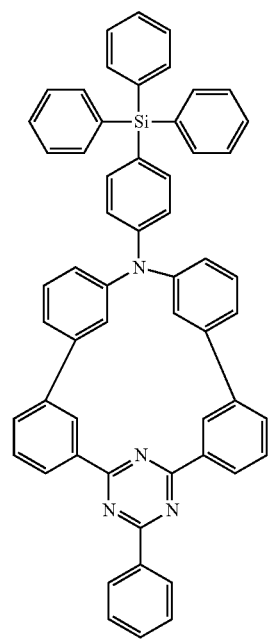
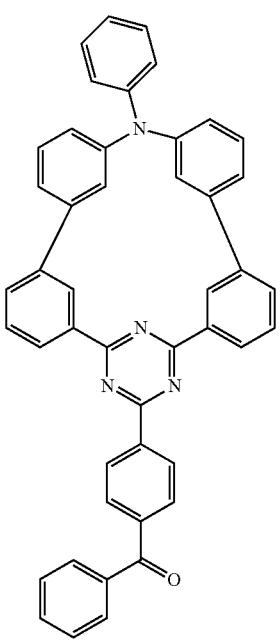

21
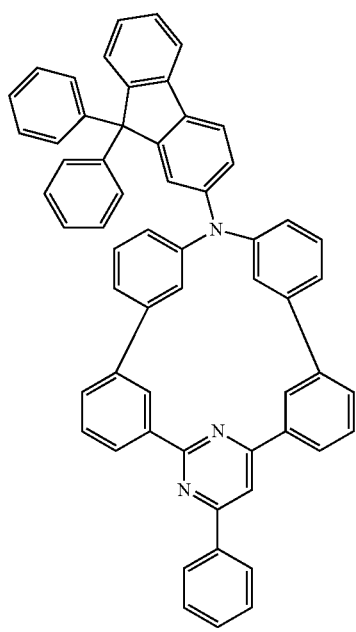
22
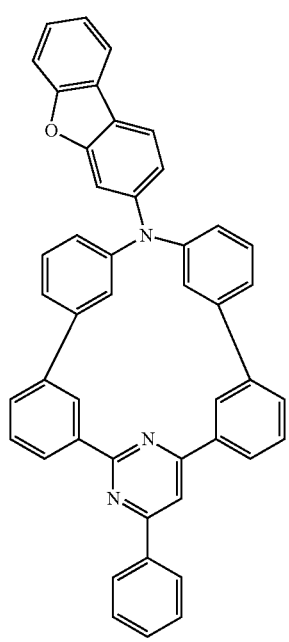
23
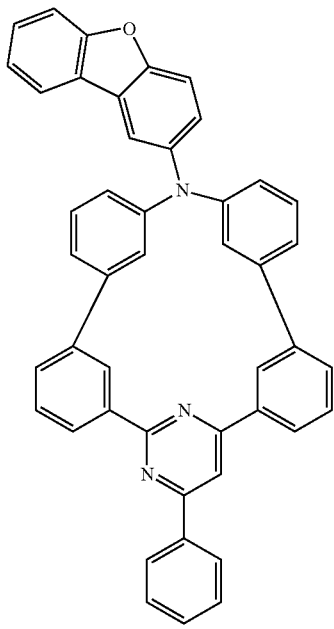
24
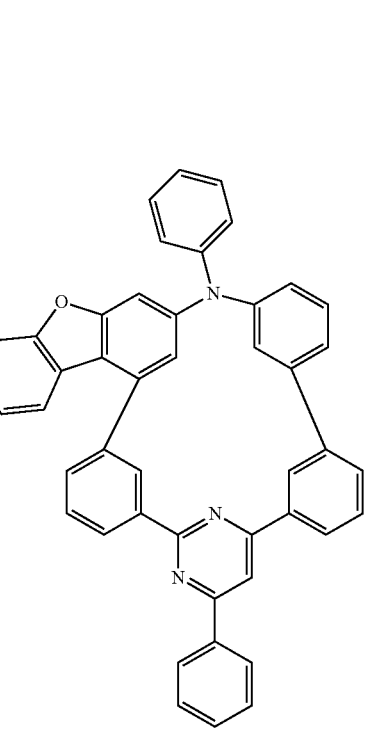

149
25
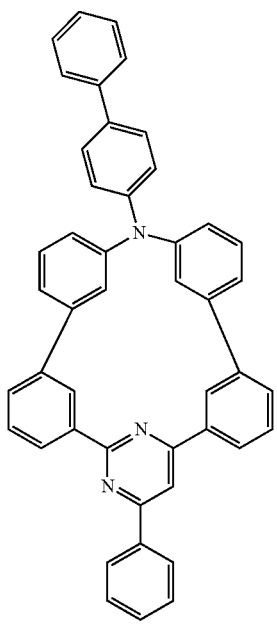
150
27
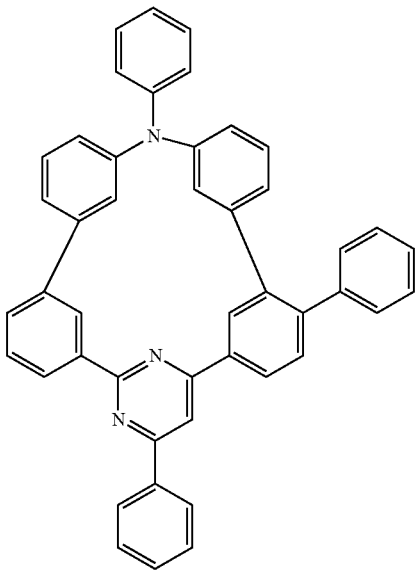
26
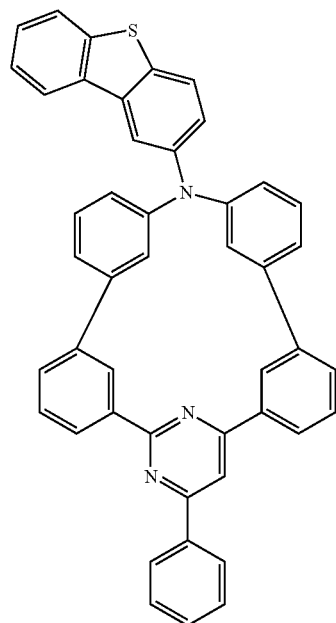
28
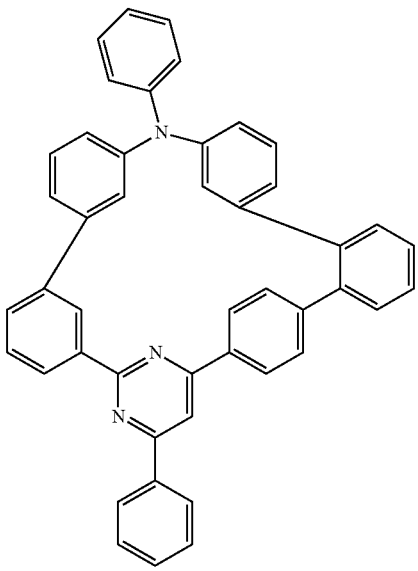

151
-continued
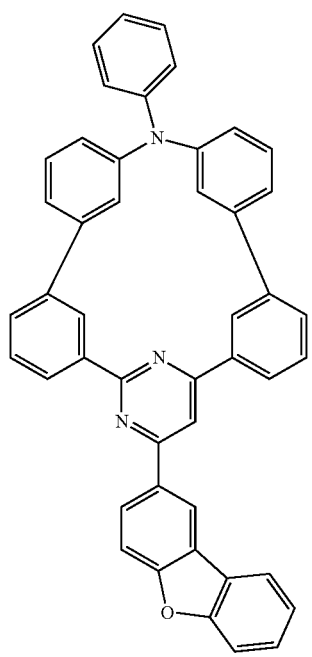
152
-continued
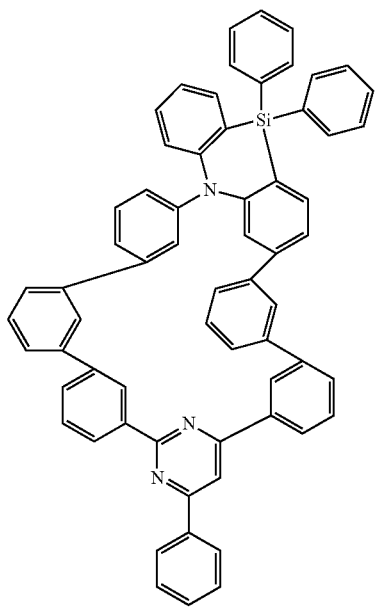

33
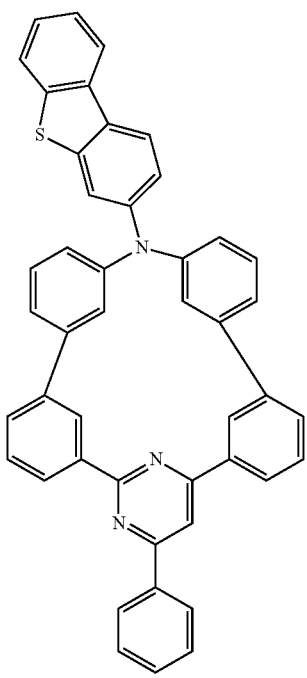
34
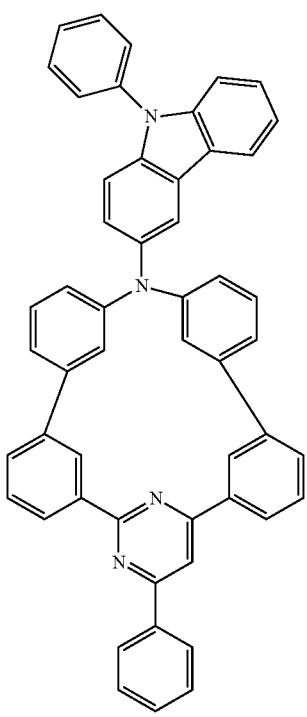
35
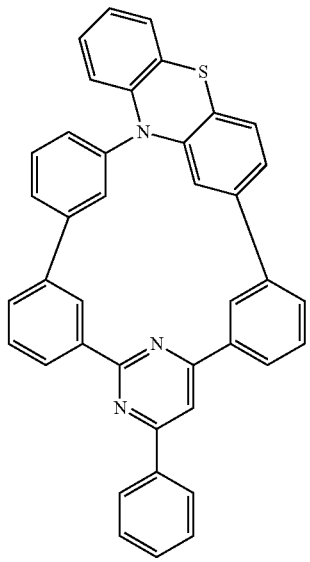
36
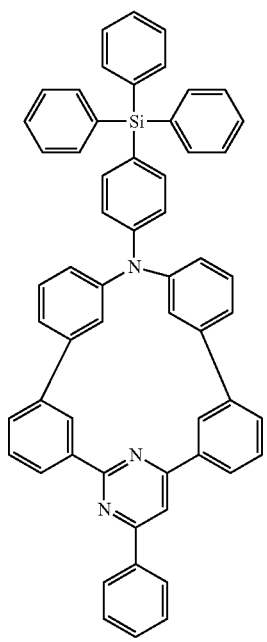

-continued

37

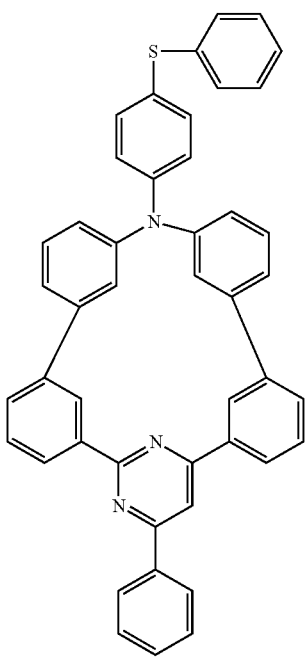

38

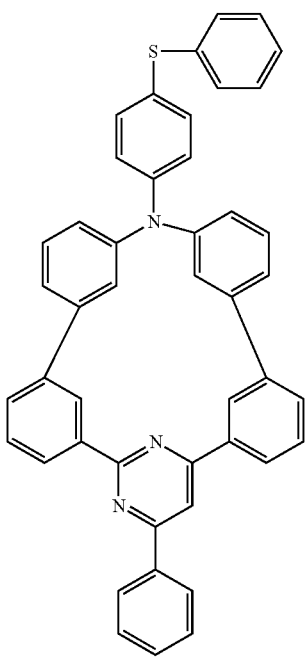

12. An organic electroluminescence device, comprising:
a first electrode;
a hole transport region on the first electrode;
an emission layer on the hole transport region and comprising a nitrogen-containing compound represented by Formula 1;
an electron transport region on the emission layer; and
a second electrode on the electron transport region,
wherein the first electrode and the second electrode each independently comprise at least one selected from Ag, Mg, Cu, Al, Pt, Pd, Au, Ni, Nd, Ir, Cr, Li, Ca, LiF/Ca, LiF/Al, Mo, Ti, In, Sn, and Zn, a compound of two or more thereof, a mixture of two or more thereof, and an oxide thereof:

Formula 1

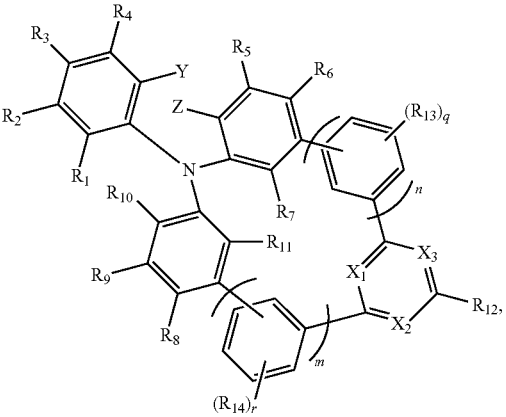

wherein in Formula 1, at least two of $X_1$, $X_2$ or $X_3$ are N, and the remainder thereof is $CR_{15}$, Y and Z are each independently a hydrogen atom, a deuterium atom, $OR_{16}$, $SR_{17}$, $CR_{18}R_{19}R_{20}$, or $SiR_{21}R_{22}R_{23}$, or combined with each other to form a ring, $R_1$ to $R_{14}$ are each independently a hydrogen atom, a deuterium atom, $OR_{24}$, $SR_{25}$, $(C=O)R_{26}$, $NR_{27}R_{28}$, $CR_{29}R_{30}R_{31}$, $SiR_{32}R_{33}R_{34}$, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, wherein adjacent ones of $R_1$ to $R_4$ are optionally combined to form a ring, $R_5$ and $R_6$ are optionally combined to form a ring, adjacent ones of $R_8$ to $R_{10}$ are optionally combined to form a ring, adjacent ones of $R_{13}$ are optionally combined to form a ring, and adjacent ones $R_{14}$ are optionally combined to form a ring, $R_{15}$ to $R_{34}$ are each independently a hydrogen atom, a deuterium atom, a halogen atom, a cyano group, a substituted or unsubstituted silyl group, a substituted or unsubstituted alkyl group having 1 to 20 carbon atoms, a substituted or unsubstituted aryl group having 6 to 30 carbon atoms for forming a ring, or a substituted or unsubstituted heteroaryl group having 2 to 30 carbon atoms for forming a ring, or combined with an adjacent group to form a ring, n and m are each independently 1 or 2, and q and r are each independently an integer of 0 to 4.

13. The organic electroluminescence device of claim 12, wherein the nitrogen-containing compound represented by Formula 1 is represented by Formula 1-1 or Formula 1-2:

Formula 1-1

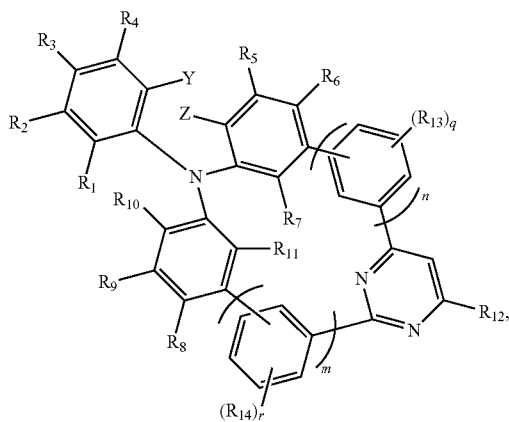

Formula 1-2

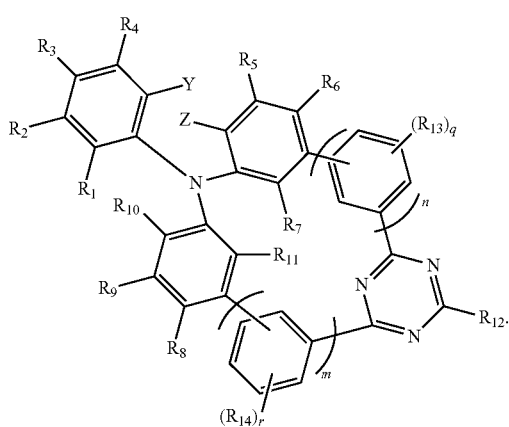

wherein in Formula 1-1 and Formula 1-2, Y, Z, n, m, $R_1$ to $R_{34}$, q, and r are each independently the same as defined in Formula 1.

14. The organic electroluminescence device of claim 12, wherein Formula 1 is represented by Formula 1-3 or Formula 1-4:

Formula 1-3

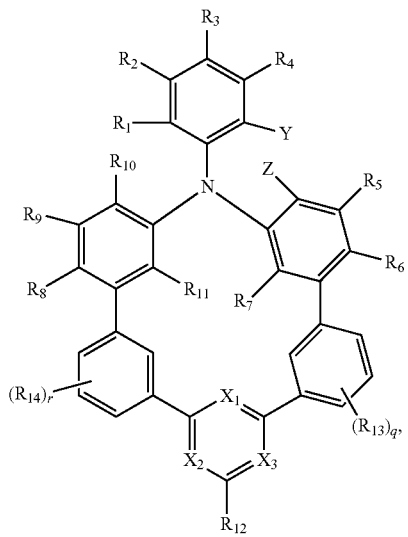

Formula 1-4

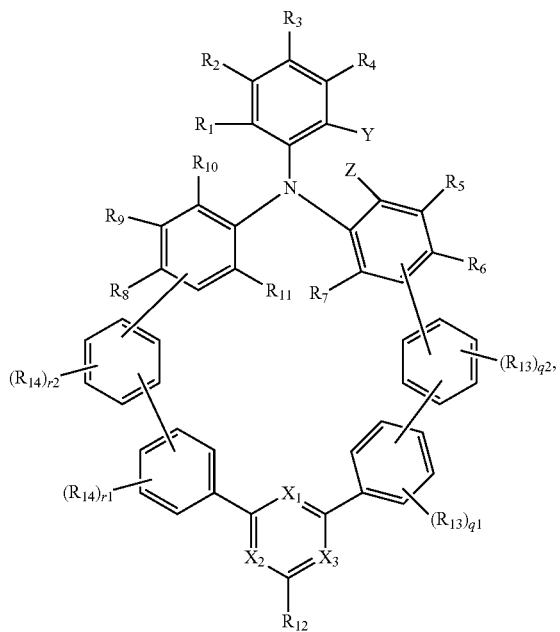

wherein in Formula 1-4, q1, q2, r1, and r2 are each independently an integer of 0 to 4, and in Formula 1-3 and Formula 1-4, $X_1$ to $X_3$, Y, Z, $R_1$ to $R_{34}$, q, and r are each independently the same as defined in Formula 1.

15. The organic electroluminescence device of claim 12, wherein Formula 1 is represented by Formula 1-5 or Formula 1-6:

Formula 1-5

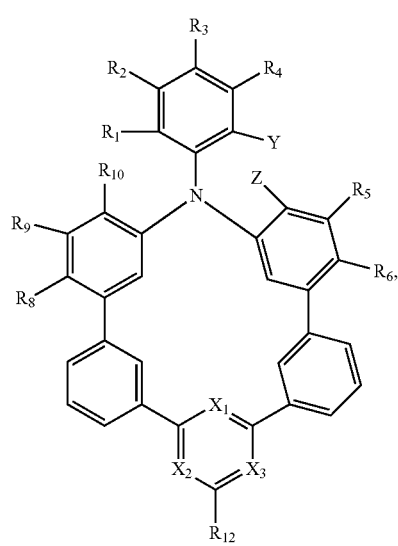

-continued

Formula 1-6

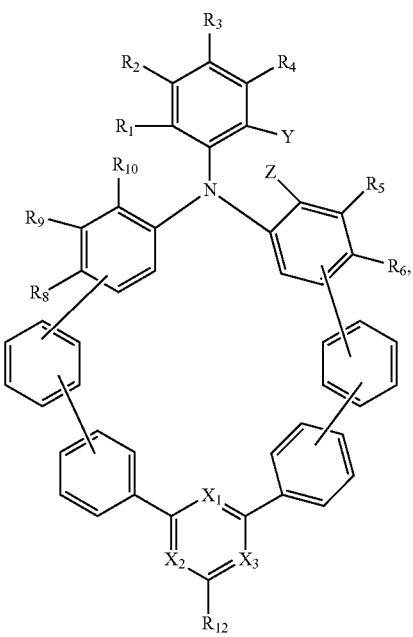

wherein in Formula 1-5 and Formula 1-6, $X_1$ to $X_3$, Y, Z, $R_1$ to $R_6$, $R_8$, $R_9$, $R_{10}$ and $R_{12}$ are each independently the same as defined in Formula 1.

16. The organic electroluminescence device of claim 12, wherein the emission layer is to emit delayed fluorescence.

17. The organic electroluminescence device of claim 12, wherein the emission layer is an emission layer of a thermally activated delayed fluorescence, the emission layer being to emit blue light.

18. The organic electroluminescence device of claim 12, wherein the emission layer comprises a host and a dopant, and
   the dopant is the nitrogen-containing compound represented by Formula 1.

19. The organic electroluminescence device of claim 18, wherein the host comprises at least one of bis[2-(diphenylphosphino)phenyl] ether oxide (DPEPO), 4,4'-bis(carbazol-9-yl)biphenyl (CBP), 1,3-bis(carbazol-9-yl)benzene (mCP), 2,8-bis(diphenylphosphoryl)dibenzo[b,d]furan (PPF), 4,4',4''-tris(carbazol-9-yl)-triphenylamine (TcTa), 1,3,5-tris(N-phenylbenzimidazole-2-yl)benzene (TPBi), 3,3'-di(9H-carbazol-9-yl)-1,1'-biphenyl (mCBP), and (2,4,6-tris(biphenyl-3-yl)-1,3,5-triazine (T2T).

20. The organic electroluminescence device of claim 12, wherein the emission layer comprises at least one nitrogen-containing compound represented in Compound Group 1:

Compound Group 1

1

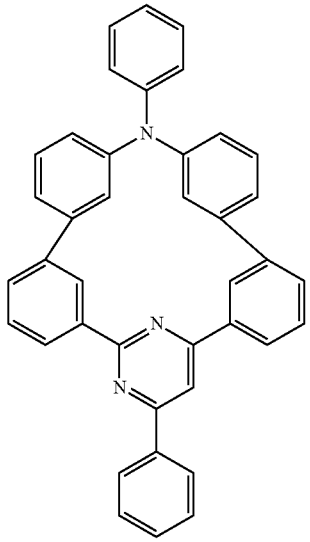

2

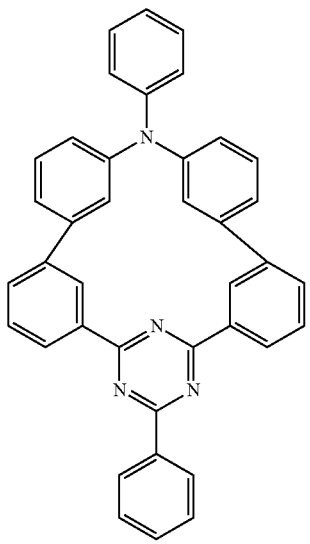

161
-continued
3
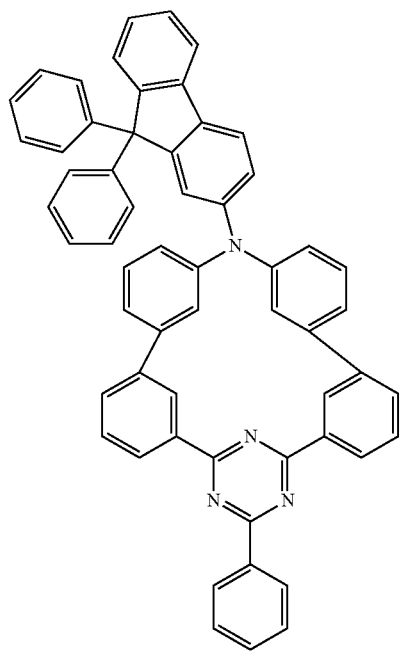
162
-continued
5
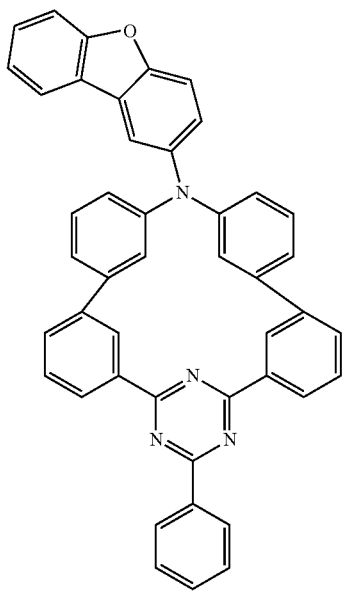
4
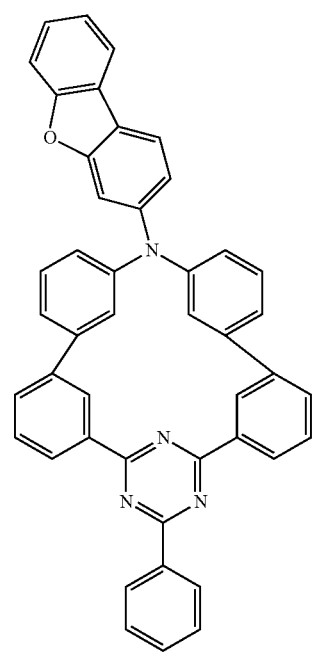
6
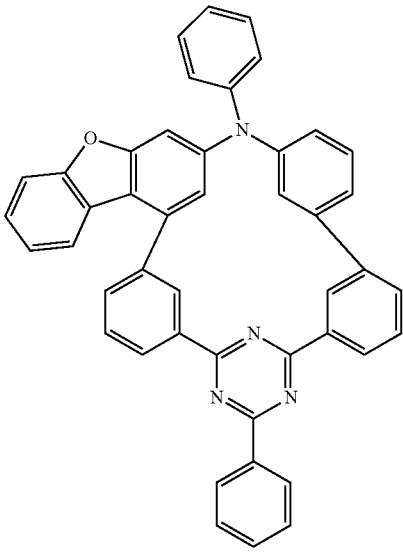

7
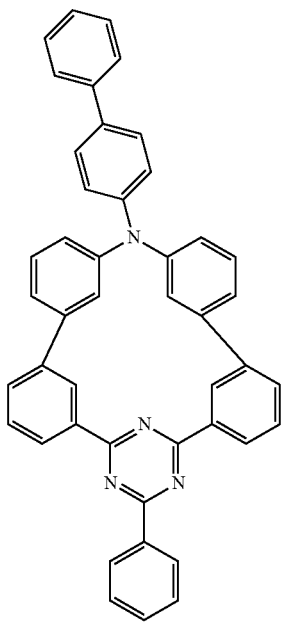
9
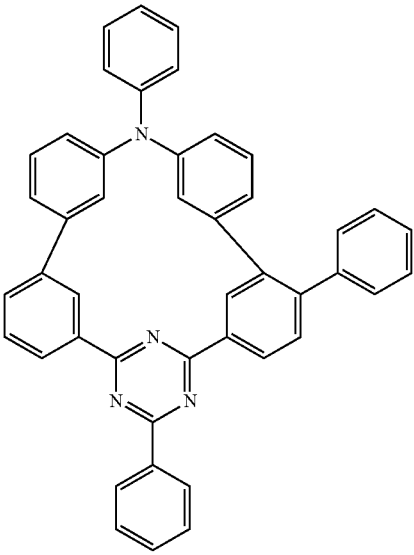
8
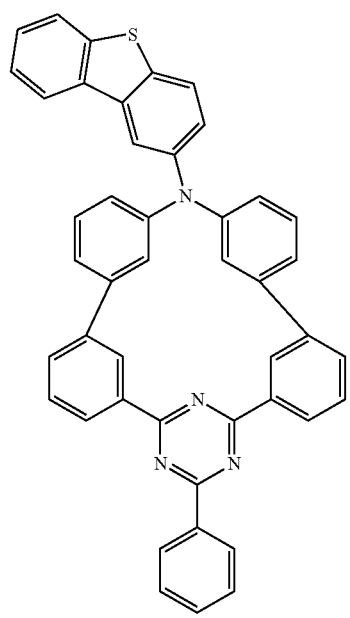
10
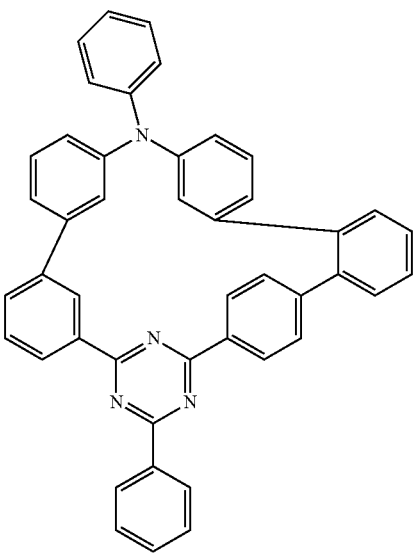

11
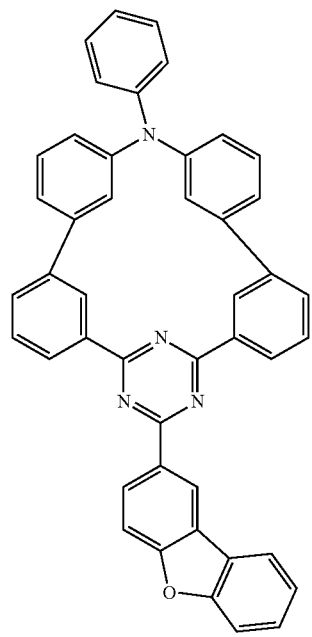
13
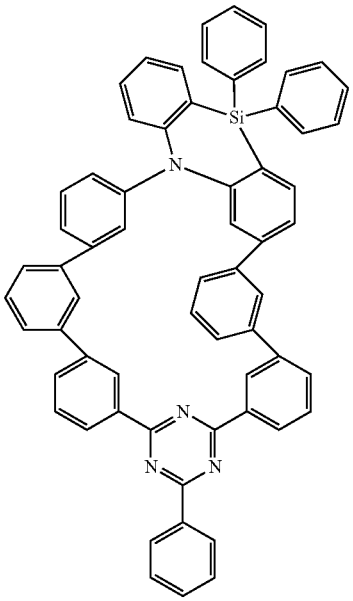
12
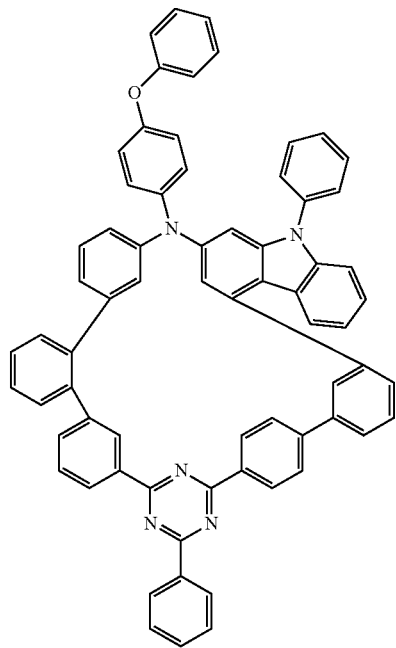
14
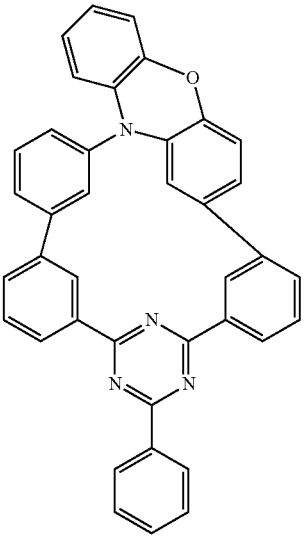

167
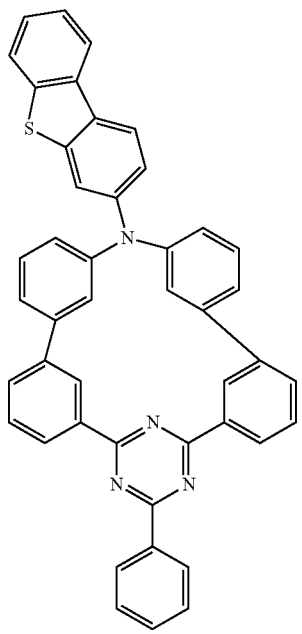
168
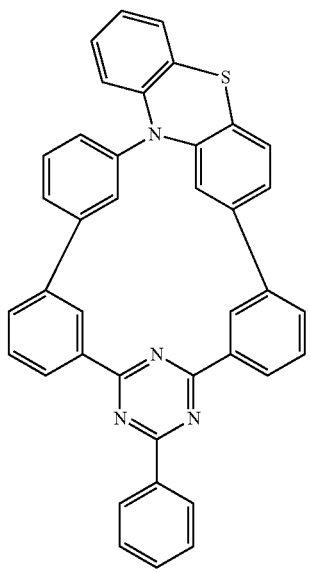
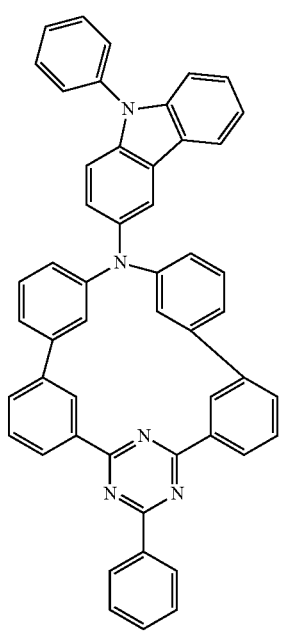
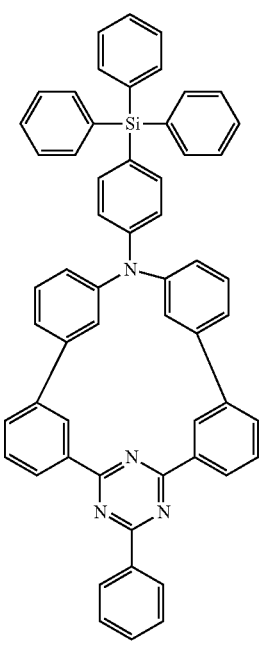

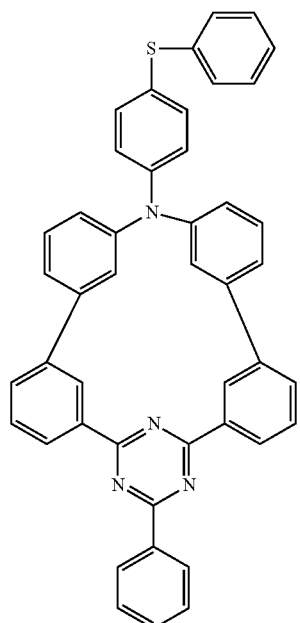
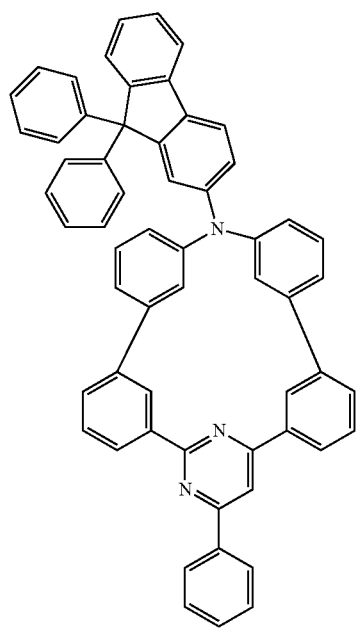
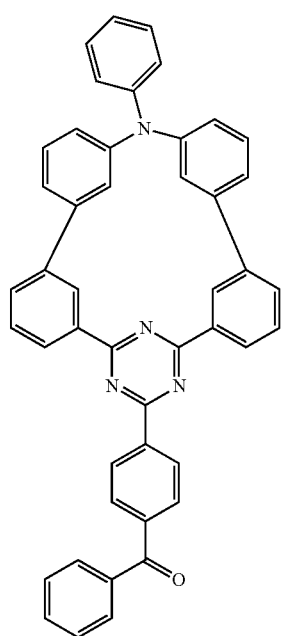
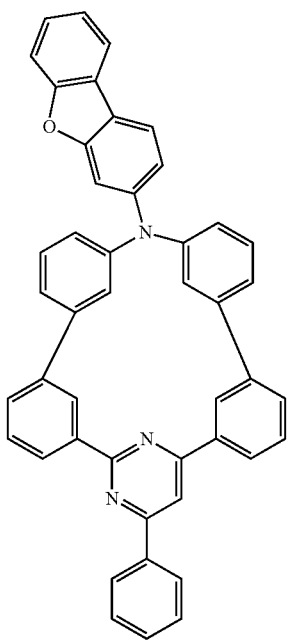

23
24
25
26
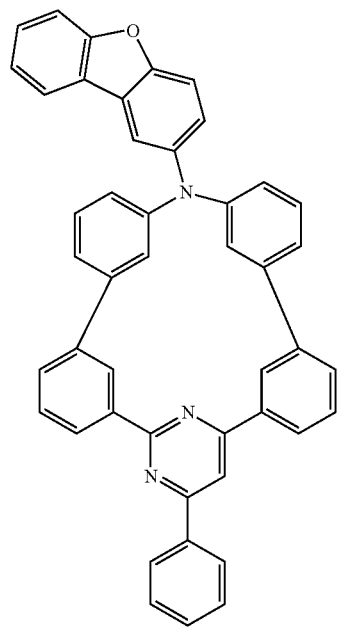
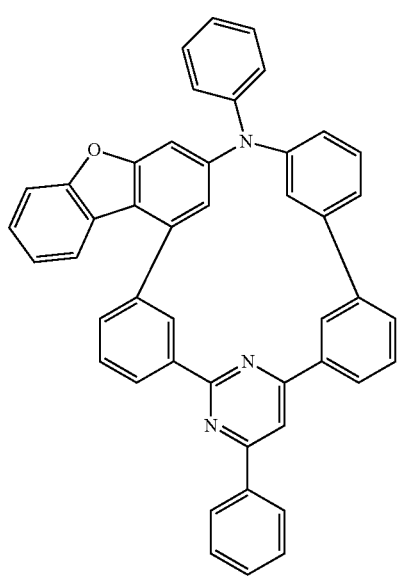
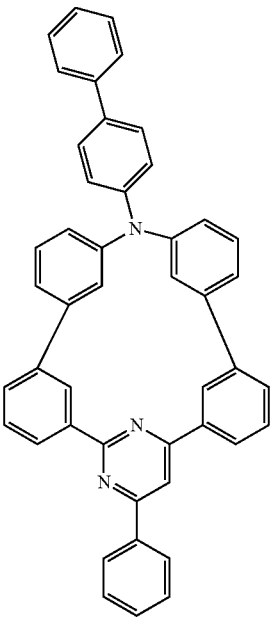
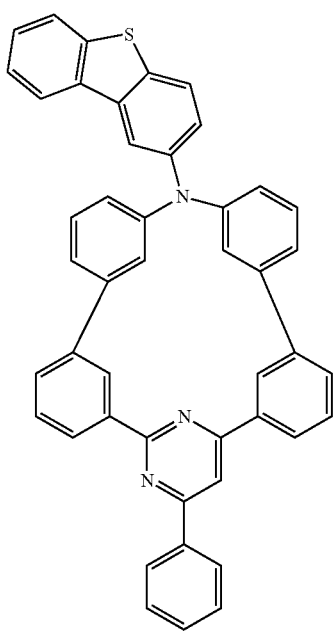

173
-continued
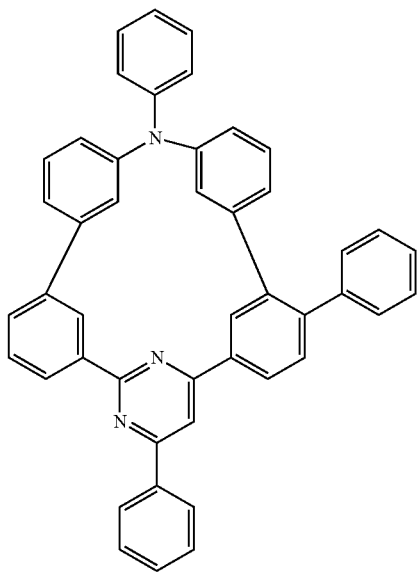
27
174
-continued
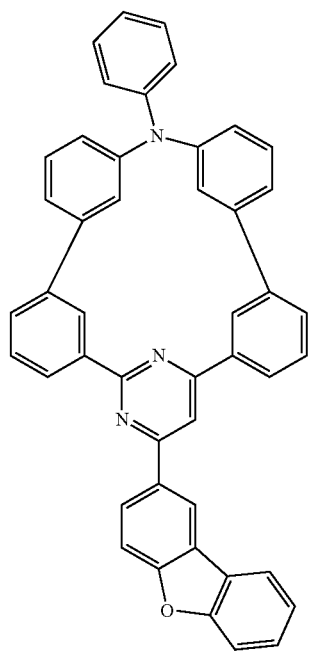
29
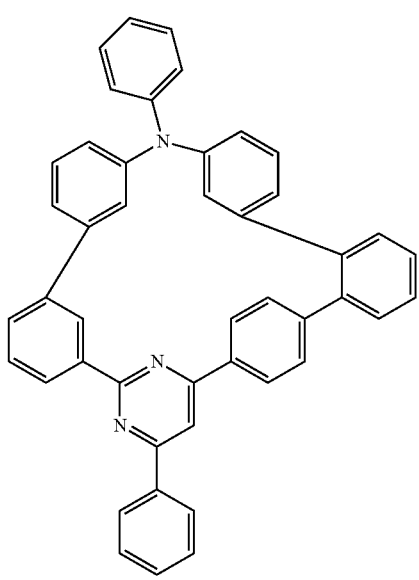
28
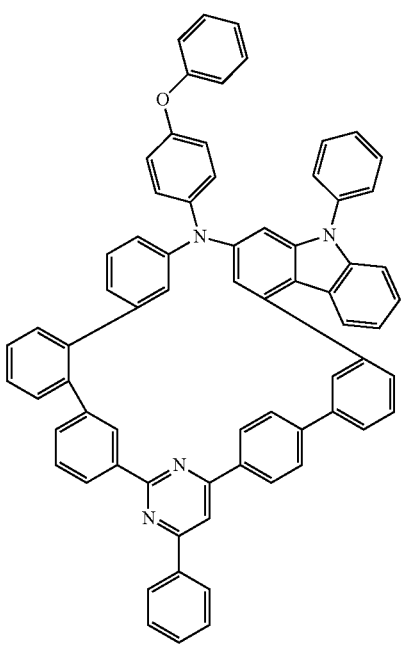
30

-continued
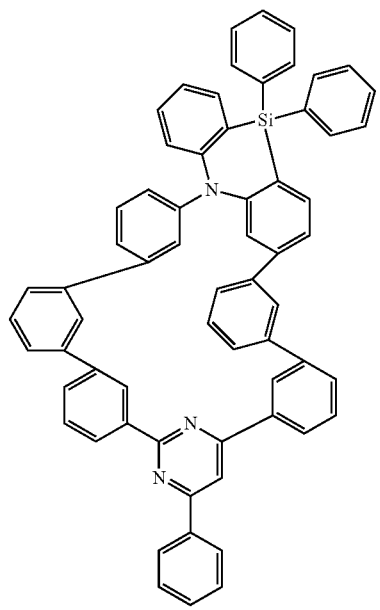
31
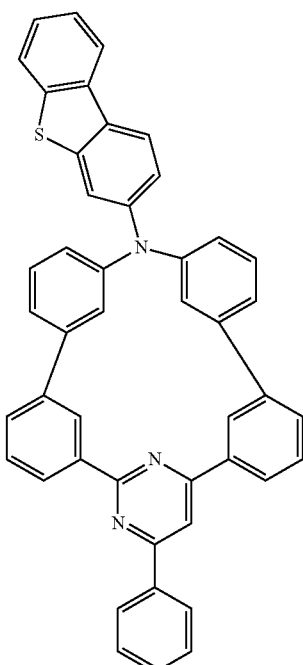
33
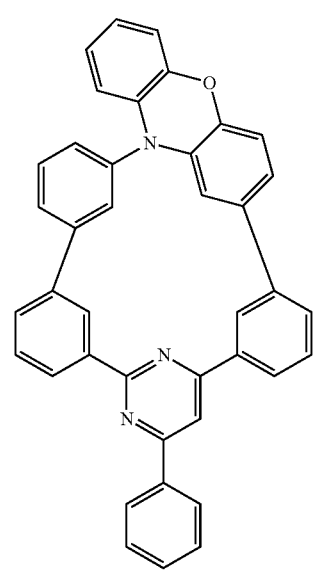
32
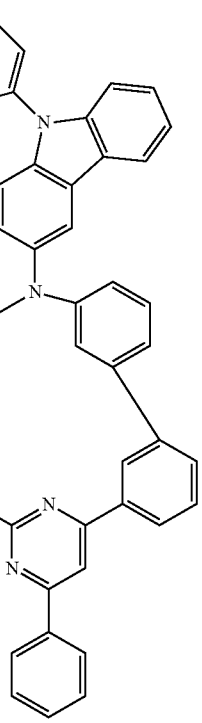
34

-continued
177
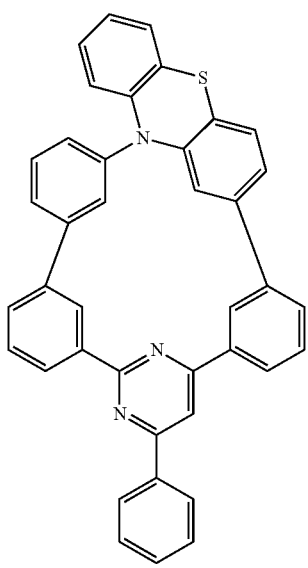
36
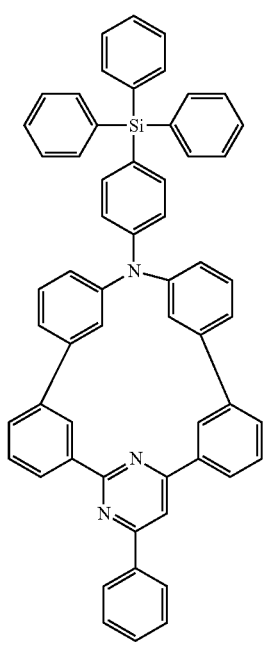
-continued
37
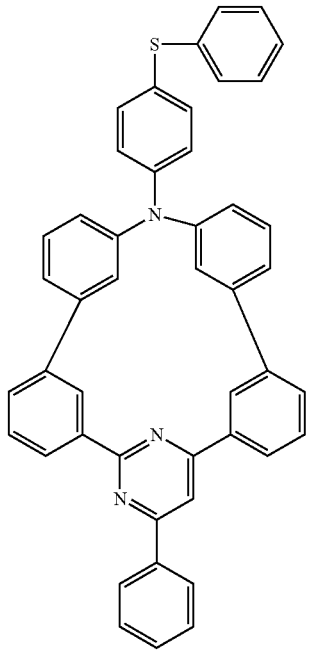
38
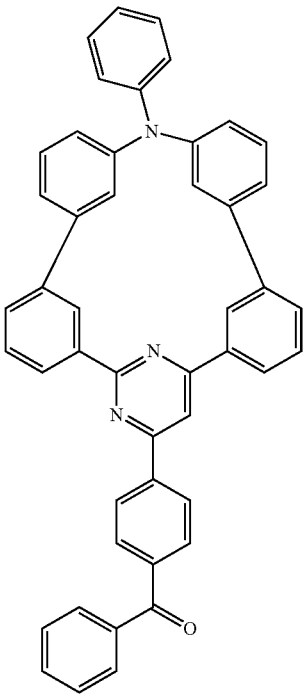
* * * * *